United States Patent
Abdou et al.

(10) Patent No.: US 10,111,757 B2
(45) Date of Patent: Oct. 30, 2018

(54) DEVICES AND METHODS FOR SPINAL STABILIZATION AND INSTRUMENTATION

(71) Applicant: Cogent Spine, LLC, San Diego, CA (US)

(72) Inventors: Samy Abdou, San Diego, CA (US); Brian Bowman, Carlsbad, CA (US); Benjamin Arnold, San Diego, CA (US); Jude Paganelli, San Diego, CA (US)

(73) Assignee: Cogent Spine, LLC, San Diego, CA (US)

( * ) Notice: Subject to any disclaimer, the term of this patent is extended or adjusted under 35 U.S.C. 154(b) by 33 days.

(21) Appl. No.: 15/138,072

(22) Filed: Apr. 25, 2016

(65) Prior Publication Data

US 2016/0310293 A1 Oct. 27, 2016

Related U.S. Application Data

(62) Division of application No. 13/797,586, filed on Mar. 12, 2013, now Pat. No. 9,320,617.
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/447* (2013.01); *A61F 2/4611* (2013.01);
(Continued)

(58) Field of Classification Search
CPC .. A61F 2002/30392; A61F 2002/30397; A61F 2002/30471; A61F 2/44; A61F 2002/4415; A61F 2002/448
See application file for complete search history.

(56) References Cited

U.S. PATENT DOCUMENTS

| 824,983 A | 7/1906 | Farrington |
|---|---|---|
| 2,248,054 A | 7/1941 | Becker |

(Continued)

FOREIGN PATENT DOCUMENTS

| EP | 1180348 A2 | 2/2002 |
|---|---|---|
| FR | 2781359 A1 | 1/2000 |

(Continued)

OTHER PUBLICATIONS

Netter F., Atlas of Human Anatomy, 3rd Edition, Icon Learning Systems, Tegerboro, New Jersey.
(Continued)

*Primary Examiner* — David Bates
(74) *Attorney, Agent, or Firm* — Gazdzinski & Associates, PC

(57) ABSTRACT

Apparatus and methods for providing spinal percutaneous delivery of an implant that can rigidly fixate the spinous process of a first superior bone and a second inferior bone of a functional spinal unit. In one aspect, the device comprises two bone abutment members connected via an interconnecting member. In another aspect, the method comprises implanting at least two spinal implant apparatus within a target disc space via an implantation apparatus. In another aspect, a placement instrument comprising an implant delivery segment, an anchor segment, and an articulating arm is disclosed.

44 Claims, 47 Drawing Sheets

Related U.S. Application Data

(60) Provisional application No. 61/795,658, filed on Oct. 22, 2012, provisional application No. 61/795,703, filed on Oct. 23, 2012.

(52) U.S. Cl.
CPC ............ *A61F 2002/30062* (2013.01); *A61F 2002/30092* (2013.01); *A61F 2002/3092* (2013.01); *A61F 2002/3093* (2013.01); *A61F 2002/30166* (2013.01); *A61F 2002/30392* (2013.01); *A61F 2002/30397* (2013.01); *A61F 2002/30471* (2013.01); *A61F 2002/30774* (2013.01); *A61F 2002/30836* (2013.01); *A61F 2002/30904* (2013.01); *A61F 2002/448* (2013.01); *A61F 2002/4415* (2013.01); *A61F 2002/4475* (2013.01); *A61F 2002/4495* (2013.01)

(56) References Cited

U.S. PATENT DOCUMENTS

| | | |
|---|---|---|
| 2,329,398 A | 9/1943 | Duffy |
| 2,370,407 A | 2/1945 | McCartney |
| 2,574,352 A | 11/1951 | Senter |
| 3,236,141 A | 2/1966 | Smith |
| 3,604,487 A | 9/1971 | Gilbert |
| 3,659,595 A | 5/1972 | Haboush |
| 3,867,728 A | 2/1975 | Stubstad et al. |
| 4,254,763 A | 3/1981 | McCready et al. |
| 4,399,813 A | 8/1983 | Barber |
| 4,636,217 A | 1/1987 | Ogilvie et al. |
| 4,820,305 A | 4/1989 | Harms et al. |
| 4,834,757 A | 5/1989 | Brantigan |
| 4,877,020 A | 10/1989 | Vich |
| 4,903,692 A | 2/1990 | Reese |
| 4,907,577 A | 3/1990 | Wu |
| 4,961,740 A | 10/1990 | Ray et al. |
| 5,015,247 A | 5/1991 | Michelson |
| 5,055,104 A | 10/1991 | Ray |
| 5,192,327 A | 3/1993 | Brantigan |
| 5,236,460 A | 8/1993 | Barber |
| 5,252,016 A | 10/1993 | Schmid et al. |
| 5,275,601 A | 1/1994 | Gogolewski et al. |
| 5,352,231 A | 10/1994 | Brumfield et al. |
| 5,354,292 A | 10/1994 | Braeuer et al. |
| 5,360,429 A | 11/1994 | Jeanson et al. |
| 5,361,766 A | 11/1994 | Nichols et al. |
| 5,397,364 A | 3/1995 | Kozak et al. |
| 5,439,339 A | 8/1995 | Batchelor |
| 5,443,514 A | 8/1995 | Steffee |
| 5,458,638 A | 10/1995 | Kuslich et al. |
| 5,484,440 A | 1/1996 | Allard |
| 5,487,742 A | 1/1996 | Cotrel |
| 5,489,308 A | 2/1996 | Kuslich et al. |
| 5,531,747 A | 7/1996 | Ray |
| 5,531,751 A | 7/1996 | Schultheiss et al. |
| 5,534,001 A | 7/1996 | Schlapfer et al. |
| 5,534,027 A | 7/1996 | Hodorek |
| 5,545,164 A | 8/1996 | Howland |
| 5,558,674 A | 9/1996 | Heggeness et al. |
| 5,591,166 A | 1/1997 | Bernhardt et al. |
| 5,599,279 A | 2/1997 | Slotman et al. |
| 5,607,426 A | 3/1997 | Ralph et al. |
| 5,609,635 A | 3/1997 | Michelson |
| 5,609,637 A | 3/1997 | Biedermann et al. |
| 5,616,142 A | 4/1997 | Yuan et al. |
| 5,649,931 A | 7/1997 | Bryant et al. |
| 5,672,176 A | 9/1997 | Biedermann et al. |
| 5,681,311 A | 10/1997 | Foley et al. |
| 5,681,312 A | 10/1997 | Yuan et al. |
| 5,681,313 A | 10/1997 | Diez |
| 5,683,394 A | 11/1997 | Rinner |
| 5,702,451 A | 12/1997 | Biedermann et al. |
| 5,704,936 A | 1/1998 | Mazel |
| 5,707,372 A | 1/1998 | Errico et al. |
| 5,709,686 A | 1/1998 | Talos et al. |
| 5,713,900 A | 2/1998 | Benzel et al. |
| 5,716,357 A | 2/1998 | Rogozinski |
| 5,735,853 A | 4/1998 | Olerud |
| 5,741,261 A | 4/1998 | Moskovitz et al. |
| 5,749,916 A | 5/1998 | Richelsoph |
| 5,776,199 A | 7/1998 | Michelson |
| 5,782,830 A | 7/1998 | Farris |
| 5,782,832 A | 7/1998 | Larsen et al. |
| 5,865,848 A | 2/1999 | Baker |
| 5,876,402 A | 3/1999 | Errico et al. |
| 5,888,222 A | 3/1999 | Coates et al. |
| 5,888,224 A | 3/1999 | Beckers et al. |
| 5,904,683 A | 5/1999 | Pohndorf et al. |
| 5,908,382 A | 6/1999 | Koros et al. |
| 5,954,722 A | 9/1999 | Bono |
| 5,964,763 A | 10/1999 | Incavo et al. |
| 5,971,987 A | 10/1999 | Huxel et al. |
| 5,976,140 A | 11/1999 | Haas |
| 5,980,522 A | 11/1999 | Koros et al. |
| 5,984,967 A | 11/1999 | Zdeblick et al. |
| 5,993,449 A | 11/1999 | Schlaepfer et al. |
| 6,004,326 A | 12/1999 | Castro et al. |
| 6,033,170 A | 3/2000 | Gold |
| 6,039,761 A * | 3/2000 | Li .................... A61B 17/70 623/17.16 |
| 6,045,579 A | 4/2000 | Hochshuler et al. |
| 6,059,786 A | 5/2000 | Jackson |
| 6,071,310 A | 6/2000 | Picha et al. |
| 6,080,193 A | 6/2000 | Hochshuler et al. |
| 6,083,225 A | 7/2000 | Winslow et al. |
| 6,086,613 A | 7/2000 | Camino et al. |
| 6,099,531 A | 8/2000 | Bonutti |
| 6,117,135 A | 9/2000 | Schlaepfer |
| 6,126,689 A | 10/2000 | Brett |
| 6,139,316 A | 10/2000 | Sachdeva et al. |
| 6,139,549 A | 10/2000 | Keller |
| 6,156,037 A | 12/2000 | Lehuec et al. |
| 6,159,244 A | 12/2000 | Suddaby |
| 6,174,311 B1 | 1/2001 | Branch et al. |
| 6,176,882 B1 | 1/2001 | Biedermann et al. |
| 6,187,005 B1 | 2/2001 | Brace et al. |
| 6,193,757 B1 | 2/2001 | Foley et al. |
| 6,197,033 B1 | 3/2001 | Haid, Jr. et al. |
| 6,200,322 B1 | 3/2001 | Branch et al. |
| 6,206,922 B1 | 3/2001 | Zdeblick et al. |
| 6,210,412 B1 | 4/2001 | Michelson |
| 6,224,595 B1 | 5/2001 | Michelson |
| 6,228,022 B1 | 5/2001 | Friesem et al. |
| 6,245,072 B1 | 6/2001 | Zdeblick et al. |
| 6,248,110 B1 | 6/2001 | Reiley et al. |
| 6,251,112 B1 | 6/2001 | Jackson |
| 6,251,140 B1 | 6/2001 | Marino et al. |
| 6,258,125 B1 | 7/2001 | Paul et al. |
| 6,264,656 B1 | 7/2001 | Michelson |
| 6,270,498 B1 | 8/2001 | Michelson |
| 6,277,149 B1 | 8/2001 | Boyle et al. |
| 6,287,308 B1 | 9/2001 | Betz et al. |
| 6,302,843 B1 | 10/2001 | Lees et al. |
| 6,302,914 B1 | 10/2001 | Michelson |
| 6,306,136 B1 | 10/2001 | Baccelli |
| 6,309,391 B1 | 10/2001 | Crandall et al. |
| RE37,479 E | 12/2001 | Kuslich |
| 6,331,179 B1 | 12/2001 | Freid et al. |
| 6,342,074 B1 | 1/2002 | Simpson |
| 6,348,058 B1 | 2/2002 | Melkent et al. |
| 6,361,258 B1 | 3/2002 | Heesch |
| RE37,665 E | 4/2002 | Ralph |
| 6,364,880 B1 | 4/2002 | Michelson |
| 6,371,988 B1 | 4/2002 | Pafford et al. |
| 6,375,655 B1 | 4/2002 | Zdeblick et al. |
| 6,402,752 B2 | 6/2002 | Schaffler-Wachter et al. |
| 6,402,756 B1 | 6/2002 | Ralph et al. |
| 6,419,706 B1 | 7/2002 | Graf |
| 6,440,139 B2 | 8/2002 | Michelson |
| 6,440,170 B1 | 8/2002 | Jackson |
| 6,447,547 B1 | 9/2002 | Michelson |

(56) References Cited

U.S. PATENT DOCUMENTS

| | | |
|---|---|---|
| 6,447,548 B1 | 9/2002 | Ralph et al. |
| 6,471,724 B2 | 10/2002 | Zdeblick et al. |
| 6,527,773 B1 | 3/2003 | Lin et al. |
| 6,537,279 B1 | 3/2003 | Michelson |
| 6,540,785 B1 | 4/2003 | Gill et al. |
| 6,554,863 B2 | 4/2003 | Paul et al. |
| 6,558,387 B2 | 5/2003 | Errico et al. |
| 6,562,074 B2 | 5/2003 | Gerbec et al. |
| 6,569,168 B2 | 5/2003 | Lin |
| 6,575,899 B1 | 6/2003 | Foley et al. |
| 6,575,981 B1 | 6/2003 | Boyd et al. |
| 6,576,016 B1 | 6/2003 | Hochshuler et al. |
| 6,582,431 B1 | 6/2003 | Ray |
| 6,595,995 B2 | 7/2003 | Zdeblick et al. |
| 6,599,290 B2 | 7/2003 | Bailey et al. |
| 6,607,530 B1 | 8/2003 | Carl et al. |
| 6,610,089 B1 | 8/2003 | Liu et al. |
| 6,613,091 B1 | 9/2003 | Zdeblick et al. |
| 6,616,695 B1 | 9/2003 | Crozet et al. |
| 6,638,310 B2 | 10/2003 | Lin et al. |
| 6,641,614 B1 | 11/2003 | Wagner et al. |
| 6,645,206 B1 | 11/2003 | Zdeblick et al. |
| 6,645,207 B2 | 11/2003 | Dixon et al. |
| 6,648,895 B2 | 11/2003 | Burkus et al. |
| 6,648,917 B2 | 11/2003 | Gerbec et al. |
| 6,663,631 B2 | 12/2003 | Kuntz |
| 6,666,866 B2 | 12/2003 | Martz et al. |
| 6,666,867 B2 | 12/2003 | Ralph et al. |
| 6,666,891 B2 | 12/2003 | Boehm et al. |
| 6,679,883 B2 | 1/2004 | Hawkes et al. |
| 6,692,495 B1 | 2/2004 | Zacouto |
| 6,706,067 B2 | 3/2004 | Shimp et al. |
| 6,706,070 B1 | 3/2004 | Wagner et al. |
| 6,706,922 B2 | 3/2004 | Wolff et al. |
| 6,709,389 B2 | 3/2004 | Farascioni |
| 6,712,819 B2 | 3/2004 | Zucherman et al. |
| 6,712,852 B1 | 3/2004 | Chung et al. |
| 6,719,794 B2 | 4/2004 | Gerber et al. |
| 6,723,043 B2 | 4/2004 | Kleeman et al. |
| 6,723,096 B1 | 4/2004 | Dorchak et al. |
| 6,723,100 B2 | 4/2004 | Biedermann et al. |
| 6,723,126 B1 | 4/2004 | Berry |
| 6,730,127 B2 | 5/2004 | Michelson |
| 6,746,454 B2 | 6/2004 | Winterbottom et al. |
| 6,752,832 B2 | 6/2004 | Neumann |
| 6,761,738 B1 | 7/2004 | Boyd |
| 6,767,367 B1 | 7/2004 | Michelson |
| 6,770,074 B2 | 8/2004 | Michelson |
| 6,770,096 B2 | 8/2004 | Bolger et al. |
| 6,780,192 B2 | 8/2004 | McKay et al. |
| 6,827,722 B1 | 12/2004 | Schoenefeld |
| 6,830,570 B1 | 12/2004 | Frey et al. |
| 6,830,571 B2 | 12/2004 | Lenke et al. |
| 6,830,589 B2 | 12/2004 | Erickson |
| 6,849,093 B2 | 2/2005 | Michelson |
| 6,852,127 B2 | 2/2005 | Varga et al. |
| 6,852,129 B2 | 2/2005 | Gerbec et al. |
| 6,855,147 B2 | 2/2005 | Harrington et al. |
| 6,863,673 B2 | 3/2005 | Gerbec et al. |
| 6,881,228 B2 | 4/2005 | Zdeblick et al. |
| 6,890,355 B2 | 5/2005 | Michelson |
| 6,896,680 B2 | 5/2005 | Michelson |
| 6,902,566 B2 | 6/2005 | Zucherman et al. |
| 6,911,045 B2 | 6/2005 | Shimp |
| 6,926,737 B2 | 8/2005 | Jackson |
| 6,949,105 B2 | 9/2005 | Bryan et al. |
| 6,953,477 B2 | 10/2005 | Berry |
| 6,964,687 B1 | 11/2005 | Bernard et al. |
| 6,972,019 B2 | 12/2005 | Michelson |
| 6,979,334 B2 | 12/2005 | Dalton |
| 6,984,245 B2 | 1/2006 | McGahan et al. |
| 6,986,772 B2 | 1/2006 | Michelson |
| 6,991,654 B2 | 1/2006 | Foley |
| 7,018,415 B1 | 3/2006 | McKay |
| 7,018,416 B2 | 3/2006 | Hanson et al. |
| 7,033,362 B2 | 4/2006 | McGahan et al. |
| 7,037,339 B2 | 5/2006 | Houfburg |
| 7,044,971 B2 | 5/2006 | Suddaby |
| 7,070,598 B2 | 7/2006 | Lim et al. |
| 7,083,625 B2 | 8/2006 | Berry |
| 7,097,648 B1 | 8/2006 | Globerman et al. |
| 7,118,579 B2 | 10/2006 | Michelson |
| 7,125,425 B2 | 10/2006 | Simonton et al. |
| 7,156,806 B2 | 1/2007 | Dobrovolny |
| 7,166,121 B2 | 1/2007 | Reiley et al. |
| 7,169,183 B2 | 1/2007 | Liu et al. |
| 7,204,851 B2 | 4/2007 | Trieu et al. |
| 7,211,085 B2 | 5/2007 | Michelson |
| 7,217,291 B2 | 5/2007 | Zucherman et al. |
| 7,227,477 B2 | 6/2007 | Ye |
| 7,235,105 B2 | 6/2007 | Jackson |
| 7,241,297 B2 | 7/2007 | Shaolian et al. |
| 7,252,673 B2 | 8/2007 | Lim |
| 7,276,081 B1 | 10/2007 | Coates et al. |
| 7,276,082 B2 | 10/2007 | Zdeblick et al. |
| 7,282,063 B2 | 10/2007 | Cohen et al. |
| 7,291,149 B1 | 11/2007 | Michelson |
| 7,300,441 B2 | 11/2007 | Haid et al. |
| 7,311,734 B2 | 12/2007 | Hoeck et al. |
| 7,318,840 B2 | 1/2008 | McKay |
| 7,326,216 B2 | 2/2008 | Bertagnoli et al. |
| 7,331,961 B2 | 2/2008 | Abdou |
| 7,341,587 B2 | 3/2008 | Molz et al. |
| 7,473,276 B2 | 1/2009 | Aebi et al. |
| 7,476,228 B2 | 1/2009 | Abdou |
| 7,491,205 B1 | 2/2009 | Michelson |
| 7,497,859 B2 | 3/2009 | Zucherman et al. |
| 7,534,265 B1 | 5/2009 | Boyd et al. |
| 7,537,616 B1 | 5/2009 | Branch et al. |
| 7,547,308 B2 | 6/2009 | Bertagnoli et al. |
| 7,547,325 B2 | 6/2009 | Biedermann et al. |
| 7,559,930 B2 | 7/2009 | Allard et al. |
| 7,572,276 B2 | 8/2009 | Lim et al. |
| 7,575,580 B2 | 8/2009 | Lim et al. |
| 7,578,820 B2 | 8/2009 | Moore et al. |
| 7,591,851 B2 | 9/2009 | Winslow et al. |
| 7,594,919 B2 | 9/2009 | Peterman |
| 7,597,694 B2 | 10/2009 | Lim et al. |
| 7,618,423 B1 | 11/2009 | Valentine et al. |
| 7,621,953 B2 | 11/2009 | Braddock et al. |
| 7,621,957 B2 | 11/2009 | Errico et al. |
| 7,625,379 B2 | 12/2009 | Puno et al. |
| 7,625,380 B2 | 12/2009 | Drewry et al. |
| 7,635,371 B2 | 12/2009 | McGahan et al. |
| 7,641,690 B2 | 1/2010 | Abdou et al. |
| 7,641,693 B2 | 1/2010 | Gutlin et al. |
| 7,645,281 B2 | 1/2010 | Marik |
| 7,682,396 B2 | 3/2010 | Beaurain et al. |
| 7,708,743 B2 | 5/2010 | Anderson et al. |
| 7,749,231 B2 | 7/2010 | Bonvallet et al. |
| 7,749,269 B2 | 7/2010 | Peterman et al. |
| 7,749,270 B2 | 7/2010 | Peterman |
| 7,753,958 B2 | 7/2010 | Gordon et al. |
| 7,758,648 B2 | 7/2010 | Castleman et al. |
| 7,763,078 B2 | 7/2010 | Peterman et al. |
| 7,766,918 B2 | 8/2010 | Allard et al. |
| 7,771,432 B2 | 8/2010 | Schwab et al. |
| 7,771,473 B2 | 8/2010 | Thramann |
| 7,780,732 B2 | 8/2010 | Abernathie et al. |
| 7,794,501 B2 | 9/2010 | Edie et al. |
| 7,799,081 B2 | 9/2010 | McKinley |
| 7,815,683 B2 | 10/2010 | Melkent et al. |
| 7,828,807 B2 | 11/2010 | Lehuec et al. |
| 7,837,732 B2 | 11/2010 | Zucherman et al. |
| 7,837,734 B2 | 11/2010 | Zucherman et al. |
| 7,857,818 B2 | 12/2010 | Trieu et al. |
| 7,875,034 B2 | 1/2011 | Josse et al. |
| 7,875,078 B2 | 1/2011 | Wysocki et al. |
| 7,883,542 B2 * | 2/2011 | Zipnick ............ A61B 17/320016 623/17.11 |
| 7,901,409 B2 | 3/2011 | Canaveral et al. |
| 7,901,458 B2 | 3/2011 | Deridder et al. |
| 7,909,870 B2 | 3/2011 | Kraus |
| 7,959,677 B2 | 6/2011 | Landry et al. |

(56) References Cited

U.S. PATENT DOCUMENTS

| | | |
|---|---|---|
| 7,988,699 B2 | 8/2011 | Martz et al. |
| 8,002,833 B2 | 8/2011 | Fabris et al. |
| 8,034,109 B2 | 10/2011 | Zwirkoski |
| 8,043,376 B2 | 10/2011 | Falahee |
| 8,043,380 B1 | 10/2011 | Park et al. |
| 8,062,299 B2 | 11/2011 | McGahan et al. |
| 8,066,714 B2 | 11/2011 | Shipp et al. |
| 8,083,798 B2 | 12/2011 | Allard et al. |
| 8,123,807 B2 | 2/2012 | Kim |
| 8,163,026 B2 | 4/2012 | Gray |
| 8,251,997 B2 | 8/2012 | Michelson |
| 8,268,004 B2 | 9/2012 | Castleman et al. |
| 8,349,012 B2 | 1/2013 | McKay |
| 8,388,687 B2 | 3/2013 | Gimbel et al. |
| 8,454,621 B2 | 6/2013 | Deridder et al. |
| 8,454,694 B2 | 6/2013 | Armstrong et al. |
| 8,465,547 B2 | 6/2013 | Melkent et al. |
| 8,480,747 B2 | 7/2013 | Melkent et al. |
| 8,486,147 B2 * | 7/2013 | de Villiers ............ A61F 2/4425 606/914 |
| 8,506,629 B2 | 8/2013 | Weiland |
| 8,663,331 B2 * | 3/2014 | McClellan, III ...... A61F 2/4455 623/17.11 |
| 8,795,375 B2 * | 8/2014 | Malberg .................. A61F 2/442 623/17.16 |
| 8,845,728 B1 | 9/2014 | Abdou |
| 8,876,904 B2 | 11/2014 | Pimenta et al. |
| 8,911,441 B2 | 12/2014 | Dace et al. |
| 8,956,415 B2 | 2/2015 | Cowan |
| 8,998,905 B2 | 4/2015 | Marik et al. |
| 9,011,538 B2 | 4/2015 | Allard et al. |
| 9,308,099 B2 * | 4/2016 | Triplett ................ A61F 2/4465 |
| 9,364,338 B2 * | 6/2016 | Malberg .................. A61F 2/442 |
| 9,408,717 B2 * | 8/2016 | Perrow ................ A61F 2/4455 |
| 9,445,918 B1 * | 9/2016 | Lin .................... A61B 17/8819 |
| 2001/0001129 A1 | 5/2001 | McKay et al. |
| 2002/0016595 A1 | 2/2002 | Michelson |
| 2002/0045945 A1 | 4/2002 | Liu et al. |
| 2002/0055741 A1 | 5/2002 | Schlapfer et al. |
| 2002/0082700 A1 | 6/2002 | Bianchi et al. |
| 2002/0099386 A1 | 7/2002 | Beger et al. |
| 2002/0111628 A1 | 8/2002 | Ralph et al. |
| 2002/0143328 A1 | 10/2002 | Shluzas et al. |
| 2002/0169453 A1 | 11/2002 | Berger |
| 2002/0183755 A1 | 12/2002 | Michelson |
| 2002/0188296 A1 | 12/2002 | Michelson |
| 2003/0023305 A1 | 1/2003 | McKay |
| 2003/0078583 A1 | 4/2003 | Biedermann et al. |
| 2003/0083747 A1 | 5/2003 | Winterbottom et al. |
| 2003/0093153 A1 | 5/2003 | Banick et al. |
| 2003/0153913 A1 | 8/2003 | Altarac et al. |
| 2003/0163199 A1 | 8/2003 | Boehm et al. |
| 2004/0049271 A1 | 3/2004 | Biedermann et al. |
| 2004/0054412 A1 | 3/2004 | Gerbec et al. |
| 2004/0059318 A1 | 3/2004 | Zhang et al. |
| 2004/0087947 A1 | 5/2004 | Lim et al. |
| 2004/0093083 A1 | 5/2004 | Branch et al. |
| 2004/0098129 A1 | 5/2004 | Lin |
| 2004/0106927 A1 | 6/2004 | Ruffner et al. |
| 2004/0143264 A1 | 7/2004 | McAfee |
| 2004/0153065 A1 | 8/2004 | Lim |
| 2004/0172134 A1 | 9/2004 | Berry |
| 2004/0186572 A1 | 9/2004 | Lange et al. |
| 2004/0204713 A1 | 10/2004 | Abdou |
| 2004/0249380 A1 | 12/2004 | Glascott |
| 2004/0249461 A1 | 12/2004 | Ferree |
| 2005/0004573 A1 | 1/2005 | Abdou |
| 2005/0021041 A1 | 1/2005 | Michelson |
| 2005/0033432 A1 | 2/2005 | Gordon et al. |
| 2005/0038511 A1 | 2/2005 | Martz et al. |
| 2005/0085909 A1 | 4/2005 | Eisermann |
| 2005/0119747 A1 | 6/2005 | Fabris et al. |
| 2005/0149188 A1 | 7/2005 | Cook et al. |
| 2005/0159756 A1 | 7/2005 | Ray |
| 2005/0159815 A1 | 7/2005 | Kamimura et al. |
| 2005/0171541 A1 | 8/2005 | Boehm, Jr. et al. |
| 2005/0171610 A1 | 8/2005 | Humphreys et al. |
| 2005/0177163 A1 | 8/2005 | Abdou et al. |
| 2005/0222683 A1 | 10/2005 | Berry |
| 2005/0251258 A1 | 11/2005 | Jackson |
| 2005/0273120 A1 | 12/2005 | Abdou et al. |
| 2005/0273171 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0288669 A1 | 12/2005 | Abdou et al. |
| 2006/0004453 A1 | 1/2006 | Bartish et al. |
| 2006/0058878 A1 | 3/2006 | Michelson |
| 2006/0074488 A1 | 4/2006 | Abdou et al. |
| 2006/0084981 A1 | 4/2006 | Shluzas |
| 2006/0089656 A1 | 4/2006 | Allard et al. |
| 2006/0089718 A1 | 4/2006 | Zucherman et al. |
| 2006/0122701 A1 | 6/2006 | Kiester |
| 2006/0129244 A1 | 6/2006 | Ensign |
| 2006/0142858 A1 * | 6/2006 | Colleran ............ A61F 2/4465 623/17.11 |
| 2006/0149278 A1 | 7/2006 | Abdou |
| 2006/0149284 A1 | 7/2006 | McCormack et al. |
| 2006/0149385 A1 | 7/2006 | McKay |
| 2006/0195192 A1 | 8/2006 | Gordon et al. |
| 2006/0217710 A1 | 9/2006 | Abdou |
| 2006/0217731 A1 | 9/2006 | Gil et al. |
| 2006/0229615 A1 | 10/2006 | Abdou et al. |
| 2006/0229729 A1 | 10/2006 | Gordon et al. |
| 2006/0241641 A1 | 10/2006 | Albans et al. |
| 2006/0247655 A1 | 11/2006 | Francis et al. |
| 2006/0247679 A1 | 11/2006 | Peterman |
| 2006/0247778 A1 | 11/2006 | Ferree et al. |
| 2006/0253201 A1 | 11/2006 | McLuen |
| 2007/0016218 A1 | 1/2007 | Winslow et al. |
| 2007/0043442 A1 | 2/2007 | Abernathie et al. |
| 2007/0049935 A1 | 3/2007 | Edidin et al. |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0093828 A1 | 4/2007 | Abdou et al. |
| 2007/0093901 A1 | 4/2007 | Grotz et al. |
| 2007/0106383 A1 | 5/2007 | Abdou et al. |
| 2007/0123884 A1 | 5/2007 | Abdou |
| 2007/0161962 A1 | 7/2007 | Edie et al. |
| 2007/0162127 A1 | 7/2007 | Peterman et al. |
| 2007/0162138 A1 | 7/2007 | Heinz |
| 2007/0179614 A1 | 8/2007 | Heinz et al. |
| 2007/0191861 A1 | 8/2007 | Allard et al. |
| 2007/0191951 A1 | 8/2007 | Branch et al. |
| 2007/0225812 A1 | 9/2007 | Gill |
| 2007/0255415 A1 | 11/2007 | Edie et al. |
| 2007/0270963 A1 | 11/2007 | Melkent et al. |
| 2007/0270968 A1 | 11/2007 | Baynham et al. |
| 2007/0282448 A1 | 12/2007 | Abdou |
| 2007/0293949 A1 | 12/2007 | Salerni et al. |
| 2007/0299521 A1 | 12/2007 | Glenn et al. |
| 2008/0021559 A1 | 1/2008 | Thramann |
| 2008/0027544 A1 | 1/2008 | Melkent |
| 2008/0045968 A1 | 2/2008 | Yu et al. |
| 2008/0065222 A1 | 3/2008 | Hamada |
| 2008/0119853 A1 | 5/2008 | Felt et al. |
| 2008/0133014 A1 | 6/2008 | Gately et al. |
| 2008/0133016 A1 | 6/2008 | Heinz |
| 2008/0133017 A1 | 6/2008 | Beyar et al. |
| 2008/0140204 A1 | 6/2008 | Heinz |
| 2008/0140207 A1 | 6/2008 | Olmos et al. |
| 2008/0161821 A1 | 7/2008 | Heinz |
| 2008/0167657 A1 | 7/2008 | Greenhalgh |
| 2008/0183204 A1 | 7/2008 | Greenhalgh et al. |
| 2008/0183211 A1 | 7/2008 | Lamborne et al. |
| 2008/0188941 A1 | 8/2008 | Grotz |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0300686 A1 | 12/2008 | Khoo |
| 2008/0312743 A1 * | 12/2008 | Vila ........................ A61F 2/442 623/17.16 |
| 2008/0319487 A1 | 12/2008 | Fielding et al. |

(56) References Cited

U.S. PATENT DOCUMENTS

| | | |
|---|---|---|
| 2008/0319549 A1 | 12/2008 | Greenhalgh et al. |
| 2009/0012623 A1 | 1/2009 | Sack et al. |
| 2009/0024217 A1 | 1/2009 | Levy et al. |
| 2009/0093884 A1 | 4/2009 | Bass |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0187249 A1 | 7/2009 | Osman |
| 2009/0204218 A1 | 8/2009 | Richelsoph |
| 2009/0222100 A1 | 9/2009 | Cipoletti et al. |
| 2009/0228110 A1 | 9/2009 | McClintock |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2010/0049324 A1 | 2/2010 | Valdevit et al. |
| 2010/0070041 A1 | 3/2010 | Peterman et al. |
| 2010/0082109 A1 | 4/2010 | Greenhalgh et al. |
| 2010/0179657 A1 | 7/2010 | Greenhalgh et al. |
| 2010/0185291 A1 | 7/2010 | Jimenez et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger et al. |
| 2010/0222884 A1 | 9/2010 | Greenhalgh |
| 2010/0234952 A1 | 9/2010 | Peterman |
| 2010/0249933 A1 | 9/2010 | Trieu |
| 2010/0280622 A1 | 11/2010 | McKinley |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0305705 A1 | 12/2010 | Butler et al. |
| 2010/0331981 A1 | 12/2010 | Mohammed |
| 2010/0331985 A1 | 12/2010 | Gordon et al. |
| 2011/0029083 A1 | 2/2011 | Hynes et al. |
| 2011/0035011 A1 | 2/2011 | Cain |
| 2011/0093074 A1 | 4/2011 | Glerum et al. |
| 2011/0125266 A1 | 5/2011 | Rodgers et al. |
| 2011/0213465 A1 | 9/2011 | Landry et al. |
| 2011/0251693 A1 | 10/2011 | Barreiro et al. |
| 2011/0288644 A1 | 11/2011 | Gray et al. |
| 2011/0288645 A1 | 11/2011 | Braddock, Jr. et al. |
| 2011/0301712 A1 | 12/2011 | Palmatier et al. |
| 2012/0029639 A1 | 2/2012 | Blackwell et al. |
| 2012/0197401 A1 | 8/2012 | Duncan et al. |
| 2012/0197402 A1 | 8/2012 | Blackwell et al. |
| 2012/0277864 A1 | 11/2012 | Brodke et al. |
| 2013/0041471 A1* | 2/2013 | Siegal ............... A61F 2/442 623/17.16 |
| 2013/0079883 A1* | 3/2013 | Butler ............... A61F 2/4425 623/17.16 |
| 2013/0150970 A1 | 6/2013 | Thaiyananthan |
| 2013/0274884 A1 | 10/2013 | Matsumoto et al. |
| 2013/0325128 A1 | 12/2013 | Perloff et al. |
| 2014/0277490 A1* | 9/2014 | Perloff ............... A61F 2/442 623/17.16 |
| 2014/0277499 A1* | 9/2014 | Ainsworth ............ A61B 17/70 623/17.16 |
| 2014/0277502 A1 | 9/2014 | Schiffman et al. |
| 2014/0379086 A1* | 12/2014 | Elahinia ............. A61F 2/4465 623/17.16 |
| 2015/0057755 A1 | 2/2015 | Suddaby et al. |

FOREIGN PATENT DOCUMENTS

| | | |
|---|---|---|
| WO | WO-9000037 A1 | 1/1990 |
| WO | WO-9723174 A1 | 7/1997 |
| WO | WO-9730666 A2 | 8/1997 |
| WO | WO-9938463 A2 | 8/1999 |
| WO | WO-0023015 A1 | 4/2000 |
| WO | WO-0128465 A2 | 4/2001 |
| WO | WO-0145577 A2 | 6/2001 |
| WO | WO-0211633 A2 | 2/2002 |
| WO | WO-02058600 A2 | 8/2002 |
| WO | WO-03051212 A2 | 6/2003 |
| WO | WO-2004032726 A2 | 4/2004 |
| WO | WO-2004062482 A2 | 7/2004 |
| WO | WO-2004093702 A2 | 11/2004 |
| WO | WO-2005122922 A2 | 12/2005 |
| WO | WO-2006041963 A2 | 4/2006 |
| WO | WO-2006042335 A1 | 4/2006 |
| WO | WO-2006058221 A2 | 6/2006 |
| WO | WO-2006089292 A2 | 8/2006 |
| WO | WO-2006096756 A2 | 9/2006 |
| WO | WO-2007041648 A2 | 4/2007 |
| WO | WO-2007044705 A2 | 4/2007 |
| WO | WO-2007044836 A2 | 4/2007 |
| WO | WO-2007056516 A2 | 5/2007 |
| WO | WO-2007059207 A2 | 5/2007 |
| WO | WO-2008085521 A1 | 7/2008 |

OTHER PUBLICATIONS

Principles of practice of spine surgery by Vaccaro, et A1,; Mosby Press, Philadelphia, PA; 2003.
The epiphyses ring: a long forgotten anatomical structure with significant physiologicA1 function. Dar G, et A1. Spine (Phiia PA 1976), May 15, 2011;36 (11): 850-6.
Ozgur B.M., et al., "Extreme Lateral Interbody Fusion (XLIF): A Novel Surgical Technique for Anterior Lumbar Interbody Fusion," Spine Journal, 2006, vol. 6 (4), pp. 435-443.
Wohns R.N.W., et al., Day Surgery for Anterior Cervical Microdiskectomy: Experience with 75 Cases, Jul. 11, 2002, pp. 1-3.
Yerby S., et al., "The Effect of Cutting Flute Design on the Insertion and Pullout Properties of Self-tapping Bone Screws," Jul. 2, 2002, pp. 1-2.

* cited by examiner

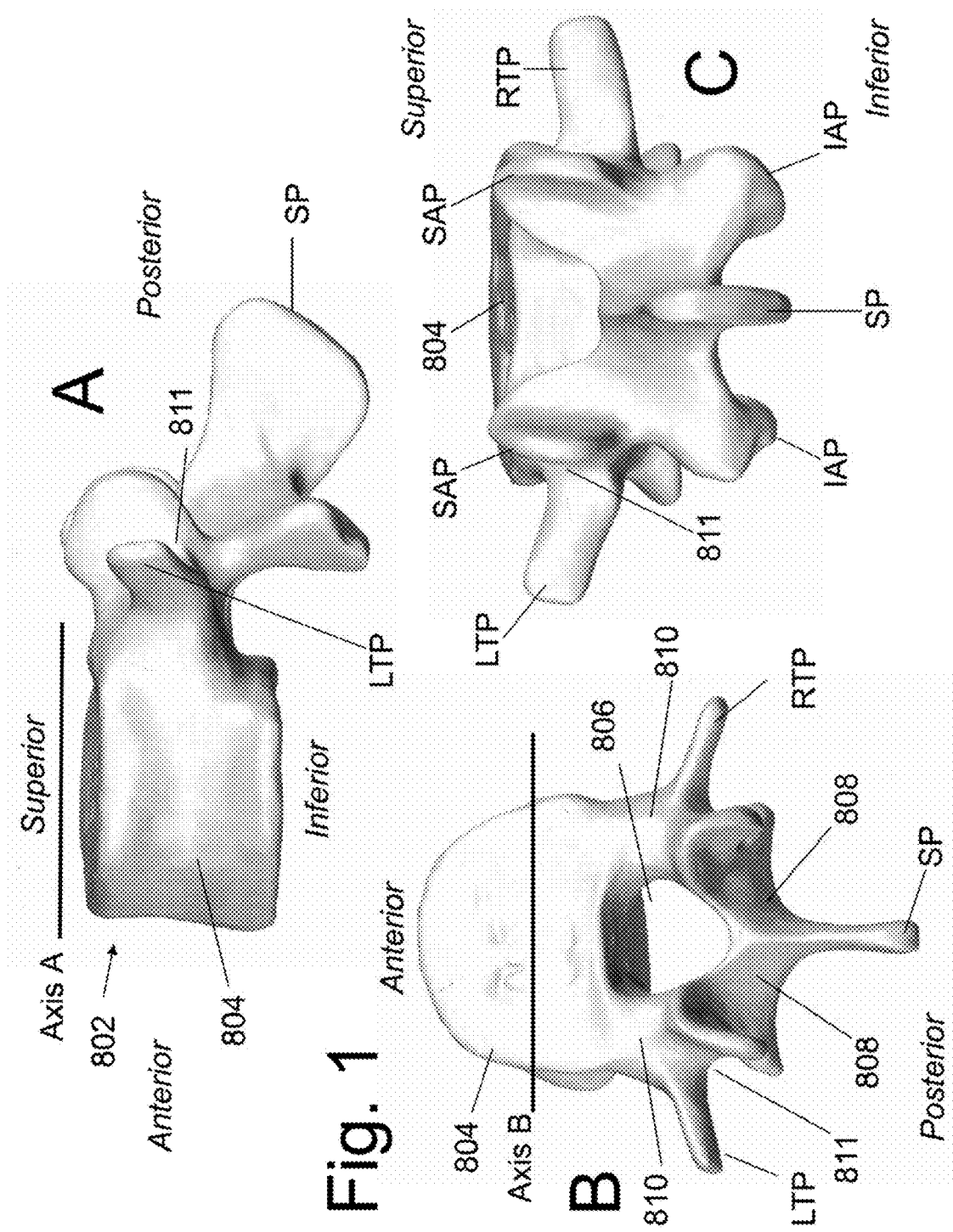

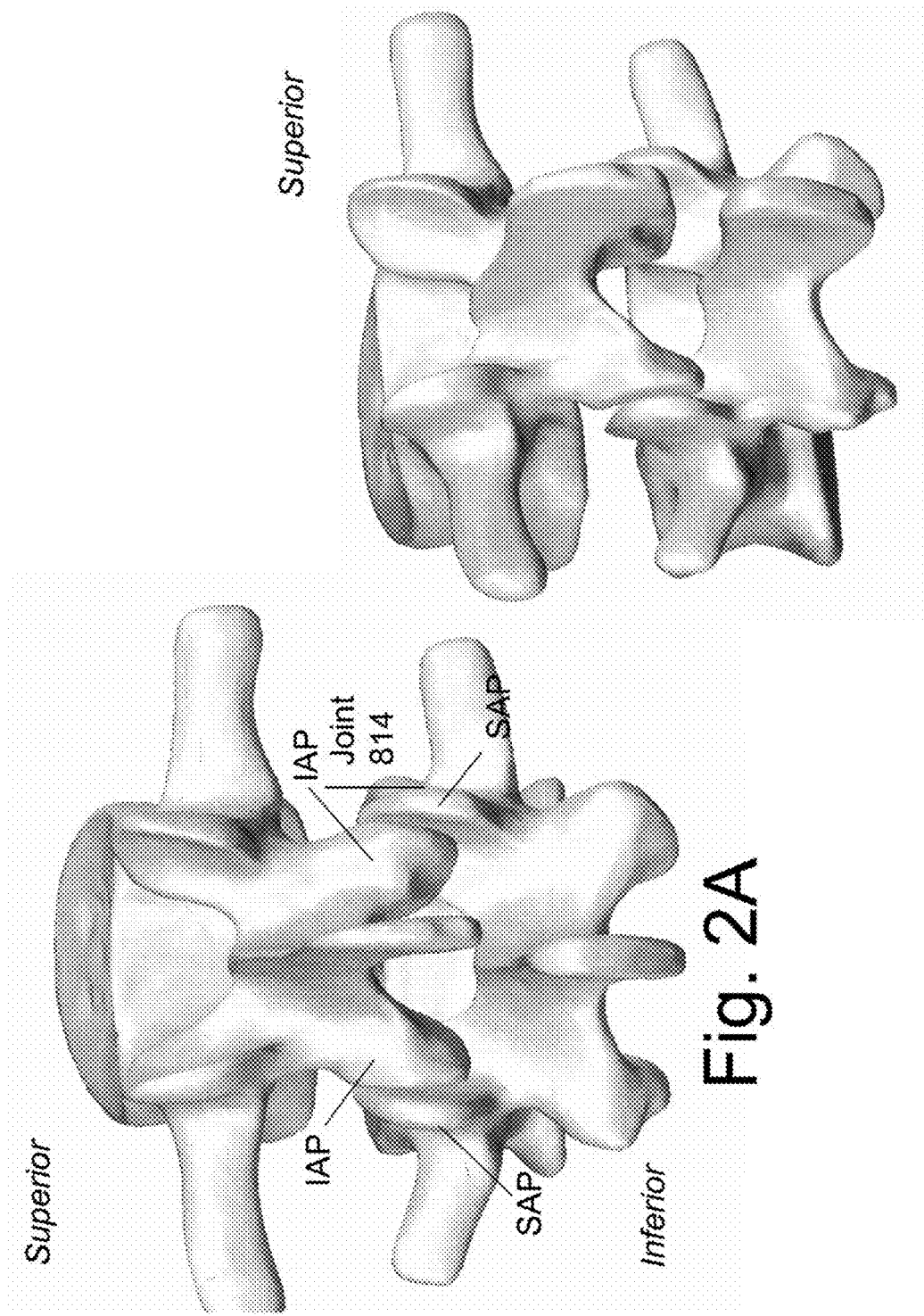

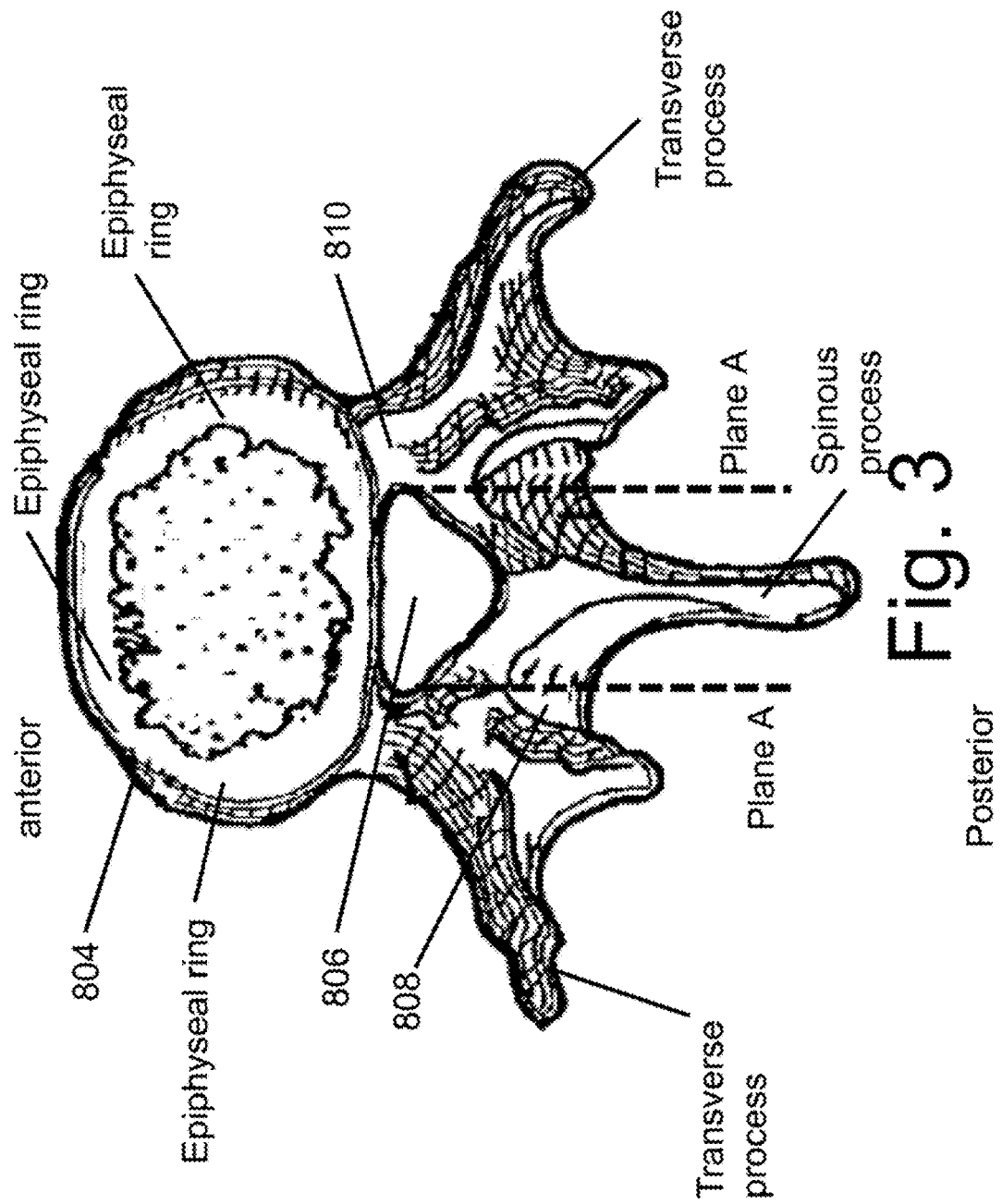

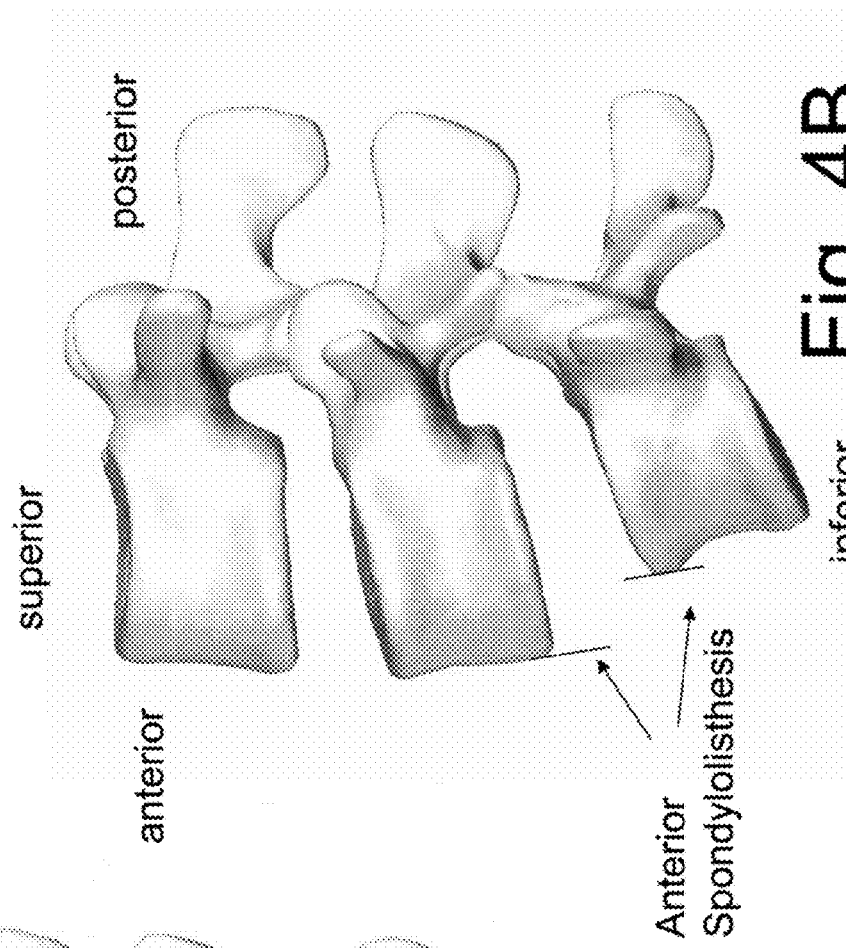
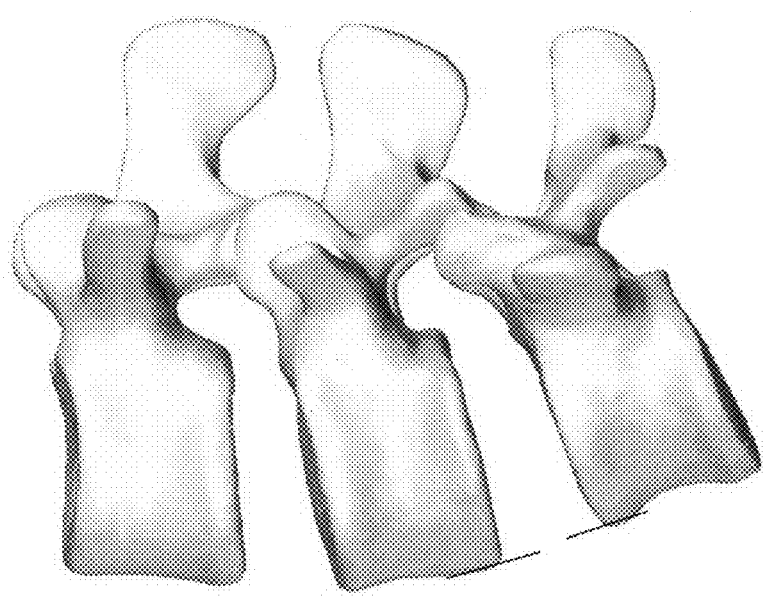
Fig. 4A
Fig. 4B

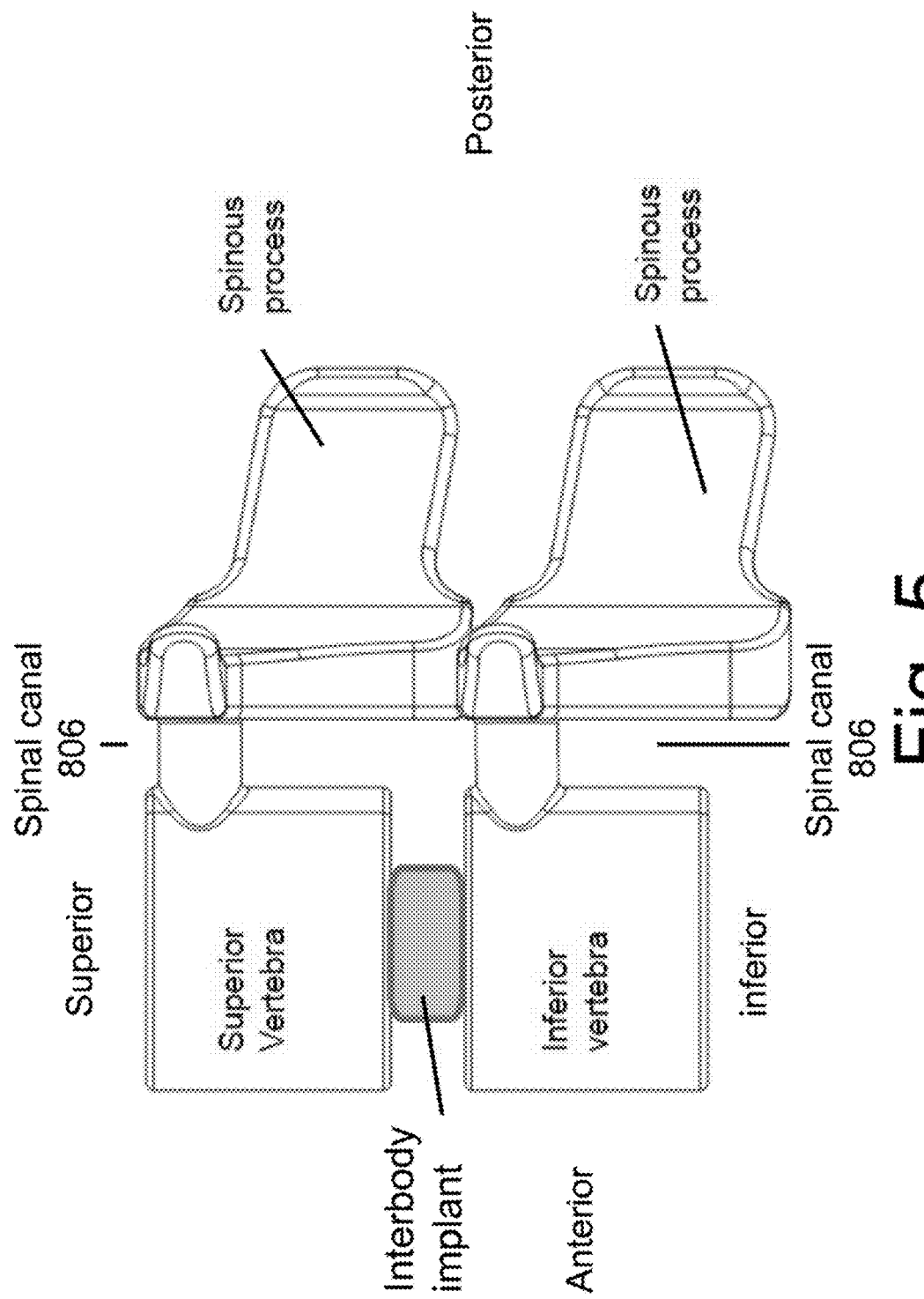

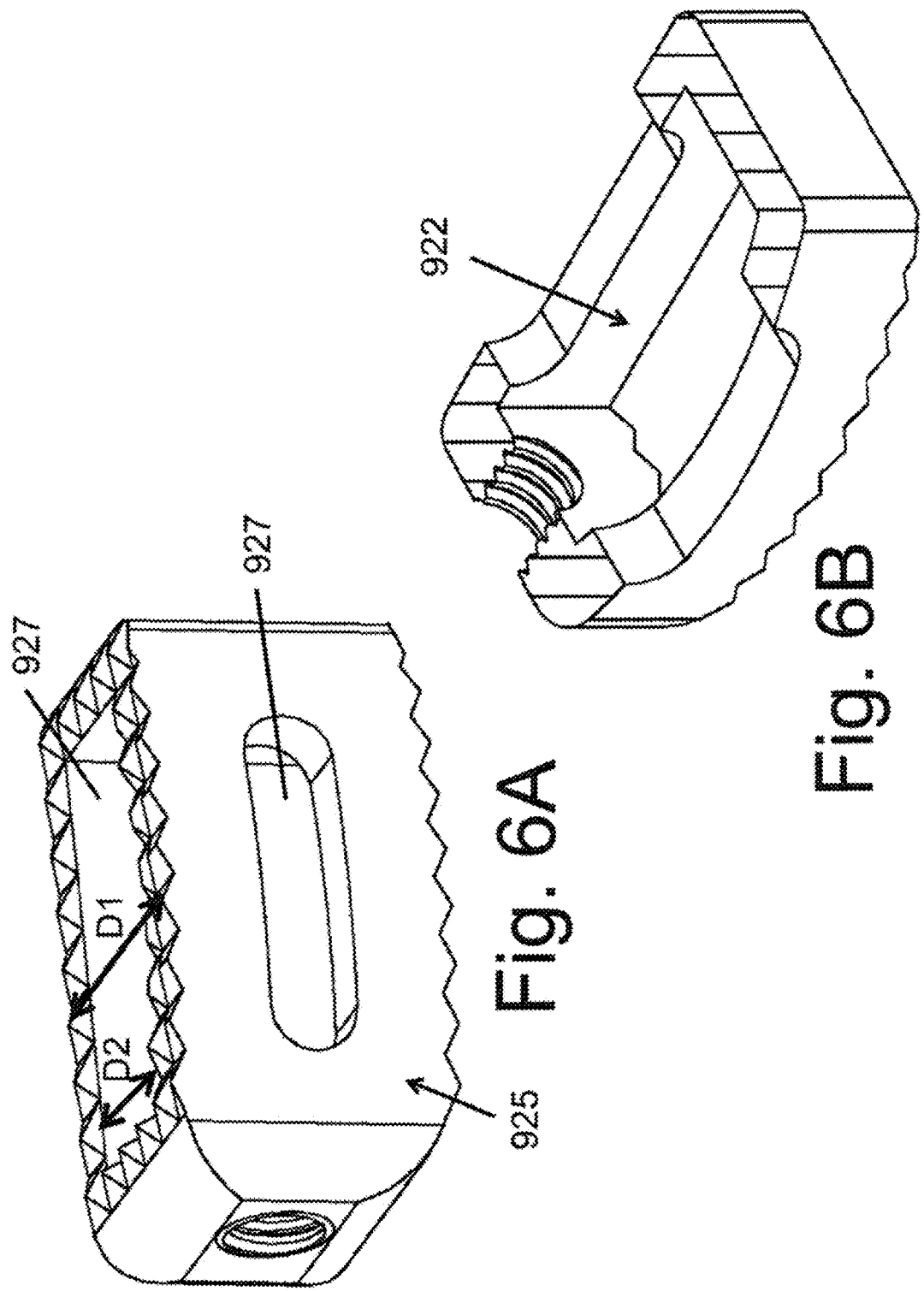

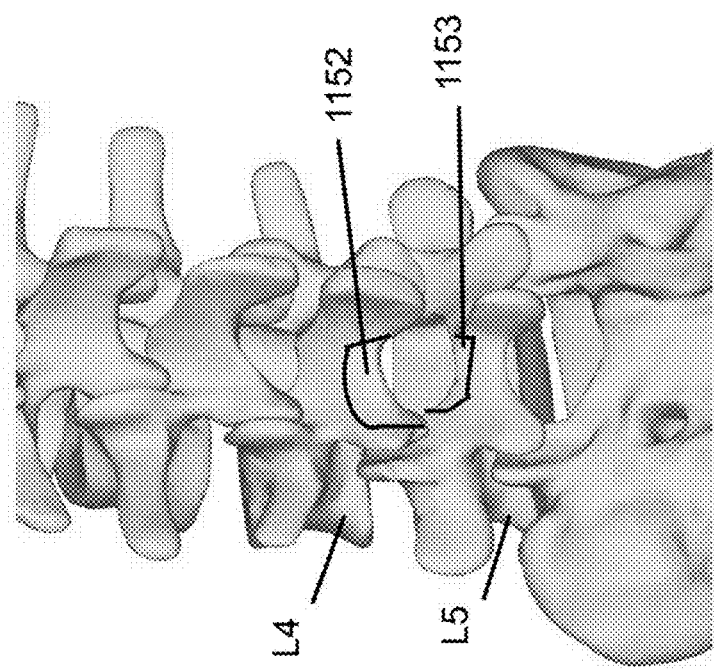
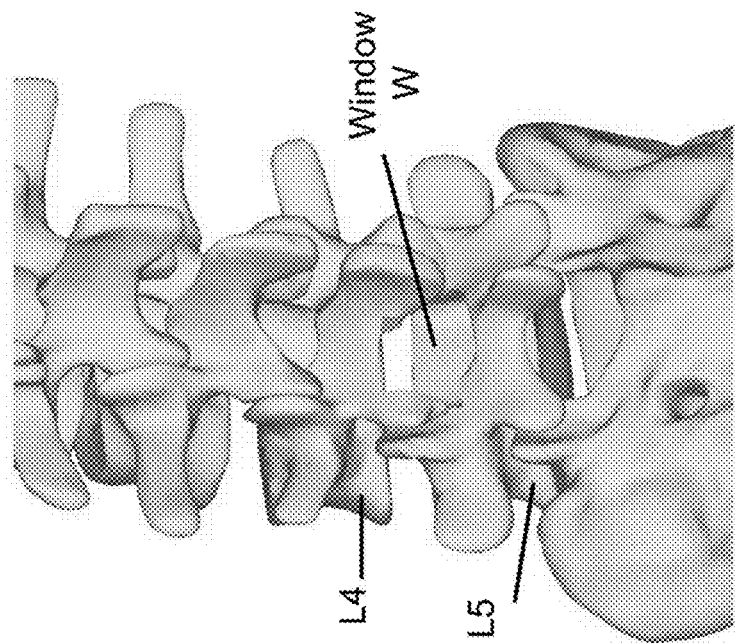
Fig. 7A
Fig. 7B

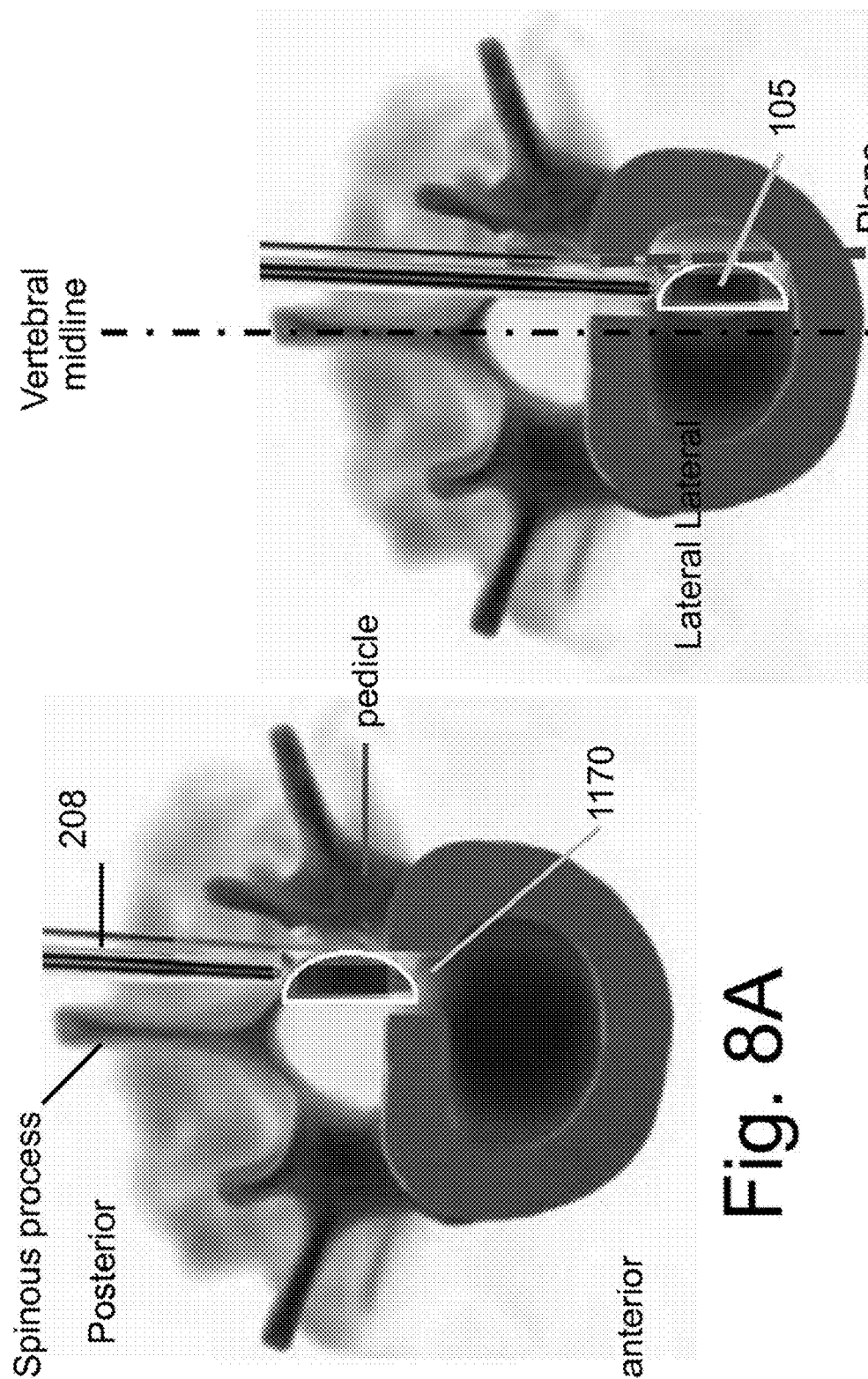

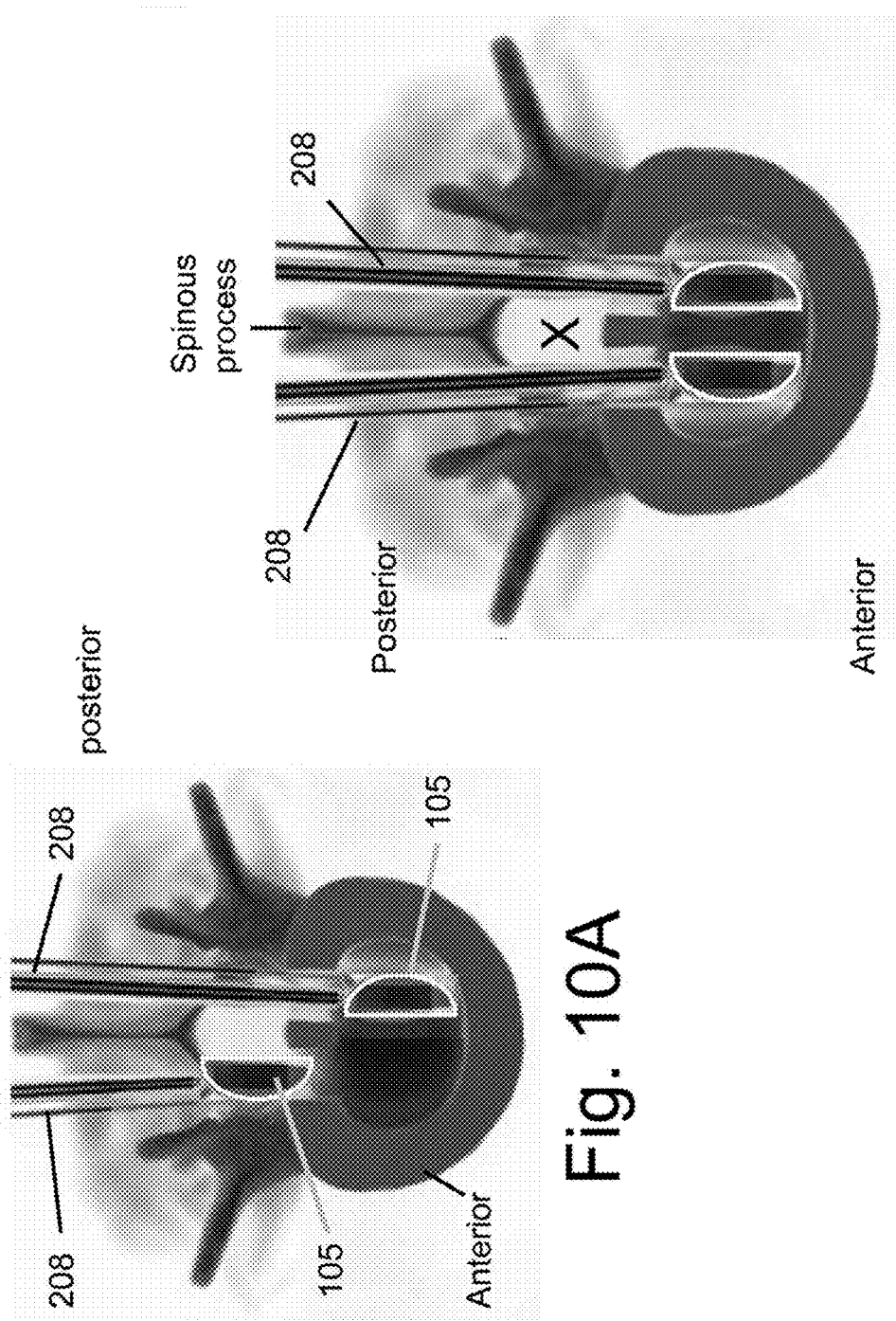

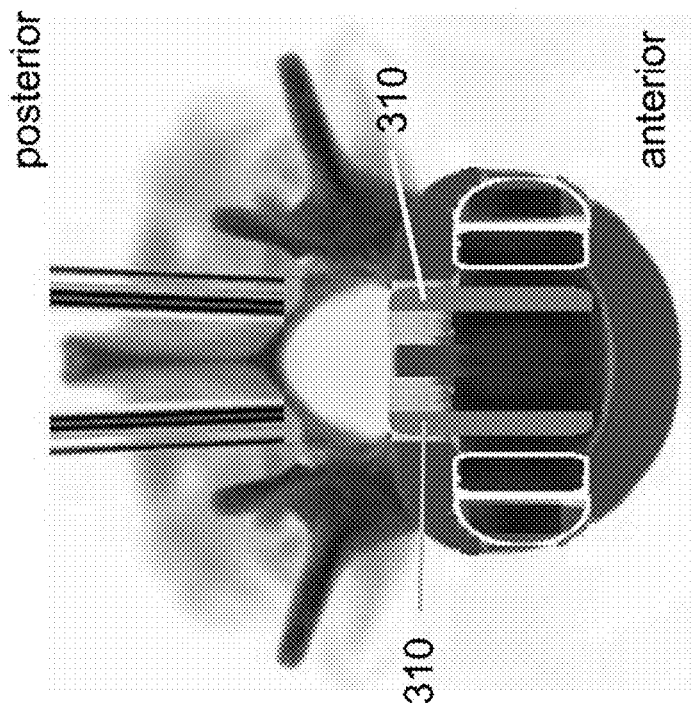
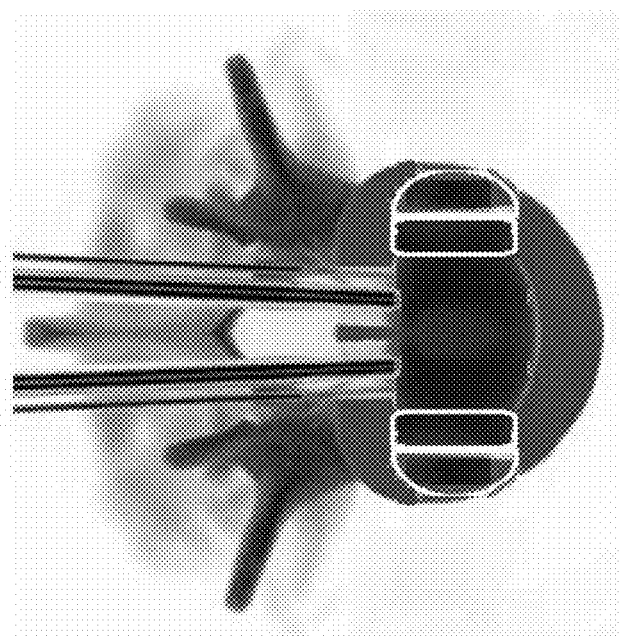
Fig. 12B
Fig. 12A

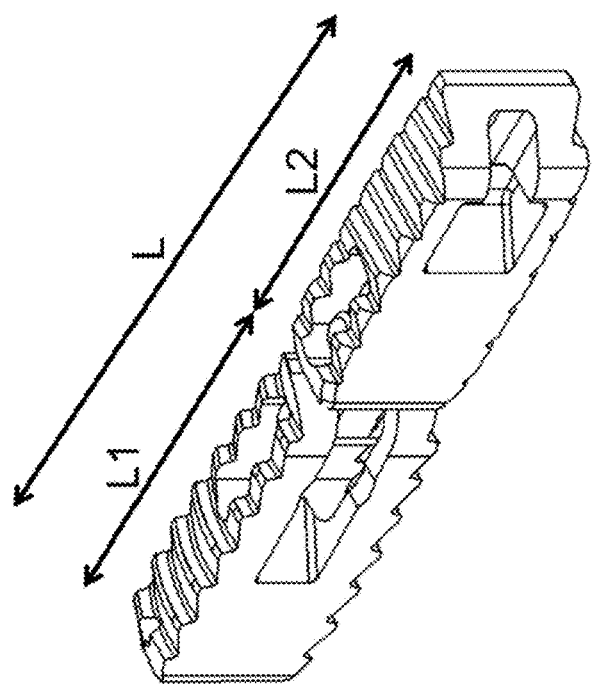
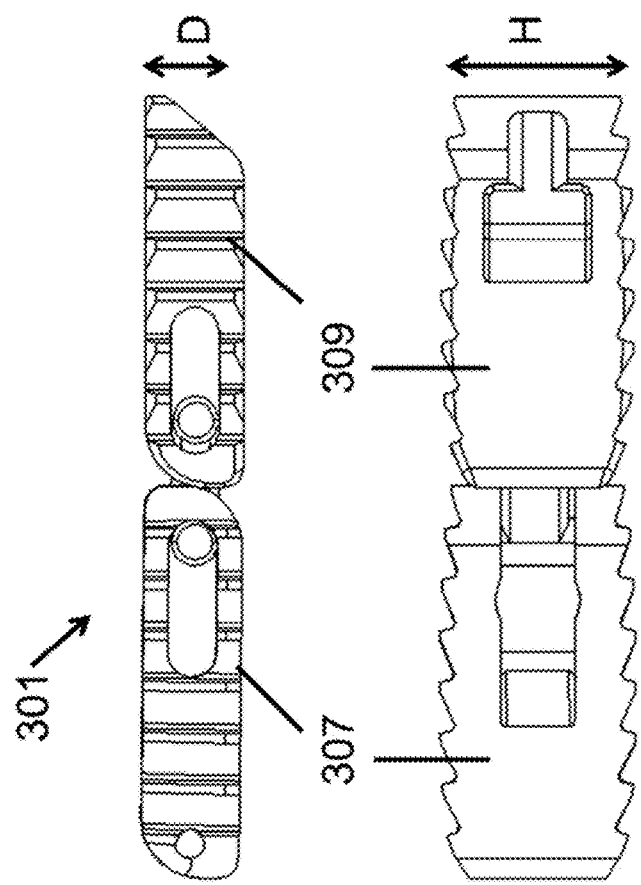
Fig. 14

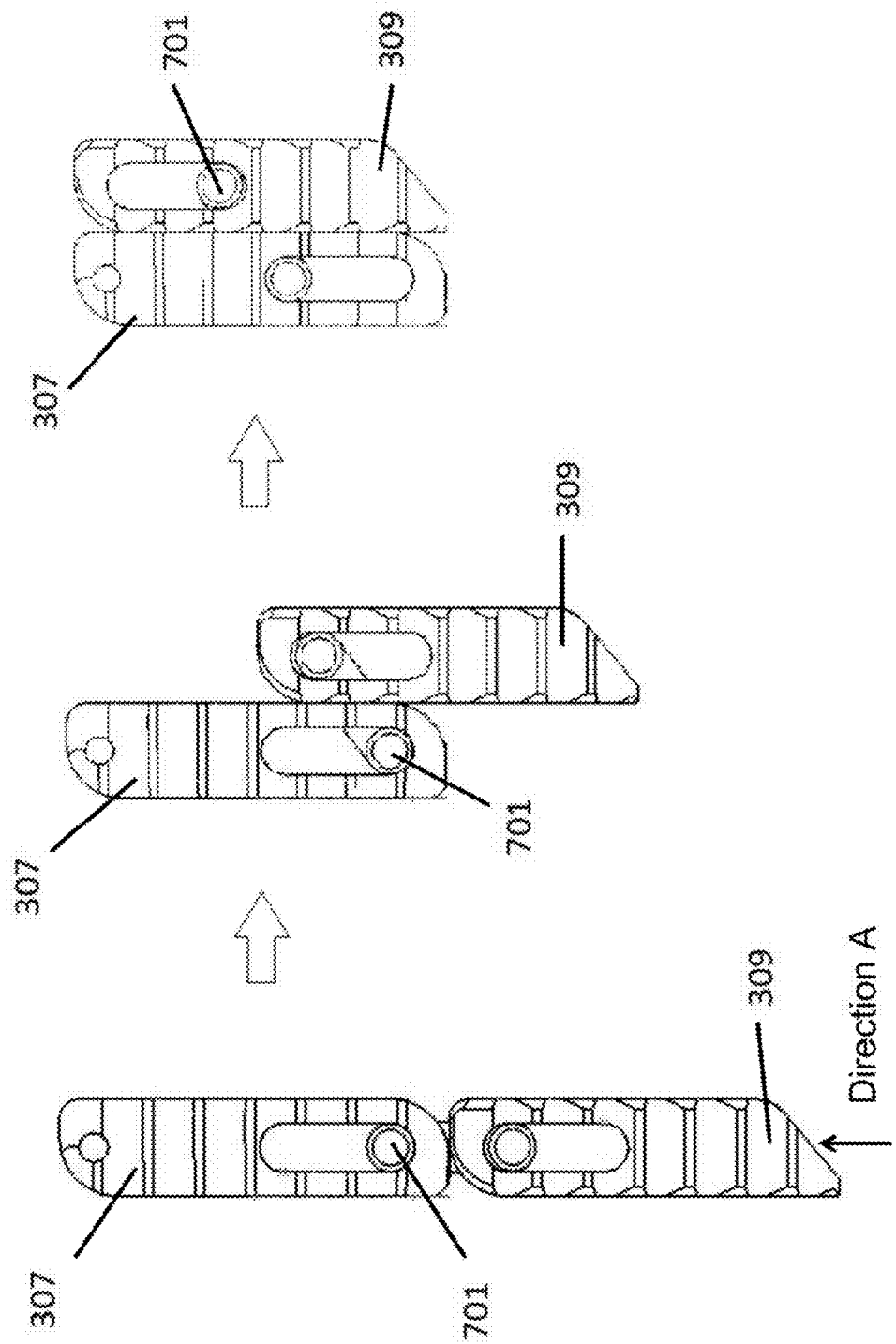

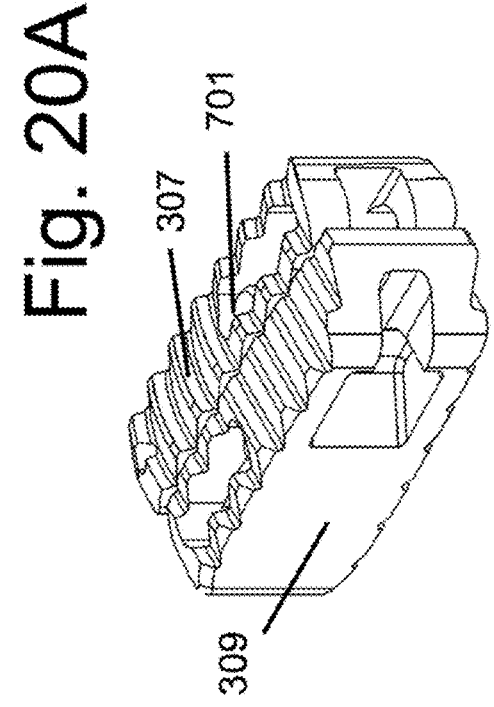
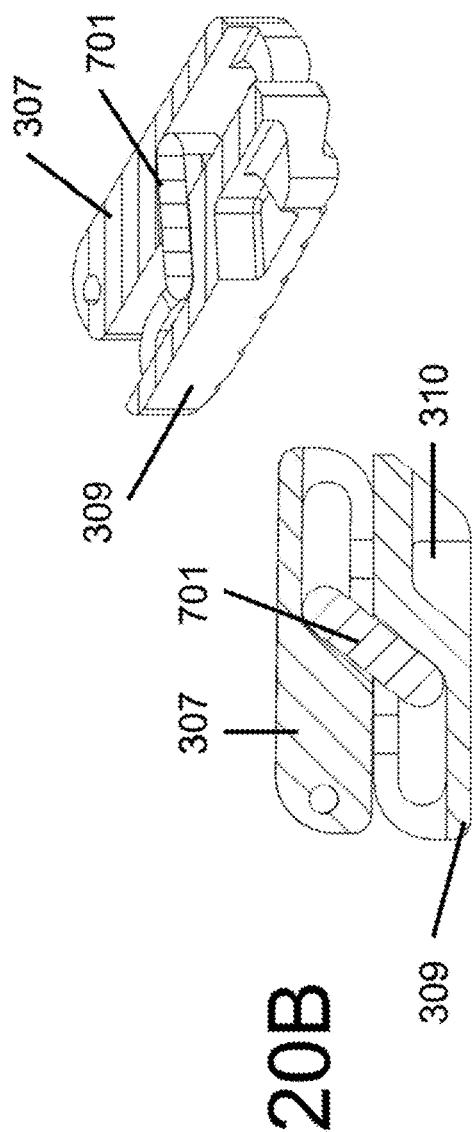
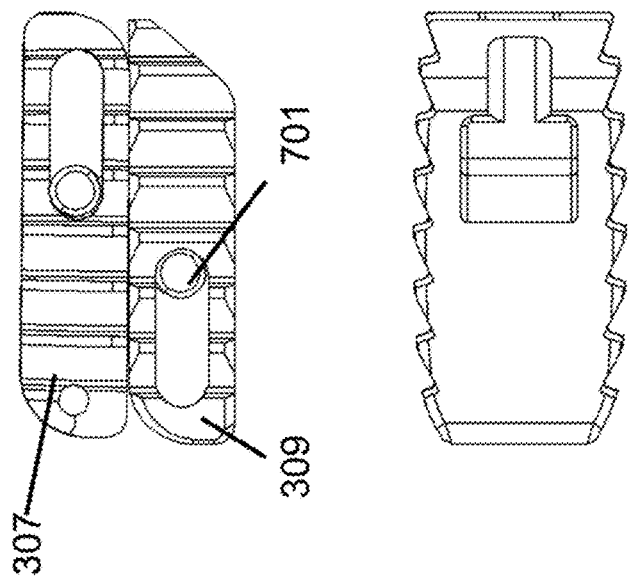
Fig. 20A
Fig. 20B

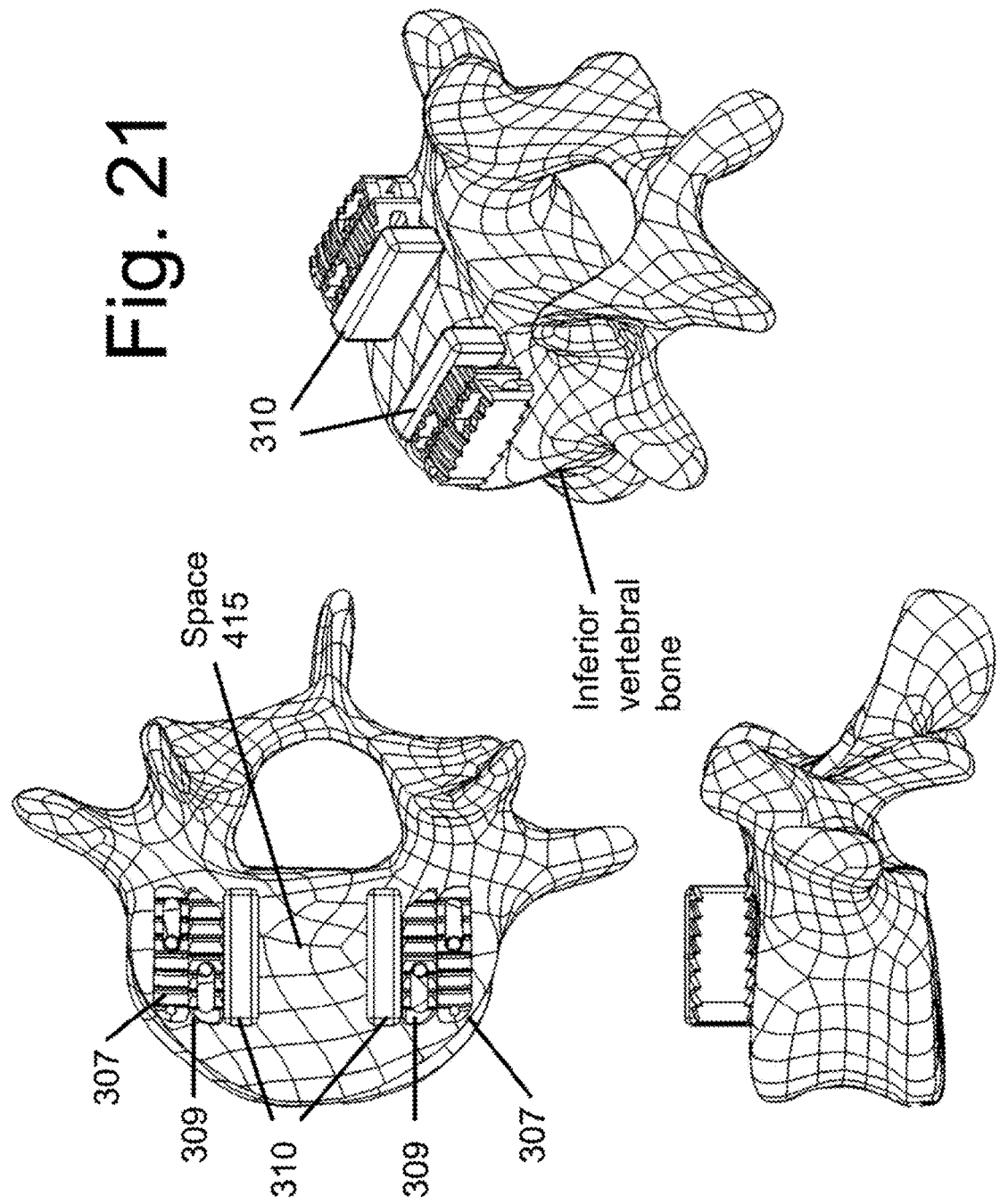

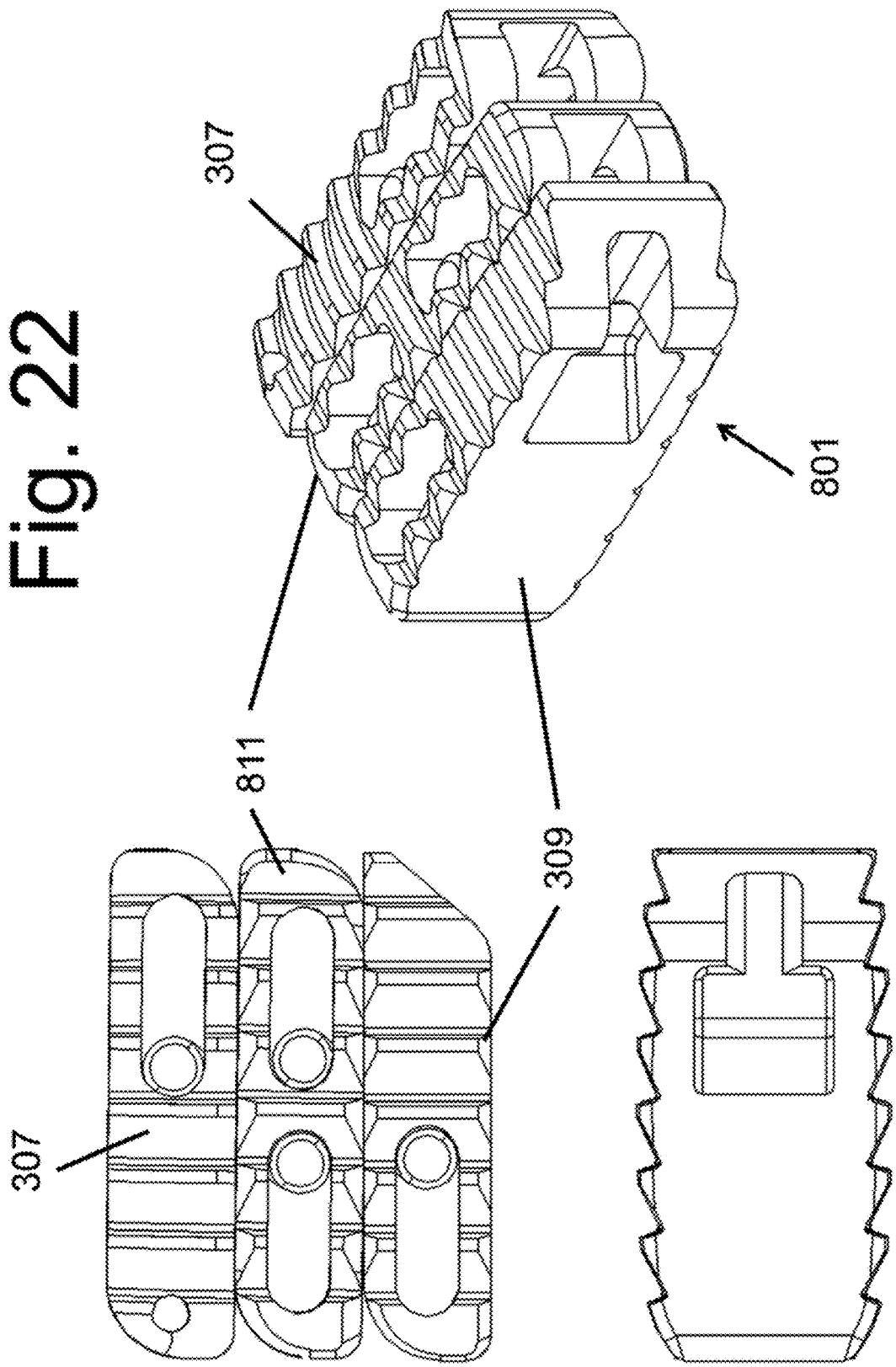

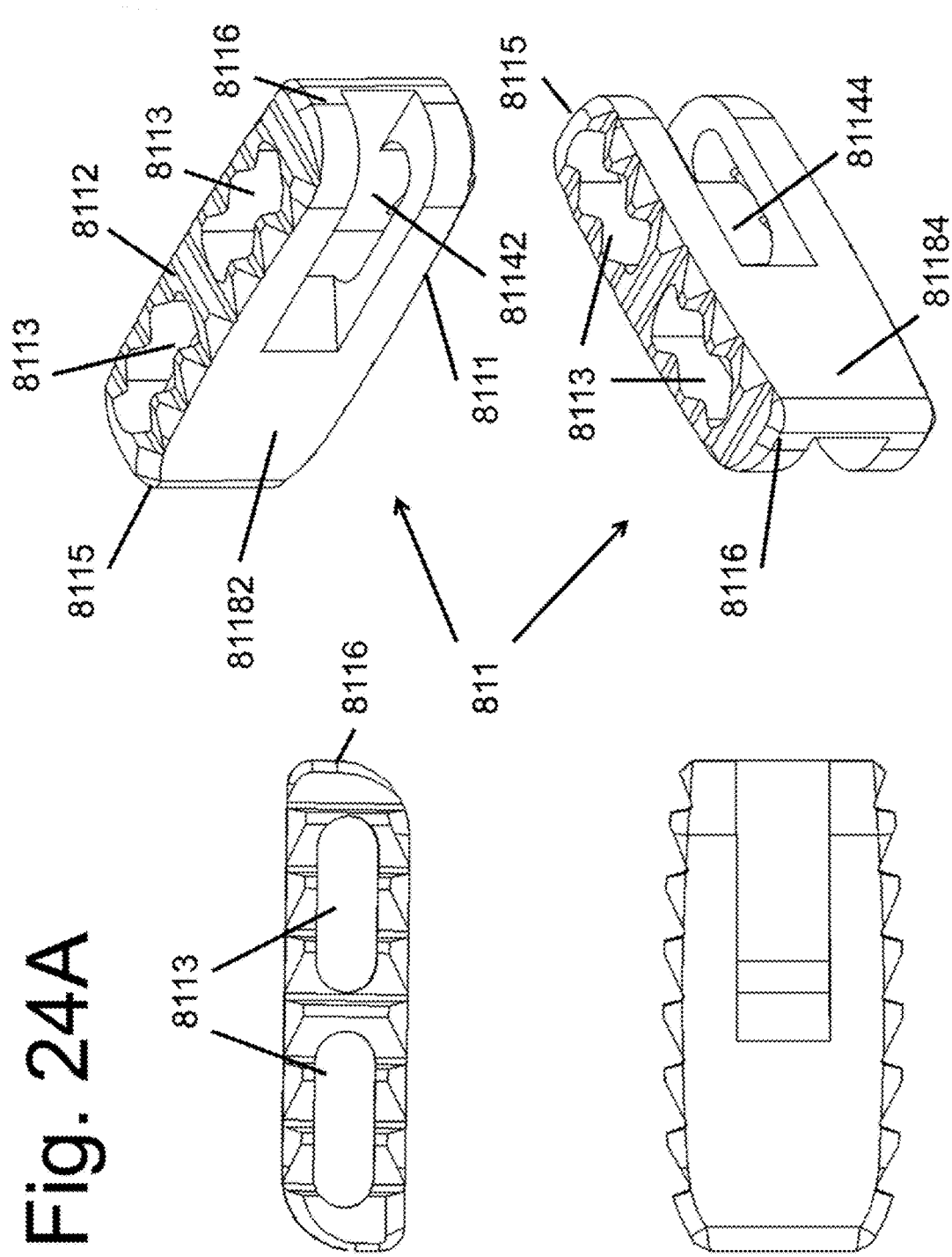

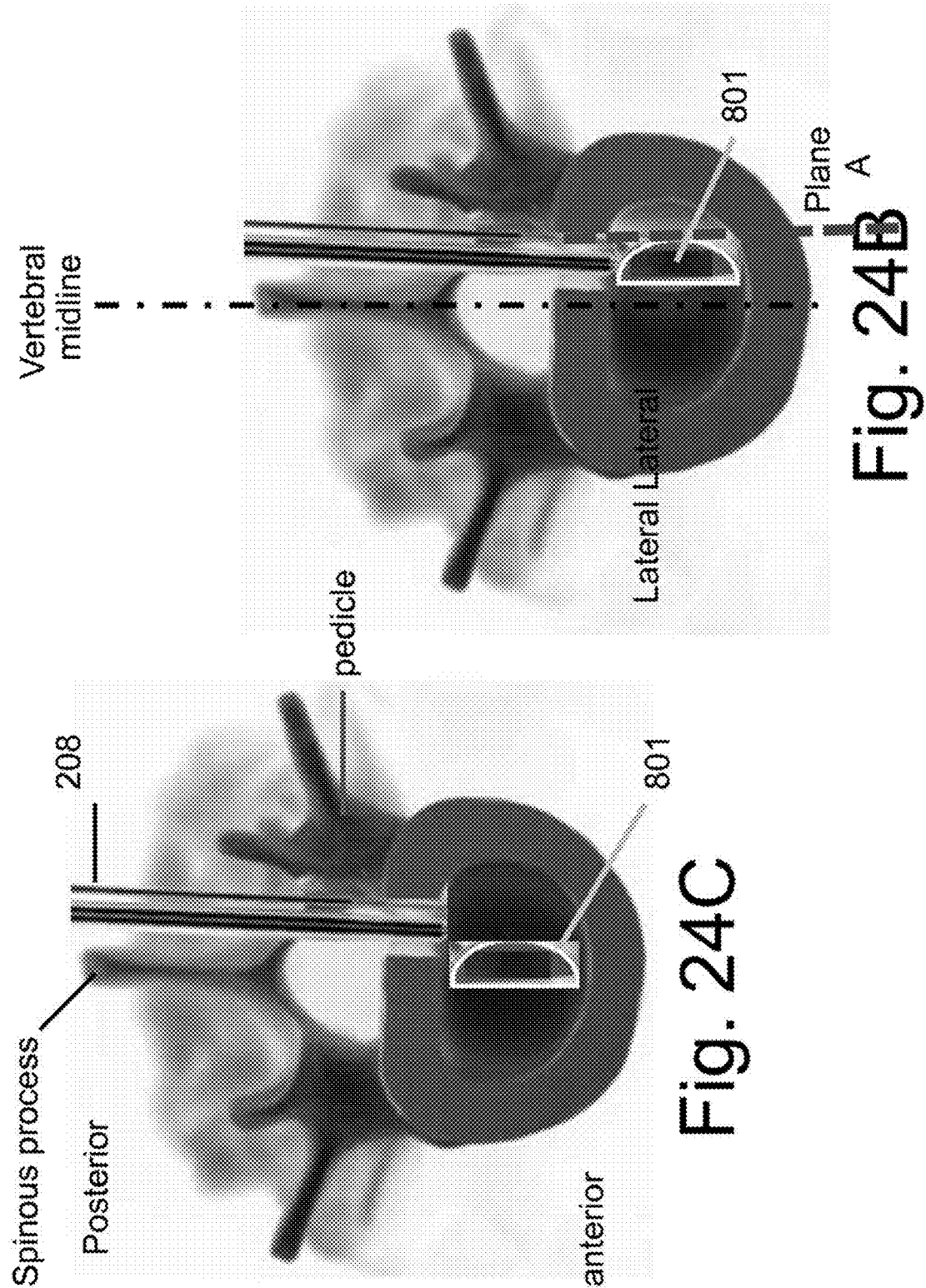

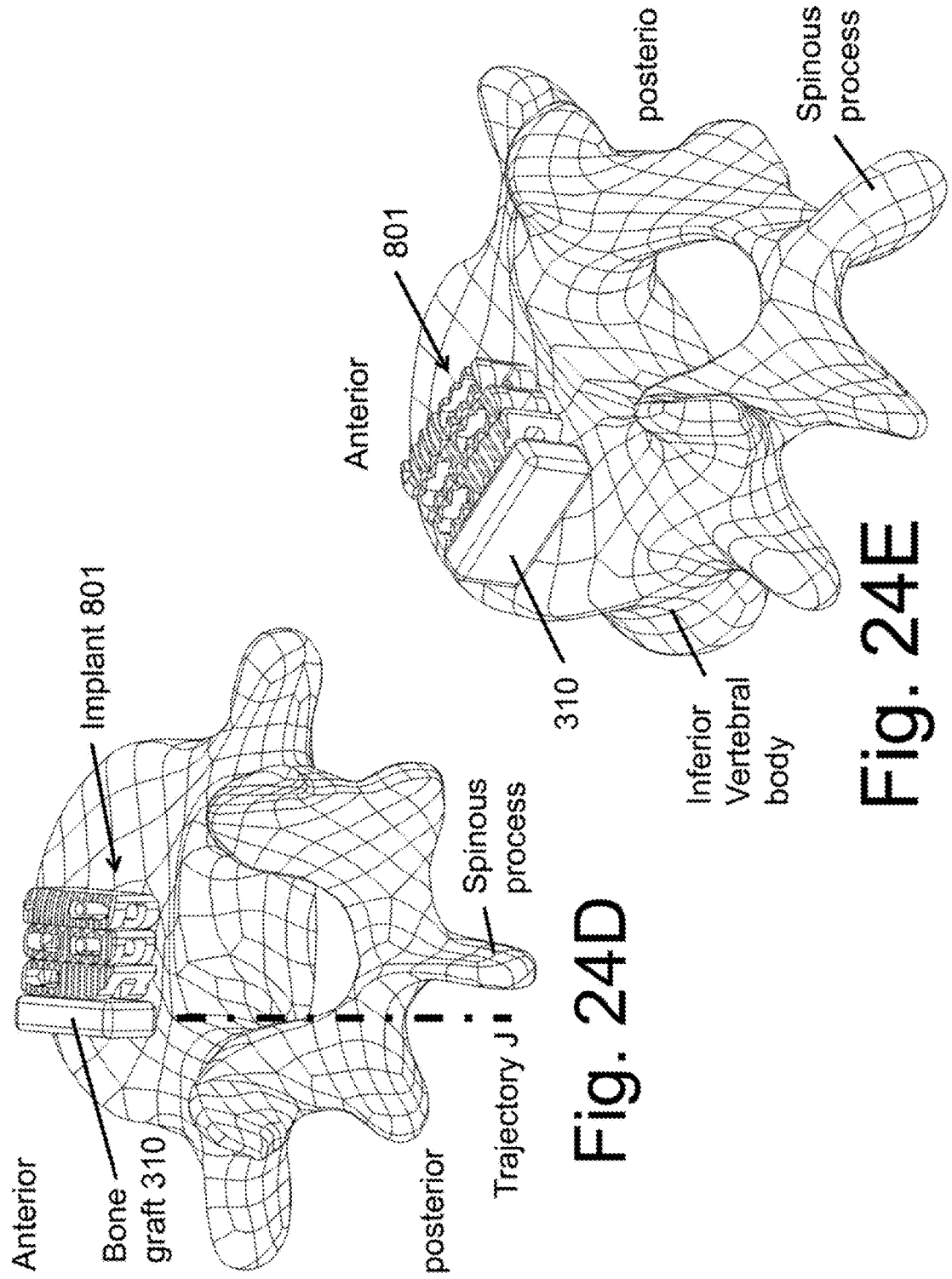

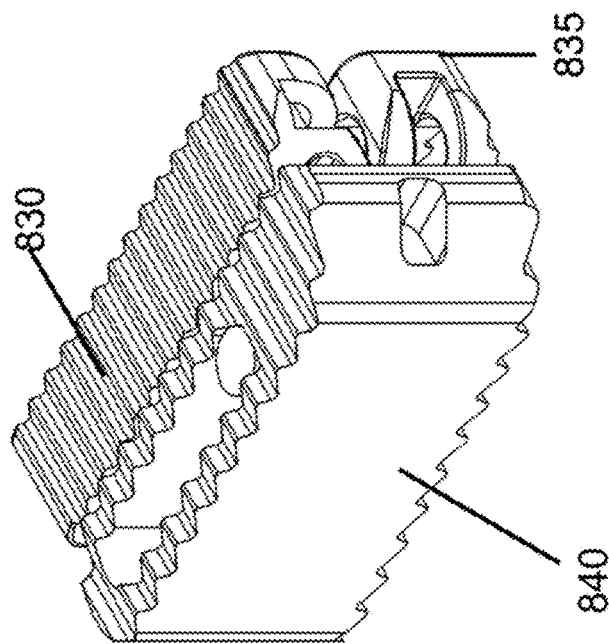
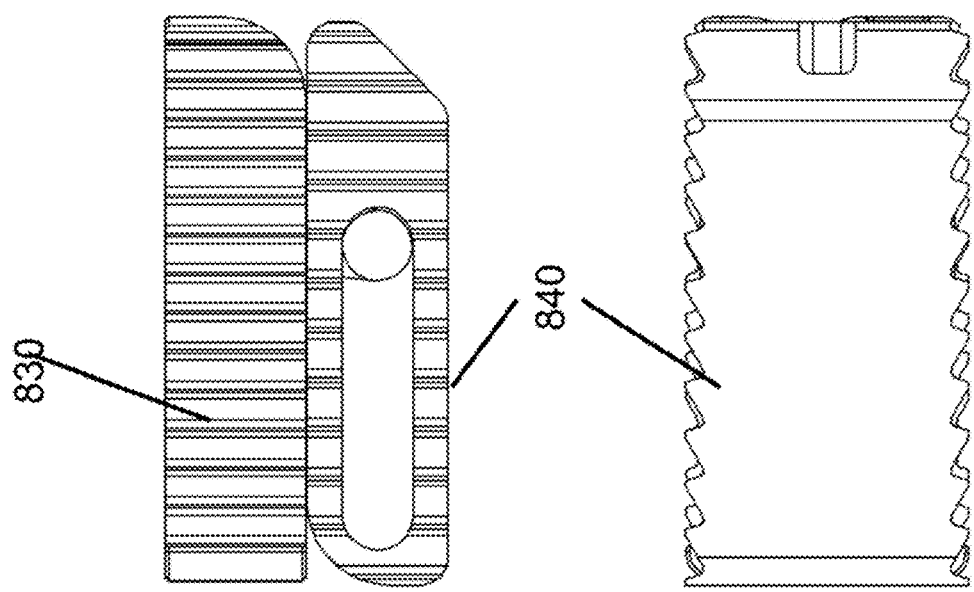
Fig. 32

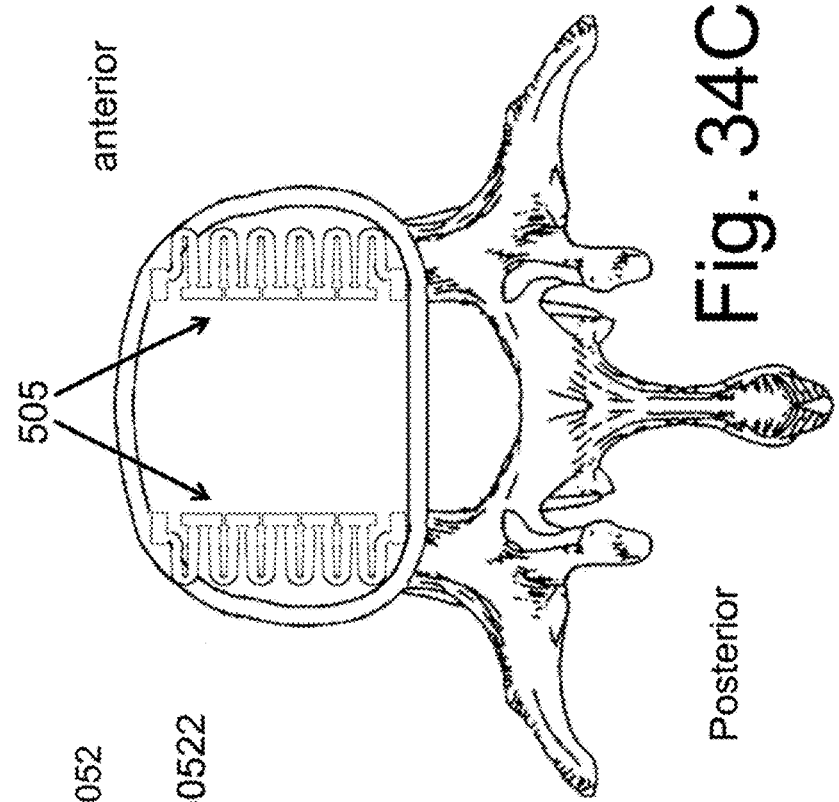
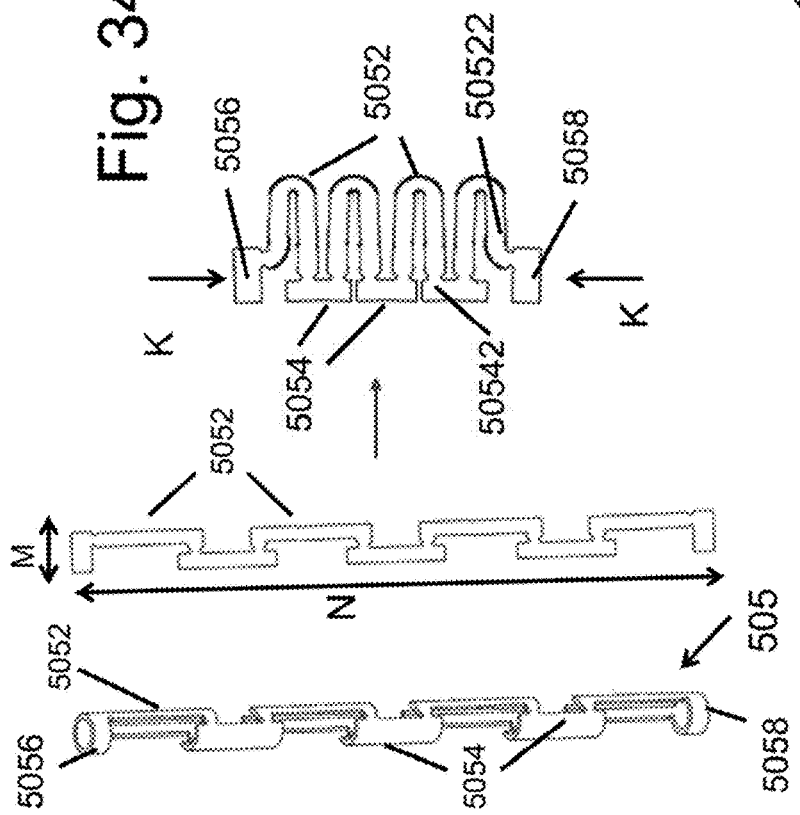
Fig. 34A
Fig. 34B
Fig. 34C

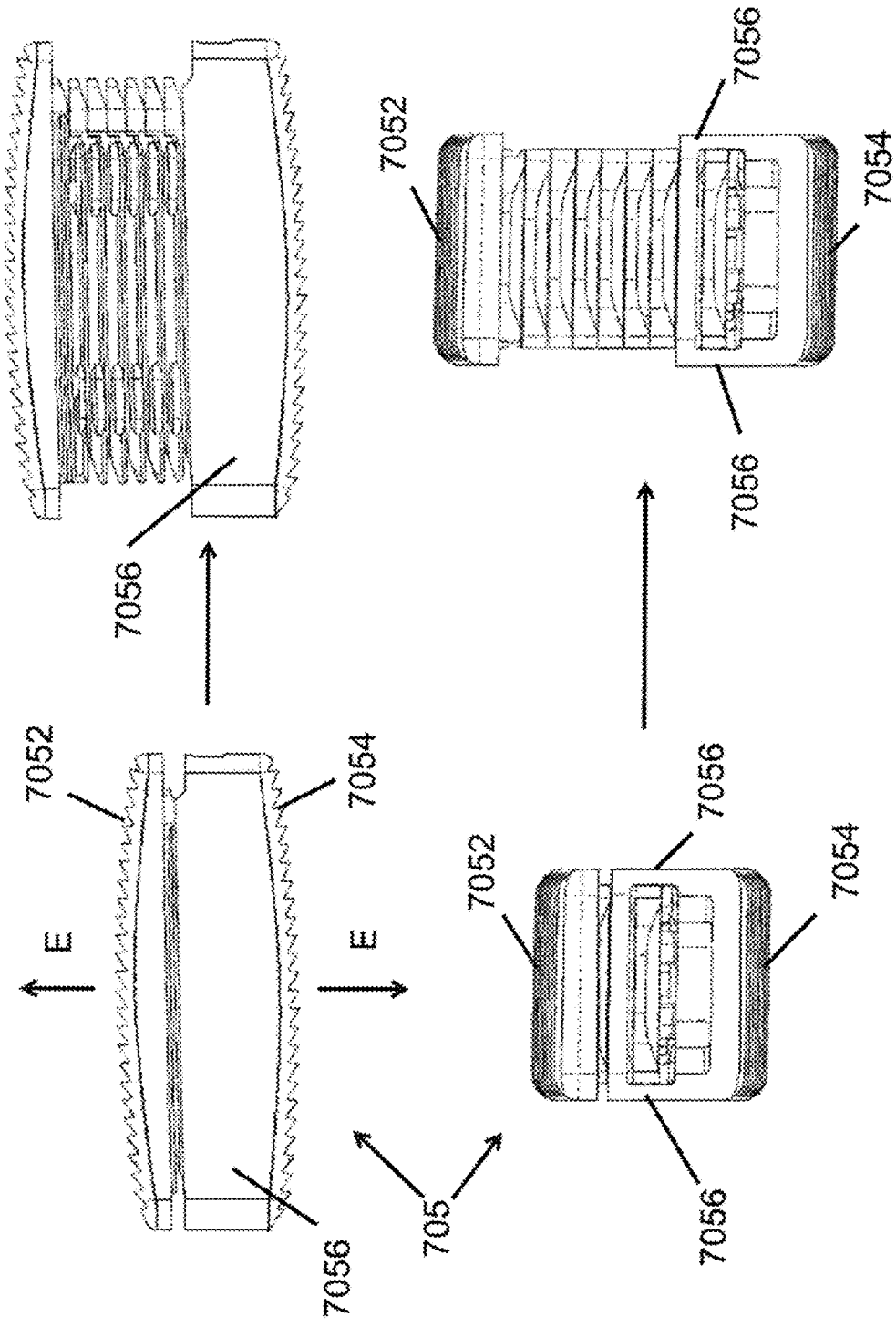

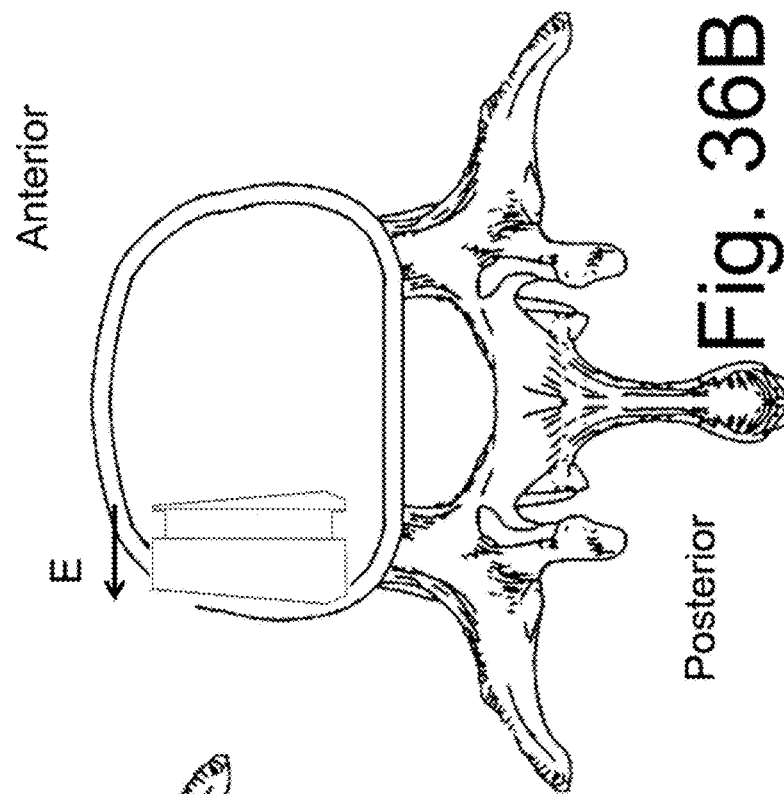
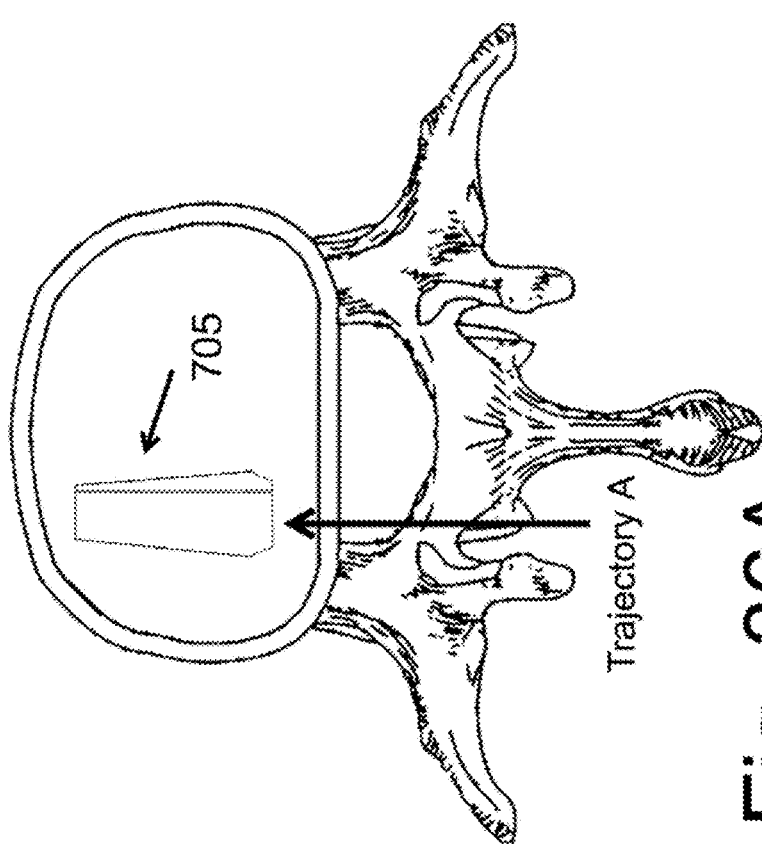

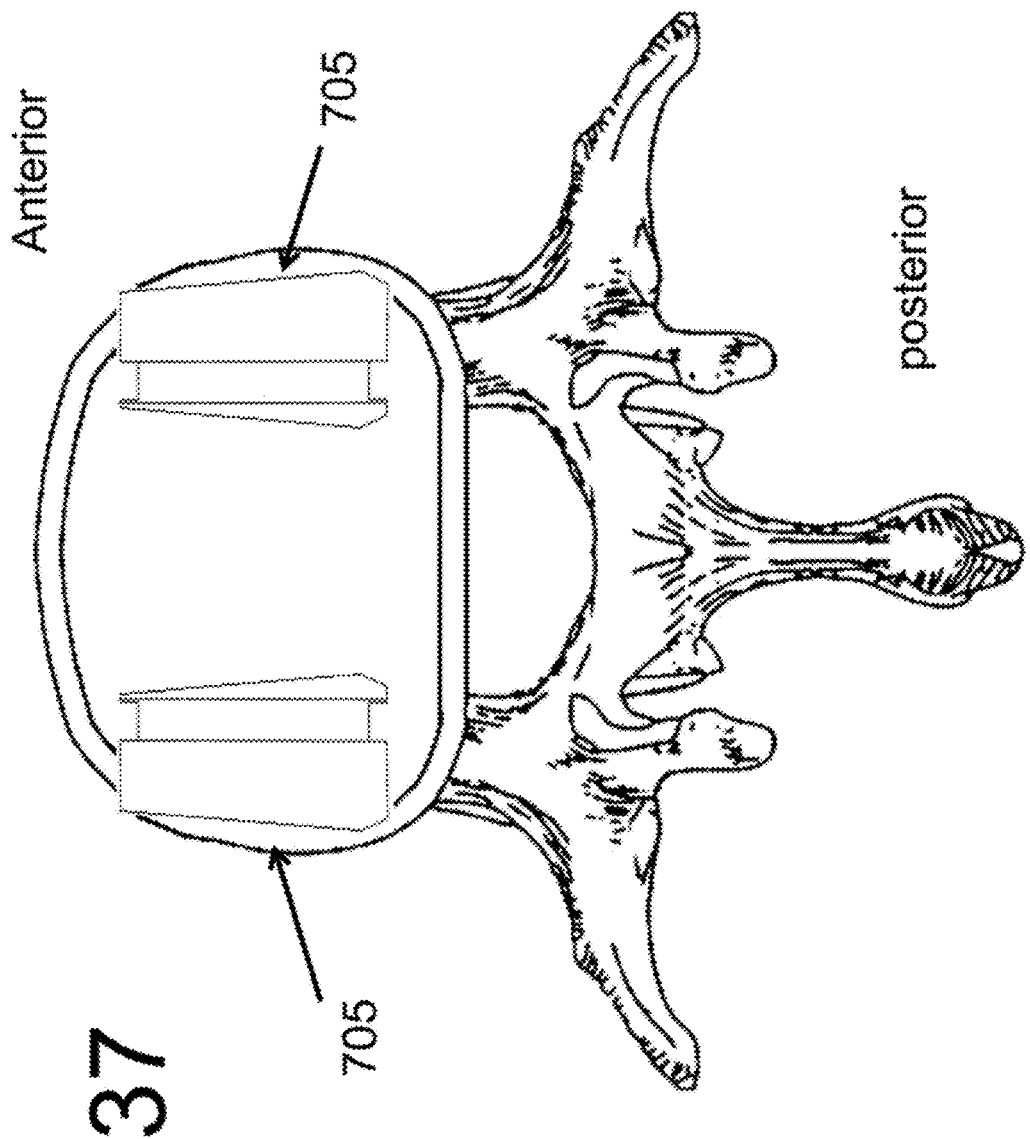

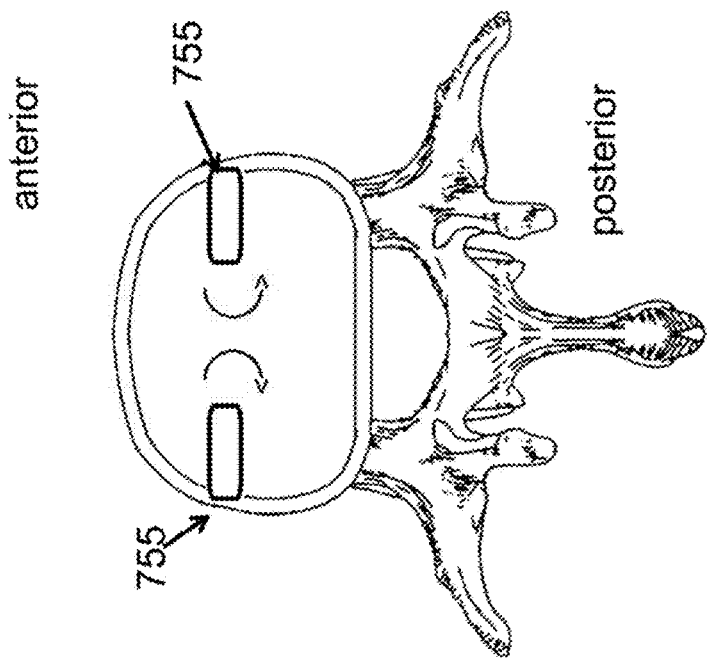
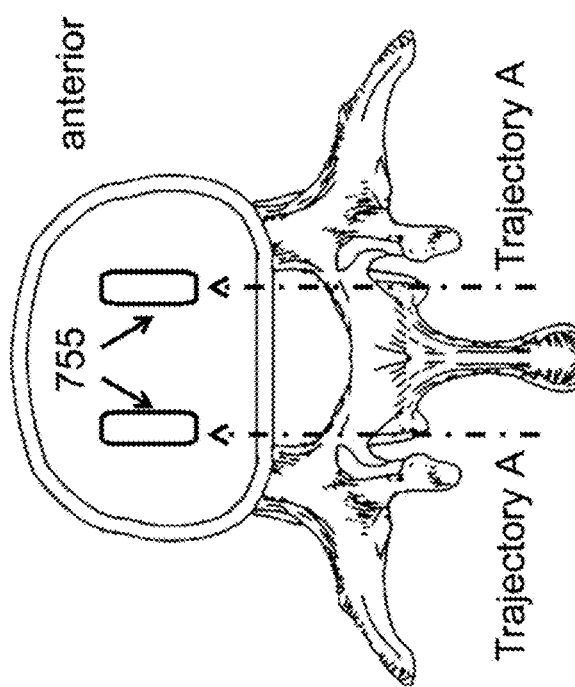
Fig. 38A
Fig. 38B

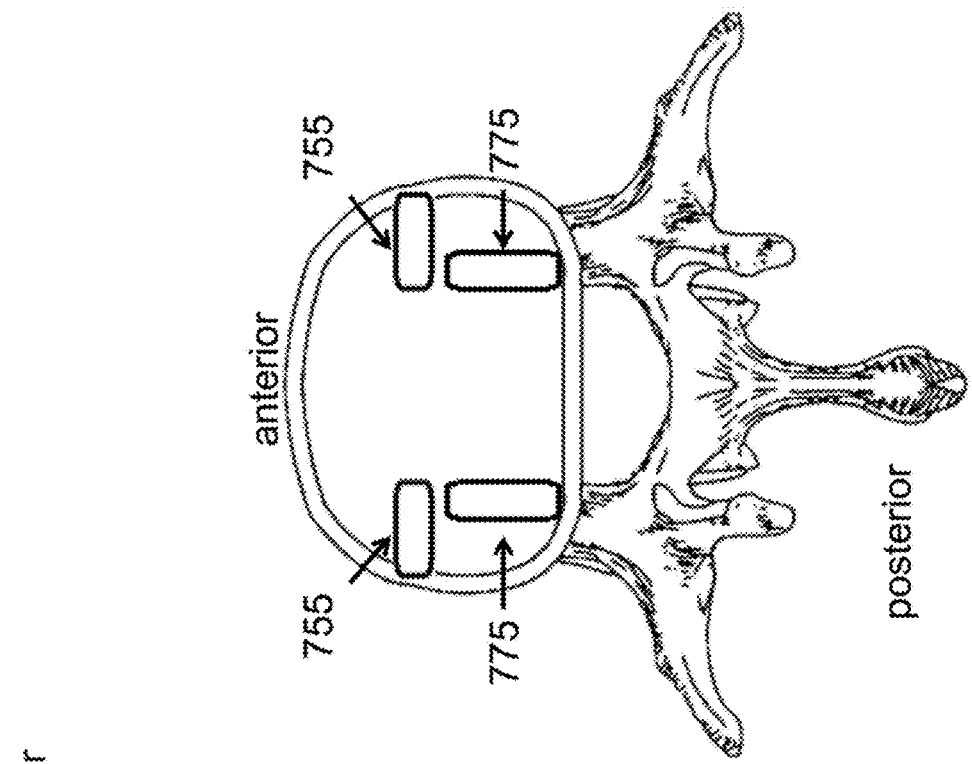
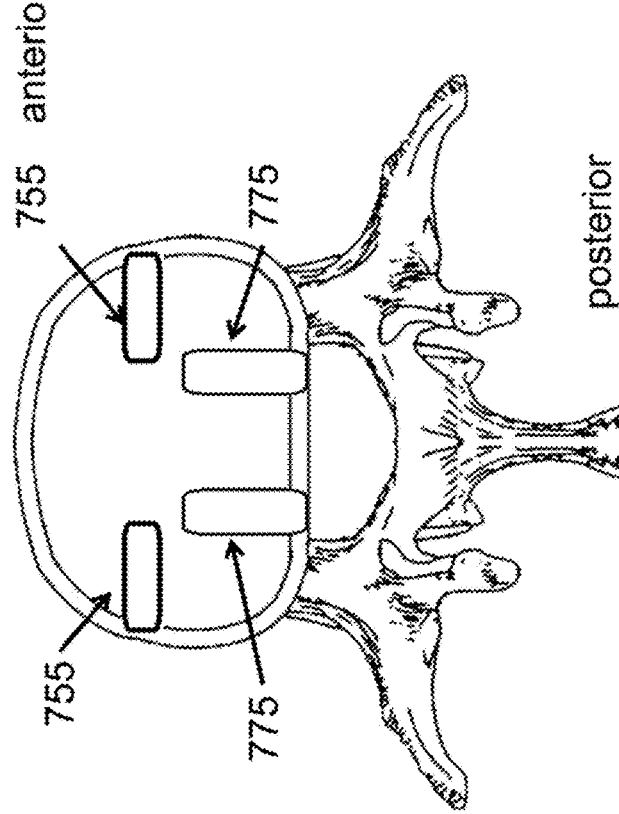
Fig. 39A
Fig. 39B

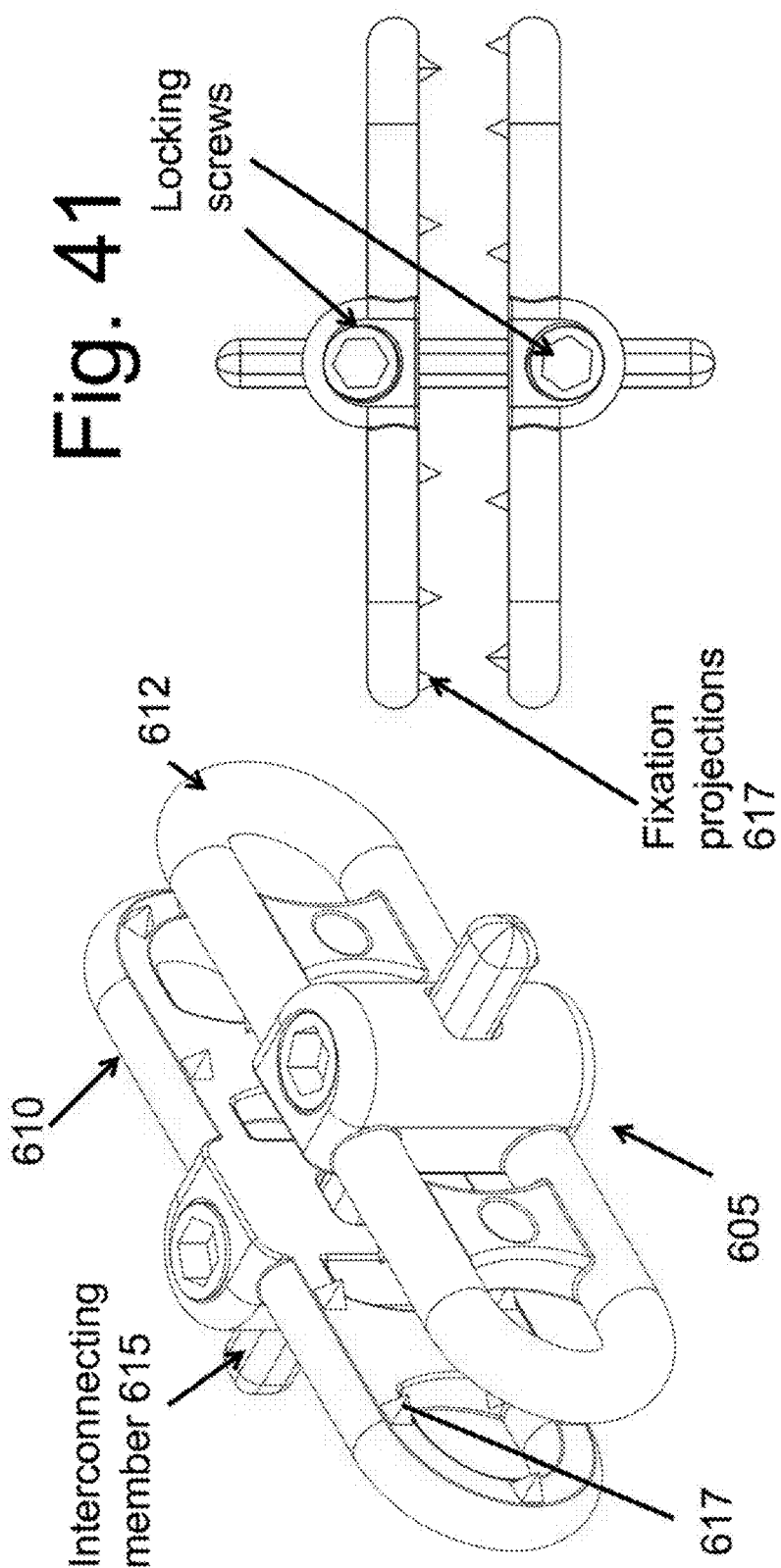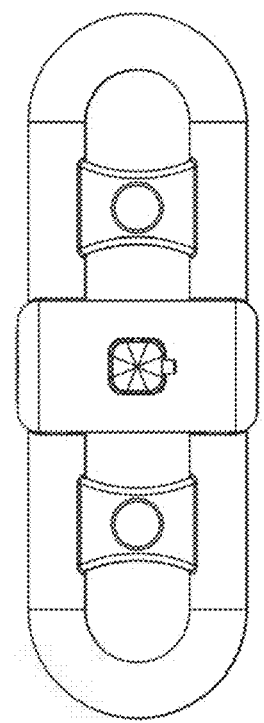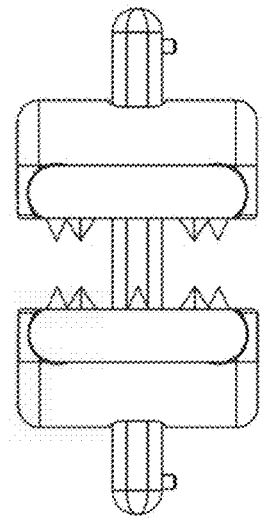
Fig. 41

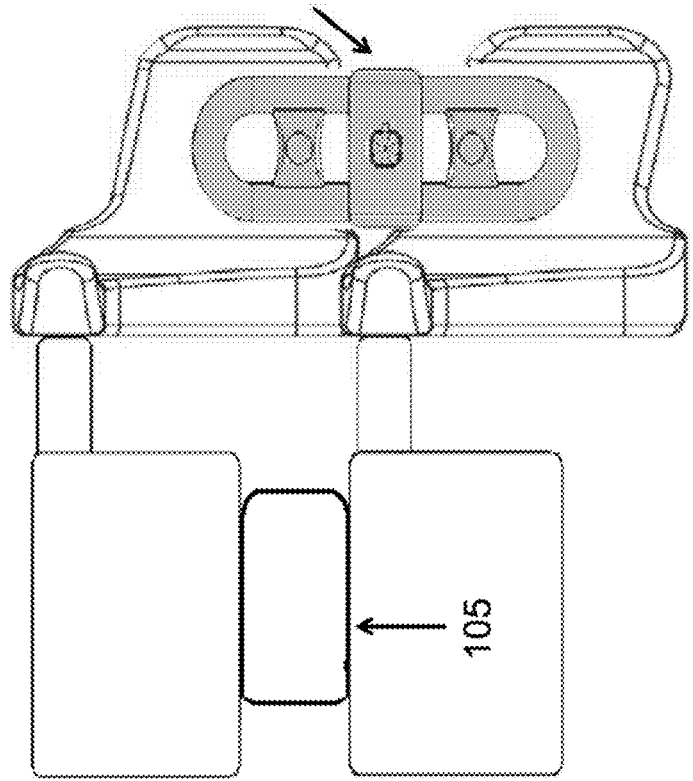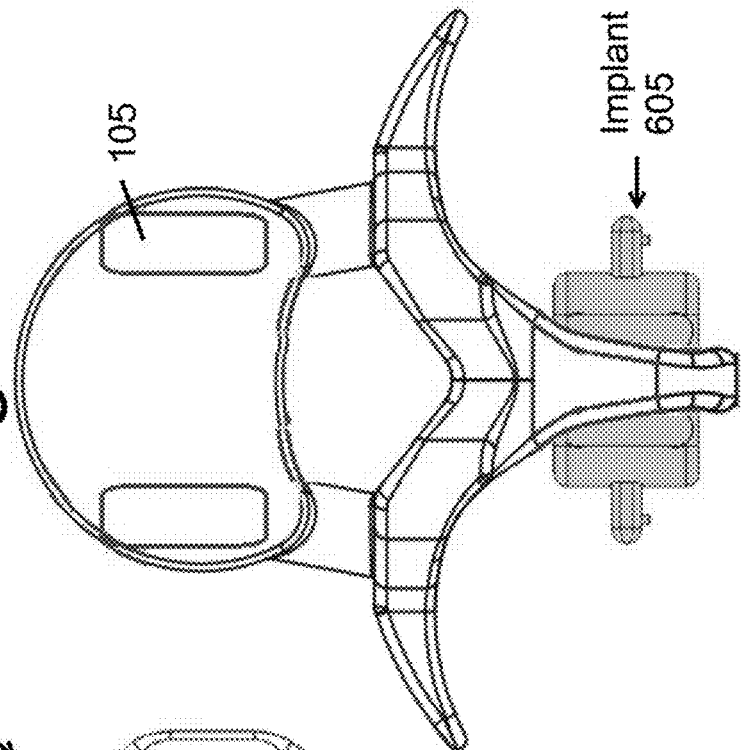

DEVICES AND METHODS FOR SPINAL STABILIZATION AND INSTRUMENTATION

PRIORITY

This application is a divisional of and claims priority to co-owned, co-pending U.S. patent application Ser. No. 13/797,586 filed on Mar. 12, 2013 and issuing as U.S. Pat. No. 9,320,617 on Apr. 26, 2016, which is incorporated herein by reference in its entirety and which claims priority to U.S. Provisional Patent Application Ser. No. 61/795,658 filed Oct. 22, 2012 of the same title, and to U.S. Provisional Patent Application Ser. No. 61/795,703 filed Oct. 23, 2012 of the same title, each of which is incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

The present disclosure relates generally to skeletal technology. In one exemplary, aspect, apparatus and methods are disclosed that permit stabilization of the bony elements of the skeleton. These devices permit adjustment and maintenance of the spatial relationship(s) between neighboring bones. Depending on the specifics of the design, the motion between skeletal segments may be immobilized completely or preserved.

2. Description of Related Technology

Whether from degenerative disease, traumatic disruption, infection or neoplastic invasion, alterations of the normal anatomical relationships between the spinal vertebras can cause significant pain, deformity and disability. Spinal disease is a major health problem and procedures that surgically reconstruct the spinal column have become common procedures in the industrialized world.

Vertebral fusion may be accomplished by using an anterior, lateral or posterior approach and each has particular advantages and drawbacks. Frequently, circumferential fusion of the unstable level with fixation of both the anterior and posterior aspect of the spine is desired. This requires that patients undergo a combination of the aforementioned approaches. The anterior or lateral approaches are used to insert the bone graft into the disc space between the adjacent vertebras while the posterior approach is used to place bone screws or similar fasteners that are used to immobilize the vertebral bodies.

Hence, it would be desirable to provide an improved interbody device.

SUMMARY

The present disclosure addresses the foregoing needs by disclosing, inter alia, apparatus and methods for providing spinal percutaneous delivery of an implant that can rigidly fixate the spinous process of a first superior bone and a second inferior bone of a functional spinal unit.

In a first aspect, a method for placement of at least two orthopedic implants into a target disc space of a subject is disclosed. In one embodiment, the method includes approaching a target disc space, said target disc space being bordered by a first and second bone segments; accessing said target disc space on a first side and creating a first entry point therein; accessing said target disc space on a second side and creating a second entry point therein; advancing a first implant placement instrument into said target disc space through said first entry point, said first implant placement instrument being coupled to a first implant; advancing a second implant placement instrument into said target disc space through said second entry point, said second implant placement instrument being coupled to a second implant; affixing said first implant placement instrument to said second implant placement instrument such that a region of interconnection between said first and second implant placement instruments is positioned outside of said target disc space; and actuating at least one of said first and second implant placement instruments to displace a first one of said at least two implants away from a second one of said at least two implants, said displacement causing at least one of said at least two implants to be positioned onto a region of said target disc space.

In another embodiment, the method includes: (i) approaching a posterior aspect of the target disc space, the target disc space being bordered by a superior and an inferior bone segment, (ii) accessing the posterior aspect of the target disc space lateral to a thecal sac structure on an ipsilateral side and creating an entry point therein, (iii) accessing the posterior aspect of the target disc space lateral to a thecal sac structure on a contra-lateral side and creating an entry point therein, (iv) advancing a first implant placement instrument into the target disc space through the ipsilateral entry point, the first implant placement instrument being coupled to a first implant, (v) advancing a second implant placement instrument into the target disc space through the contralateral entry point, the second implant placement instrument being coupled to a second implant, (vi) rigidly affixing the first implant placement instrument to the second implant placement instrument, such that a region of interconnection between the first and second implant placement instruments is positioned outside of the target disc space, and (vii) actuating at least one of the first and second implant placement instruments to displace a first one of the at least two implants away from a second one of the at least two implants, the displacement causing at least one of the at least two implants to be positioned onto a lateral aspect of an apophyseal ring of the target disc space.

In a second aspect of the invention, an orthopedic implant is disclosed. In one embodiment the device comprises two bone abutment members connected via an interconnecting member.

In a third aspect of the invention, a placement instrument configured to deliver the implant within the target disc space. In one embodiment, the instrument comprises an implant delivery segment, an anchor segment, and an articulating arm.

In a fourth aspect of the invention, a system for spinal stabilization is disclosed. In one embodiment, the system comprises at least two spinal implant apparatus configured to be placed within a target disc space via an implantation apparatus.

In a fifth aspect of the invention, a method for the minimally invasive placement of an orthopedic implant within a target inter-vertebral disc space is disclosed. In one embodiment, a first implant is placed into the posterior ipsilateral side of the disc space and a second implant is placed into the posterior contra-lateral side of the same disc space. The insertion instruments for both implants are, in one variant, rigidly anchored to each other, to the vertebral bone, and/or to the operating table onto which the subject is positioned. After instrument stabilization, each of the first and second implants are driven further into the disc space and away from one another, such that at least one of the implants comes to rest onto a segment of the lateral aspect of the apophyseal ring of the target disc space. The disclosed implants include devices that transition from a first total length and a first total width before insertion into the target disc space to a second lesser total length and a second greater total width after device implantation.

The details of one or more embodiments are set forth in the accompanying drawings and description below. Other features, objects, and advantages will be apparent from the following description, the accompanying drawings and from the claims.

BRIEF DESCRIPTION OF THE DRAWINGS

FIG. 1 is multiple views of an exemplary spinal vertebral bone.

FIG. 2A is a view of an exemplary functional spinal unit (FSU), which includes two adjacent vertebrae and the intervertebral disc between them illustrating a posterior surface of the adjacent vertebrae and the articulations between them.

FIG. 2B is an oblique view of the exemplary FSU of FIG. 2A.

FIG. 3 is a superior view of an exemplary spinal vertebral bone illustrating the apophyseal ring on the superior and the inferior surfaces thereof.

FIG. 4A is a side view of three exemplary vertebral bones having relatively normal alignment.

FIG. 4B is a side view of three exemplary vertebral bones having anterior displacement of the middle bone relative to the inferior-most bone.

FIG. 5 is a schematic diagram illustrating an exemplary interbody implant positioned within the disc space between the superior and inferior vertebral bodies of the immobilized FSU.

FIG. 6A is a side perspective view of the exemplary interbody implant of FIG. 5.

FIG. 6B is a cross-sectional view of the exemplary interbody implant of FIG. 5.

FIG. 7A is a schematic representation of an exemplary resection at the L4/5 disc space FIG. 7B is a schematic representation of the exemplary resection of FIG. 7A exposing the posterior aspect of the thecal sac.

FIG. 8A is a superior view of an exemplary defect in the posterior Annulus Fibrosis of the target disc space through which an exemplary implant is advanced.

FIG. 8B is a superior view of the exemplary implant placed within the target disc space of FIG. 8A.

FIGS. 10A and 10B are superior views of an exemplary implant advanced from a posterior to anterior direction by a placement instrument.

FIG. 12A is a superior view of exemplary implants in an expanded configuration after lateral placement.

FIG. 12B is a superior view of exemplary implants after placement of a bone forming material on at least one side of the vertebral midline.

FIG. 14 is multiple views of an exemplary assembled implant according to the present disclosure.

FIG. 19 is multiple views of transitioning of the exemplary implant from an open configuration to a closed configuration.

FIG. 20A is a side perspective view of the exemplary implant in a closed configuration.

FIG. 20B is a sectional view of the exemplary implant in a closed configuration.

FIG. 21 is multiple views of a contralateral side of an exemplary implant according to the present disclosure.

FIG. 22 is multiple views of another exemplary embodiment of an implant according to the present disclosure.

FIG. 24A is multiple views of a member of the exemplary embodiment of the implant of FIG. 22.

FIG. 24B is a superior view of utilization of a placement instrument to implant the exemplary implant of FIG. 22 within the target disc space.

FIG. 24C is a superior view of the medial displacement of the exemplary implant of FIG. 22 within the target disc space.

FIGS. 24D and 24E are prospective views of the exemplary implant of FIG. 22 implanted within the target disc space and having the bone forming material disposed therein.

FIG. 32 is multiple views of utilization of a placement instrument to place the members of the exemplary implant.

FIG. 34A is a side and oblique view of another exemplary embodiment of an implant according to the present invention.

FIG. 34B is a side view illustrating movement of one or more segments of the exemplary implant of FIG. 34A.

FIG. 34C is a superior view of the exemplary implant of FIG. 34A within an exemplary vertebral bone.

FIG. 35A is multiple views of an exemplary expandable implant adapted to expand after implantation into the target disc space.

FIG. 35B is an expanded view of the exemplary implant of FIG. 35A.

FIG. 36A is a superior view of an exemplary implant being introduced into a target disc space.

FIG. 36B is a superior view of the exemplary implant displaced laterally within the target disc space.

FIG. 37 is a superior view of two bilaterally positioned implants according to one embodiment of the present disclosure.

FIG. 38A is a superior view of advancement of two exemplary first implants into the target disc space.

FIG. 38B is a superior view of rotation of the exemplary implants of FIG. 38A laterally within the target disc space.

FIG. 39A is a superior view of advancement of two exemplary second implants into the target disc space.

FIG. 39B is a superior view of a lateral translation of the two exemplary second implants of FIG. 39A within the target disc space.

FIG. 41 is multiple views of an exemplary spinous process fixation implant.

FIG. 42A is a lateral view of an implanted FSU with the exemplary implant of FIG. 41.

FIG. 42B is an axial view of an implanted FSU with the exemplary implant of FIG. 41.

Figure 9B:
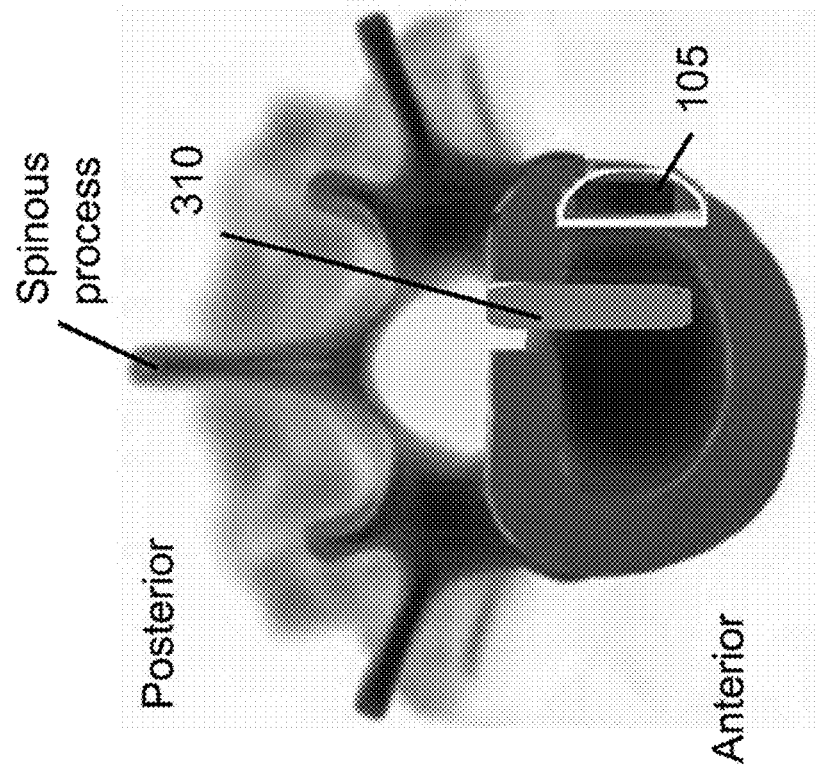
FIG. 9B is a superior view of a bone forming material place into the decorticated area of the disc space.

All Figures © Copyright 2013. Samy Abdou. All rights reserved.

Overview

In one aspect, improved apparatus and methods for spinal stabilization are disclosed. In one exemplary implementation, the improved is advantageously used as part of minimally invasive procedures—including percutaneous operations. Additionally, the improved interbody device and its method of implantation may be employed in any applicable interbody fusion procedure and used at any spinal segment. Still further, the exemplary embodiments of the improved interbody device are configured to provide a safe and reproducible method for performing a minimally invasive posterior vertebral fusion.

DETAILED DESCRIPTION

In order to promote an understanding of the principals of the disclosure, reference is made to the drawings and the embodiments illustrated therein. Nevertheless, it will be understood that the drawings are illustrative and no limitation of the scope of the disclosure is thereby intended. Any such alterations and further modifications in the illustrated embodiments, and any such further applications of the principles of the disclosure as illustrated herein are contemplated as would normally occur to one of ordinary skill in the art.

FIG. 1 shows a diagrammatic representation of a spinal vertebral bone 802 in multiple views. For clarity of illustration, the vertebral bone of FIG. 1 and those of other illustrations presented in this application are represented schematically and those skilled in the art will appreciate that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. Thus, the disclosed devices and methods may be applied at any applicable spinal level.

Vertebral bone 802 contains an anteriorly-placed vertebral body 804, a centrally placed spinal canal 806 and posteriorly-placed lamina 808. The pedicle (810) segments of vertebral bone 802 form the lateral aspect of the spinal canal and connect the laminas 808 to the vertebral body 804. The spinal canal contains neural structures such as the spinal cord and/or nerves. A midline protrusion termed the spinous process (SP) extends posteriorly from the medial aspect of laminas 808. A protrusion extends laterally from each side of the posterior aspect of the vertebral bone and is termed the transverse process (TP). A right transverse process (RTP) extends to the right and a left transverse process (LTP) extends to the left. A superior protrusion extends superiorly above the lamina on each side of the vertebral midline and is termed the superior articulating process (SAP). An inferior protrusion extends inferiorly below the lamina on each side of the vertebral midline and is termed the inferior articulating process (IAP). Note that the posterior aspect of the pedicle can be accessed at an indentation 811 in the vertebral bone between the lateral aspect of the SAP and the medial aspect of the transverse process (TP). In surgery, it is common practice to anchor a bone fastener into the pedicle portion of a vertebral bone by inserting the fastener through indentation 811 and into the underlying pedicle.

FIGS. 2A and 2B illustrate a functional spinal unit (FSU), which includes two adjacent vertebrae and the intervertebral disc between them. The intervertebral disc resides between the inferior surface of the upper vertebral body and the superior surface of the lower vertebral body. (Note that a space is shown in FIGS. 2A and 2B where intervertebral disc would reside.) FIG. 2A shows the posterior surface of the adjacent vertebrae and the articulations between them while FIG. 2B shows an oblique view. Note that FSU contains a three joint complex between the two vertebral bones, with the intervertebral disc comprising the anterior joint. The posterior joints include a facet joint 814 on each side of the midline, wherein the facet joint contains the articulation between the IAP of the superior vertebral bone and the SAP of the inferior bone.

The preceding illustrations and definitions of anatomical structures are known to those of ordinary skill in the art. They are described in more detail in *Atlas of Human Anatomy*, by Frank Netter, third edition, Icon Learning Systems, Teterboro, N.J., the text of which is herein incorporated by reference in its entirety.

The apophyseal ring is the outer rim segment that is located on each of the superior and the inferior surfaces of a vertebral bone—as shown in FIG. 3. (Note that the superior and inferior surfaces of the vertebral bone are those surfaces that abut the intervertebral discs.) The apophyseal ring is circumferentially positioned and forms the most dense and strongest portion of the superior and inferior surfaces of the vertebral bone. The ring is comprised of dense bone that anchors the external fibers of the annulus fibrosis of the adjacent intervertebral disc. (The epiphyseal ring (which is similar to the apophyseal ring) is discussed in detail in: *The epiphyseal ring: a long forgotten anatomical structure with significant physiological function*. Dar G, et al. Spine (Phila Pa. 1976). 2011 May 15; 36(11):850-6, which is herein incorporated by reference in its entirety.)

In a healthy spine that is functioning within physiological parameters, the two facet joints of an FSU (Functional Spinal Unit) collectively function to prevent aberrant relative movement of the vertebral bones in the horizontal (i.e., axial) plane. (The horizontal plane of a human spine refers to a plane of the erect spine that is substantially parallel to a level floor on which the subject is standing). With aging and spinal degeneration, displacement of the vertebral bones in the horizontal plane may occur and the condition is termed spondylolisthesis. FIG. 4A illustrates three vertebral bones with relatively normal alignment, whereas FIG. 4B shows the anterior displacement of the middle bone relative to the inferior-most bone. In the illustration, the vertebral column of FIG. 4B is said to have an anterior spondylolisthesis of the middle vertebral bone relative to the inferior-most vertebral bone.

A spondylolisthesis can be anterior, as shown in FIG. 4B, or posterior wherein a superior vertebral bone of a functional spinal unit is posteriorly displaced in the horizontal plane relative to the inferior vertebral bone. In general, anterior sponylolisthesis is more common and more clinically relevant than posterior sponylolisthesis. (Sponylolisthesis can be further classified based on the extent of vertebral displacement. See Principles and practice of spine surgery by Vaccaro, Bets, Zeidman; Mosby press, Philadelphia, Pa.; 2003. The text is incorporated by reference in its entirety.)

With degeneration of the spine, constriction of the spinal canal and impingement of the contained nerve elements frequently occurs and is termed spinal stenosis. Spondylolisthesis exacerbates the extent of nerve compression within the spinal canal since misalignment of bone within the horizontal plane will further reduce the size of the spinal canal. Relief of the compressed nerves can be achieved by the surgical removal of the bone and ligamentous structures that constrict the spinal canal. However, decompression of the spinal canal can further weaken the facet joints and increase the possibility of additional aberrant vertebral movement. That is, spinal decompression may worsen the extent of spondylolisthesis or produce spondylolisthesis in an otherwise normally aligned FSU. After decompression, surgeons will commonly fuse and immobilize the adjacent spinal bones in order to prevent the development of post-operative vertebral misalignment and spondylolisthesis.

Regardless of the clinical reason or indication for fusion of the vertebral bones, many surgeons position an implant within the disc space that rests between the two vertebral bones to be fused. An example of a generic interbody implant is shown positioned within the disc space between the superior and inferior vertebral bodies of the immobilized FSU in FIG. 5, wherein a side view of an FSU is shown. Many embodiments of interbody implants are known in the art, and U.S. Pat. Nos. 4,636,217; 5,015,247; 5,192,327; 5,443514; 5,749,916, 6,251,140; 6,342,074; 6,706,070; 6,767,367; 6,770,096; 6,852,127; 7,037,339; 7,227,477; 7,641,690, among others, disclose some of these inter-body implant device. (Each of the listed patents is herein incorporated by reference in its entirety). In general, and as shown in the example of FIG. 6, a generic interbody implant is usually comprised of an outer superstructure 925 that is a manufactured of a synthetic biocompatible material (such as metal alloy, plastic material, ceramics, and the like) and an internal cavity 922 this is configured to house a bone forming material. Open bores 927 permit communication and fusion between the vertebral bone(s) outside of the device and the bone forming material contained within cavity 922. In general, the superstructure separates and supports the vertebral bones that abut the implanted disc space. In this way, the device can be used to maintain the disc space height. The internal cavity contains the bone formation material that will form the actual fusion mass that will eventually extend from the superior to the inferior vertebral bones. When the superstructure 925 is manufactured from metallic alloy, it can be advantageously made of limited thickness thereby providing a larger internal cavity 922 for containment of a larger volume of bone forming material. However, the metallic superstructure is generally X-ray opaque and thus limits the ability to follow bone healing in the post-operative period. In contrast, manufacture of superstructure 925 from plastic materials (such as PEEK) or ceramics permits good X-ray visualization of the healing bone within but significantly limits the size of internal cavity 922 and the volume of bone forming material contained therein.

Considerable clinical experience has been gained in the implantation of these interbody implants via a posterior surgical corridor and the limitations and disadvantages of this general design are becoming known. In a first limitation, these implants are generally large, have a width of at least 10 mm, and requiring substantial bony resection of the posterior spinal elements for device implantation. Implantation of these devices through a posterior surgical approach often involves removal of substantial portions of the facet joint at the implanted level. (It should be noted disc space fusion via a posterior approach without significant facet resection is termed a posterior lumbar interbody fusion (PLIF), whereas extensive facet joint resection and use of a slightly more lateral corridor is termed a trans-foraminal lumbar interbody fusion (TLIF)). Facet joint resection adds to the surgical work. It also significantly destabilizes the implanted FSU so that pedicle screw fixation is needed to re-stabilize the operative level. That is, the implantation of the interbody device may require enough bony resection so as to require large supplemental fixation devices and obviate the use of minimally invasive fixation device—such as spinous process fixators. Given the proximity to nerve elements to the posterior surgical corridor, implant placement with limited facet resection requires a greater degree of nerve retraction and increases the risk of nerve injury. Finally, prior attempts to reduce the width of the interbody implant have produces implants with height to width ratio that is greater than one, and have increased the risk of implant roll-over within the disc space.

While the overall implant diameter must be kept at a minimum because of the limited implantation corridor, containment of the bone graft material with an internal cavity of the implant provides a second limitation—since the volume of bone graft material contained within the implant is necessarily small. Attempts to maximize the graft cavity size by decreasing implant wall thickness will require that the implant be manufactured from metallic alloys. As already noted, metallic alloys are radio-opaque and will prevent adequate X-ray evaluation of bone healing in the post-operative period.

In a third limitation, the totality of the section of the disc space on which the implant will rest must be prepared by removal of the cartilaginous end plate and decortication of the vertebral bone surfaces that abut (i.e., upper and lower vertebrae) the implant. This is performed so that the bone graft material contained within the implant will fuse with the adjacent vertebral bones. The area of end plate decortication has width of at least D1 (FIG. 6A), which is total width of the implant, instead of limiting decortication to the width D2. Unfortunately, decortication of the bony segment upon which the superstructure 925 rests will thin the cortical bone and disadvantageously predispose to implant subsidence within the vertebral bones. This is especially problematic, since subsidence reduces disc space height and threatens to re-trap the adjacent nerve elements—which would obviate the very purpose of the operative procedure. Finally, the decortication process is laborious and adds to the time required to complete the procedure.

It is a purpose of the present disclosure to disclose an improved interbody device. The device is particularly advantageous for use in minimally invasive procedures-including percutaneous operations. However, the device and its method of implantation may be employed in any applicable interbody fusion procedure and used at any spinal segment.

It is a purpose of the present disclosure to separate the region of the device that provides vertebral support (such as, for example, the superstructure) from that region of the device that houses the material needed to form the fusion mass. The two regions may be implanted separately into the disc space and simply positioned adjacent to one another without mutual attachment. Alternatively, the two separate regions may be attached to one another. Separation of the two segments allows the vertebral support segment to be manufactured form metallic alloys, if desired, without obscuring post-operative X-ray follow-up of bone healing. In a one embodiment, the width of the implant is less than 8 mm at the time of its advancement through the spinal canal (i.e., at the time of insertion past the nerve elements). However other widths may be utilized with equal success.

It is a purpose of the present disclosure to provide a method for the safe and reproducible placement of an interbody device into an intervertebral disc space. In a first embodiment, the interbody device is employed without other bone fixation implants (i.e., as a "stand alone" device). In a second embodiment, the interbody device is employed in conjunction with a spinous process fixation implant. In a third embodiment, the interbody device is used with pedicle screw fixation of the vertebral bones. That is, a pedicle screw is placed into an ipsilateral pedicle of each of the superior and inferior vertebral bones that abut the implanted disc space. The bone screws are joined by an interconnecting member, such as a rod, and the assembly is used to rigidly fixate the vertebral bones to one another. (It is understood that either the interbody device or the pedicle screw/rod assembly may be used on one side of the vertebral midline alone (unilateral) or on both sides of the vertebral midline (bilateral). The vertebral midline is substantially defined by the mid-sagittal plane that bisects the implanted disc space/vertebral bones into a right half and a left half). In other embodiments, the interbody device may be used with additional bone fixation implant.

In one embodiment of a method for device placement, the disc space that is targeted for inter-body device implantation is identified using radiographic imagining techniques (such as X-rays, CT, MRI and the like). A skin incision is made in the skin immediately posterior to the target disc space. The paraspinal muscles are retracted and a corridor is developed adjacent to the spinous process and the posterior aspect of the lamina. The lamina of each of the superior and inferior vertebrae that border the targeted disc space are identified. In one particular embodiment, this may be accomplished via an imaging modality. Resection of the lamina posterior to the target disc space is performed, wherein at least a portion of the inferior aspect of the lamina of the superior vertebral bone (i.e., the vertebral bone that forms the superior border of the target disc space) is removed. This is schematically shown as resection of segment 1152 (FIG. 7A) when targeting the L4/5 disc space.

An additional resection of the lamina posterior to the target disc is performed, wherein at least a portion of the superior aspect of the lamina of the inferior vertebral bone (i.e., the vertebral bone that forms the inferior border of the target disc space) is removed. This is schematically shown as resection of segment 1153 (FIG. 7A) when targeting the L4/5 disc space. At least a portion of the ligament (i.e., the ligamentum flavum) that spans the region of lamina resection is also removed. In this way the posterior aspect of the thecal sac is exposed through window "W" of FIG. 7B. While shown as being performed on only one side of the midline, it is understood that window W may be placed bilaterally. (In one particular embodiment, Window W is located on either side of the vertebral midline, wherein the vertebral midline is defined by a sagittal plane that substantially extends through the spinous process and divides a vertebral bone into a left and a right half.)

The posterior aspect of the target disc space is exposed through a corridor that is lateral to the nerve elements (and thecal sac), wherein the lateral aspect of the corridor is substantially at or lateral to the medial border to the pedicles. This is best appreciated by the operating surgeon by exposing the medical aspect of the pedicle of the inferior vertebral bone (i.e., the vertebral bone that forms the inferior border of the target disc space). Plane A is positioned substantially at the medial border of the pedicle 810 and is schematically shown in FIG. 3.

The nerve elements are retracted gently in the medial direction and the posterior aspect of the target disc space is identified. The disc space is entered and at least a segment of the disc material may be removed (termed discectomy).

FIG. 8A illustrates the defect 1170 in the posterior Annulus Fibrosis of the target disc space through which implant 105 is being advanced into the target disc space (FIG. 8B). In one particular embodiment, the medial to lateral dimension of the posterior entry window into the disc space is less than 8.1 mm. The implant 105 is attached to an implant placement instrument 205. In another particular embodiment, the medial to lateral dimension of implant 105 as it enters the posterior aspect of the target disc space is less than 6.1 mm. The implant placement instrument may attach onto an outer surface of the implant (such as, for example, a posterior surface thereof). While not illustrated, the implant is alternatively (or additionally) advanced into the disc space through a port that forms a corridor to deliver the implant into the target disc space. That is, the implant placement instrument may comprise an internal channel through which the implant is advanced into the target disc space. Regardless of placement instrument design and configuration, the implant may be advanced into the posterior aspect of the target disc space using a posterior to anterior trajectory that is substantially parallel to the mid-sagittal plane (see FIGS. 8A and B).

A collapsed disc space having a small vertical height is distracted back to a desired height of greater value by the sequential/iterative placement of shims or distractors within the disc space. Alternatively, or in addition, the implant placement instrument may also serve as a distractor of the disc space. For example, the placement instrument may have a segment that is sized to be positioned within the disc space. The intra-discal segment is comprised of an upper and lower surface, such that the upper surface may be forcibly distracted away from the lower surface. In this way, the vertebral bone superior to the target disc space can be forcibly moved away from its immediately inferior vertebral bone and thereby increase the superior to inferior height of the target disc space. (Note that a collapsed disc space has a disc space height that is substantially below the normal value for that disc space level, wherein the disc space height is the vertical distance from the superior disc space surface to the inferior disc space surface.)

As shown in FIG. 8B, implant 105 is placed with its lateral surface substantially at or medial to plane A (Figured 8B), wherein plane A is a sagittal plane substantially at the medial aspect of the pedicle of the inferior vertebral bone. Implant 105 is then translated laterally within the disc space so that it rests at least partially on the lateral aspect of the apophyseal ring. In another embodiment, the lateral aspect of the implant rests at the lateral border of the disc space (at the approximate level of the lateral wall of each of the superior and inferior vertebral bones—see FIG. 9A). Prior to the lateral displacement of implant 105 with in the target disc space, in one embodiment, at least a portion the placement instrument and/or implant delivery port are anchored to the vertebral bone and/or onto the operating room table. This is done in order to counter the opposing force that would be felt by the placement instrument—as a reaction to the laterally-directed force applied to implant 105. Without anchoring or securing the placement instrument, the surgeon's ability to move the implant laterally within the disc space is limited. Further, the un-anchored placement instrument will necessarily be displaced medially in reaction to a force that displaces the implant laterally. Since the nerves are immediately medial to the placement instrument, medial movement of the placement instrument will impinge the nerve elements and can produce nerve injury.

The placement instrument and/or implant delivery port are anchored into the posterior bony surface of the inferior vertebral body and/or the superior vertebral body in one embodiment. They may be anchored into the pedicle of the inferior vertebral bone and/or directly into any other part of vertebral bones that are adjacent to (or abut) the target disc pace. They may be also anchored directly to a first segment of an articulating retention arm wherein a second segment of the arm is rigidly attached to the operating room table upon which the patient is positioned. (An example of an articulating retention arm is show in FIG. 9C.) When the procedure is performed bilaterally (see FIGS. 10-12), the placement instrument and/or implant delivery port may be also (or alternatively) anchored rigidly and directly to one another as will be discussed below. The relative advantages of this method of anchoring the placement instrumentation will also be disclosed below.

Frame devices that anchor surgical instruments to the operating table are known in the art. In the illustrated device (FIG. 9C), articulated frame 905 has member 9052 that reversibly attaches to the operating table onto which the patient is positioned. Member 9056 is adapted to reversibly and rigidly clamp onto a segment of the placement instrument 208. Member 9054 is adapted to reversibly transition the frame 905 from the first state (movably articulating frame segments) to the second state (articulated frame segments are rigidly locked to one another). While an example of an articulated frame 905 is illustrated, it is understood that any other applicable such device may be alternatively used. (For example, U.S. Pat. Nos. 4,254,763; 5,908,382; 6,302,843; 6,709,389; 7,156,806, and many others are known to disclose surgical retractor systems that anchor to the operating table. Each of the foregoing is herein incorporated by reference in its entirety).

Figure 9A:
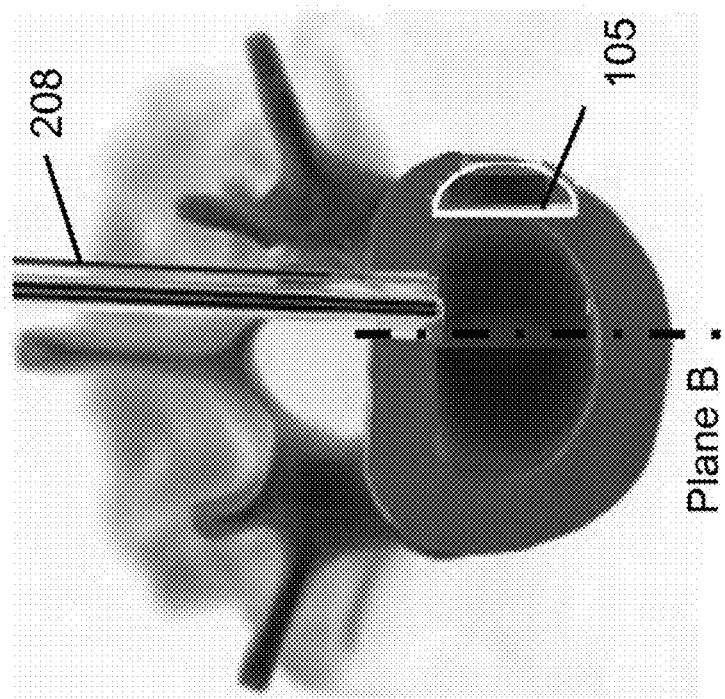
FIG. 9A is a superior view of the exemplary implant having been displaced laterally in the disc space and then detached from placement instrument.

FIG. 9A illustrated implant 105 having been displaced laterally in the disc space and then detached from placement instrument 208. The region of the disc space medial to the implant can then be prepared to accept a bone graft member. This is performed by the removal of at least a portion of the disc space as well as decortication (which is comprised of removal of the cartilaginous end plate from bone) of the inferior surface of the upper vertebral bone and the superior surface of the lower vertebral bone. Note that removal of the disc material may be performed through the area of the disc space that will become in contact with the implant. (For example, the disc material is removed from the medial limit of the area of implant entry into the disc space (plane B of FIG. 9A) to the lateral aspect of the disc space, where the implant will be ultimately positioned.) In contrast, the area of decortication (i.e., removal of the cartilaginous end plate) is generally limited to the area into which the bone graft material (such as bone graft 310) is placed. This provides the relative advantage of discectomy of the area of the target disc space in which the implant will abut the vertebral bone surface rather than decortication of the abutted bone surfaces. After decortication of the vertebral bone surface that is adjacent to the surface abutted by the implant, an allograft or autograft bone graft segment 310 and/or bone graft substitute (collectively termed bone forming material) is placed into the decorticated area of the disc space—as shown in FIG. 9B.

In an alternative embodiment, the procedure may be performed bilaterally. FIGS. 10A and 10B show an implant 105 being advanced from a posterior to anterior direction by a placement instrument 208. In one embodiment, the medial to lateral dimension of the posterior entry window into the disc space is less than 8.1 mm. In another embodiment, the medial to lateral dimension of the implant 105 as it enters the posterior aspect of the target disc space is less than 6.1 mm. A first implant 105 is advanced into the disc space through a corridor immediately lateral to the nerves/thecal sac but substantially medial to the plane demarcating a medial aspect of the inferior pedicle (such as, for example, plane A of FIG. 8B). All of the procedural steps disclosed above for the unilateral implant placement are performed. These steps are repeated with a second implant 105 using a comparable but contralateral corridor. (Note that contralateral implant placement indicated positioning the second implant across the vertebral midline from the first implant, wherein the midline is defined by a sagittal plane that divides the vertebral bone into a right and a left half—as shown in FIG. 8B.)

Figure 13A:
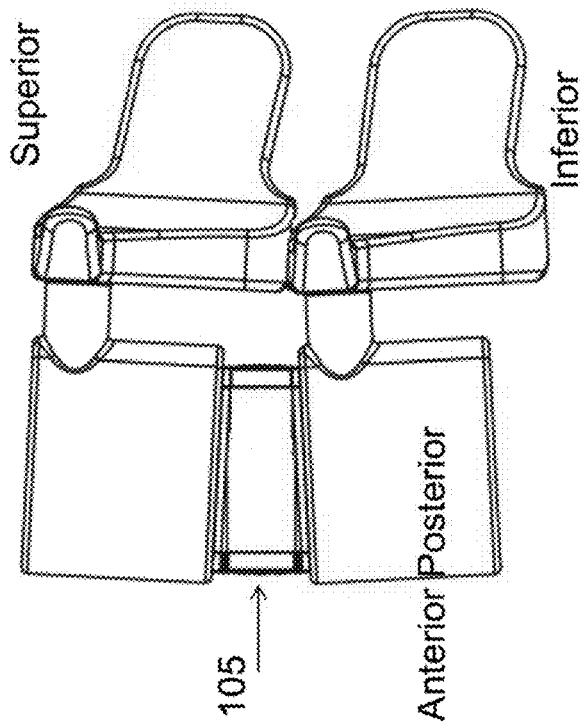
FIG. 13A is a sagital view of an exemplary implant being used to align the implanted FSU segment.
Figure 13B:
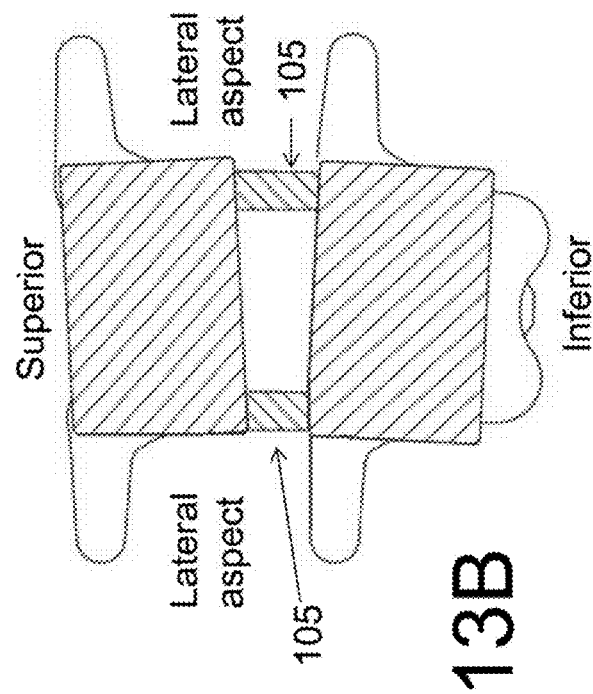
FIG. 13B is a coronal plane section of the vertebral bones that surround an implanted disc space.

While each implant is labeled as implant 105, it is understood that the implants need not be identical. For example, the implants may be mirror images of one another or of completely different design, configurations or size. That is, it is contemplated that any implant that is sized and configured for intervertebral disc space implantation may be used on either side. By varying the configuration and size, for example, the implant may be used to impart a different height to the anterior disc space than the posterior disc space and thereby align the implanted FSU segment into a more or a less lordotic curvature (FIG. 13A—in sagittal view). Further, the heights of implant 105 on either side of vertebral midline may be different so as to change the alignment of the implanted FSU in the coronal plane of the spinal column—such as, for example, in the correction of scoliosis. The latter is illustrated in FIG. 13B and shows a coronal plane section of the vertebral bones that surround an implanted disc space. Note the coronal plane curvature created by the different sized implants 105. Finally, it is understood that each of the two implants are placed into the disc space using a posterior (to anterior) corridor substantially medial to the medial aspect of the pedicle (such as plane A of FIG. 8B) but lateral to the thecal sac. That is, the thecal sac rests between each of the placement instruments 208—as shown by "X" in FIG. 10B.

In another embodiment, and as show in the axial plane view of FIG. 12A, implant 105 of the first side is separated from the contralateral 105. That is, implants 105 do not abut one another and are not coupled or connect to one another by one or more other members. Each of implant 105 is freely movable relative to the other implant 105 within the implanted disc space. That is, the application of a force to one implant 105 may not be felt or have any effect on the other/contralateral implant 105. Any bone graft material that is implant between the opposing implants 105 would not necessarily interlock together the implants 105.

Prior to lateral displacement of each implant 105, the placement instrument 208 and/or implant delivery port are rigidly anchored relative to the disc space, so as to counter the medially-oriented force that will be felt by the placement instrumentation in reaction to the laterally-oriented force applied to the implant. The anchor is of critical importance, since a non-anchored placement instrument will be displaced medially itself instead of being able to displace the implant laterally. The placement instrument 208 and/or implant delivery port may be anchored (such as with a bone anchor) into the posterior bony surface of the inferior vertebral body and/or the superior vertebral body. They may be also anchored into the pedicle of the inferior/superior vertebral bones. They may be also anchored onto any posterior surface of the vertebral bones such as, for example, the spinous processes or lamina.

Figure 9C:
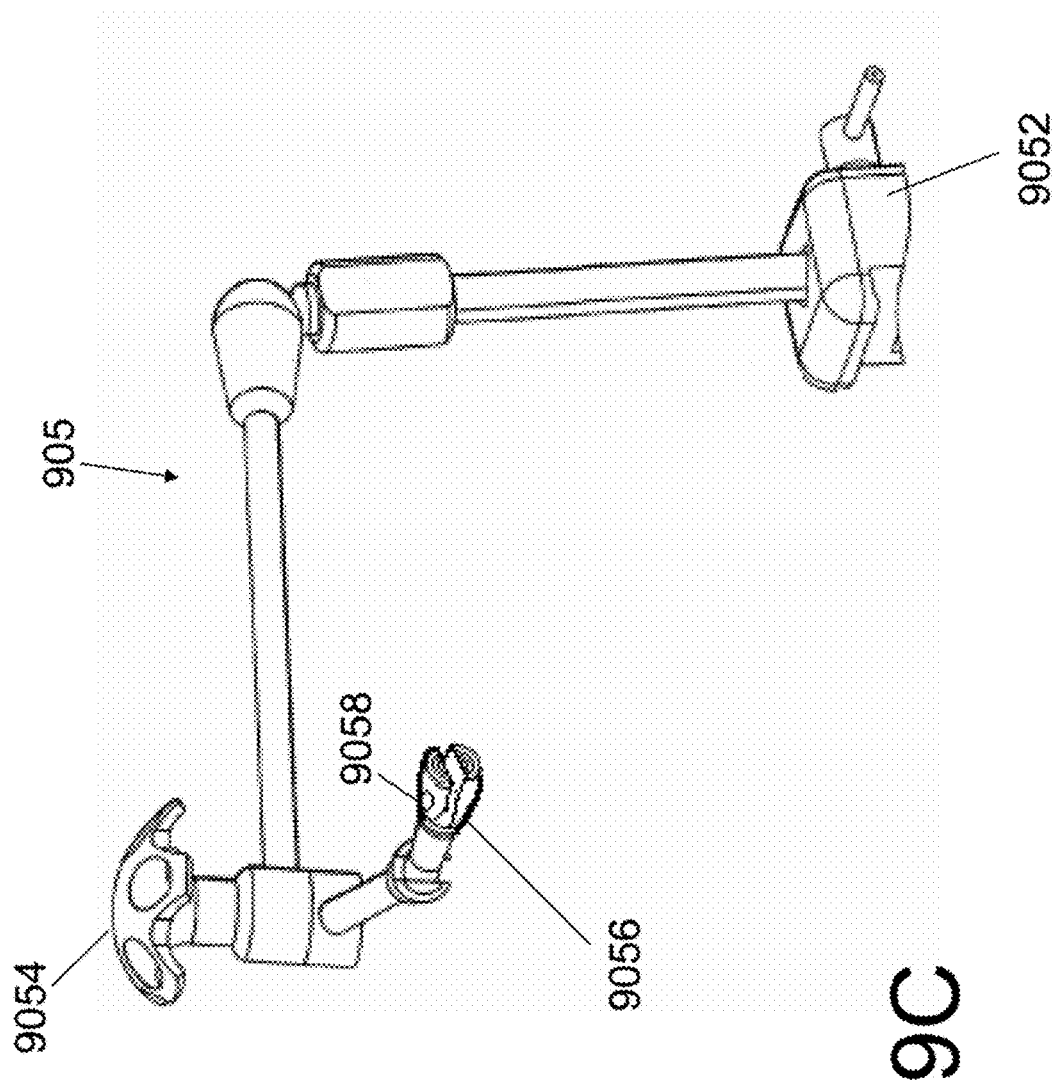
FIG. 9C is a side perspective view of an exemplary articulating retention arm.

The placement instruments may be also anchored directly within the disc space to be implanted (such as, for example, using a wedge/shim). They may be also anchored directly to a first segment of an articulating retention arm wherein a second segment of the arm is rigidly attached to the operating room table upon which the patient is positioned. (An example of an articulating retention arm is shown in FIG. 9c and will be discussed further below.)

Figures 11A, 11B:
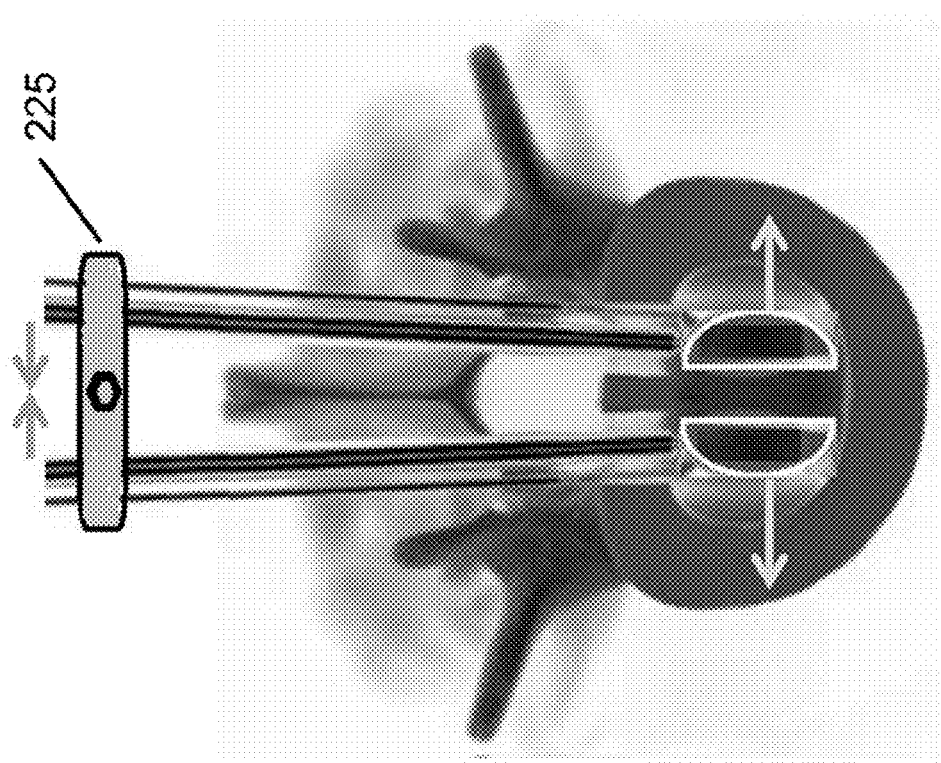
FIG. 11A is a superior view of an exemplary connecting member configured to connect an exemplary placement instrument to an exemplary contralateral instrument.
FIG. 11B is a superior view of exemplary implants in a non-expandable configuration after lateral displacement.

In bilateral implant placement, a placement instrument 218 can be also rigidly connected to the contralateral instrument 218, such as, for example, using connecting member 225 of FIG. 11A. In this configuration, the medially-directed force generated by the lateral displacement of an implant (see arrows of FIG. 11A) is substantially offset by an opposing force of similar magnitude that is generated by lateral displacement of the contralateral implant. (The use of a connecting member between placement instruments will be discussed further below.) It is further contemplated that the placement instrument may be placed into the disc space on either side of the midline and then interconnected—as shown in FIGS. 10-12. Alternatively, the placement instruments may be interconnected to one another prior to advancement into the disc space. The interconnection may be rigid at the time of introduction of placement instruments into the disc space, or it may be an adjustable/malleable interconnection that is subsequently made rigid after advancement of the placement instruments into the disc space but prior to the deployment of the implants. In this embodiment, the interconnecting member must necessarily cross the plane of the vertebral midline.

Note that any of the aforementioned anchoring regions/methods are not mutually exclusive and more than one of them may be concurrently used to rigidly anchor the placement instrument and/or implant delivery port relative to the FSU to be implanted.

FIG. 11B shows the implants after lateral displacement. At least one (and in one embodiment both) of the bilaterally-placed implants is positioned with at least a portion of the implant abutting the lateral aspect of the apophyseal ring. That is, at least a portion of at least one of the implants rests on the lateral aspect of the apophyseal ring. The implant may be of a non-expandable configuration, as shown in FIG. 11B, or it may expand and transition to a greater width within the disc space, as shown in FIG. 12A. While not shown in these axial views, it further contemplated that the implant may transition to a different height. (Implant height is defined as substantially being the greatest implant measure from the inferior surface of the superior bone to the upper abutment surface of the inferior bone). FIG. 12B illustrates the construct after placement of bone forming material 310 on at least one side of the vertebral midline. The procedure needed for graft placement was disclosed above.

Alternative implant embodiments will now be described. Since it is contemplated that any implant that is sized and configured for intervertebral disc space implantation may be used, the following embodiments are provided as examples and are not intended to be limiting in any way.

Figure 15:
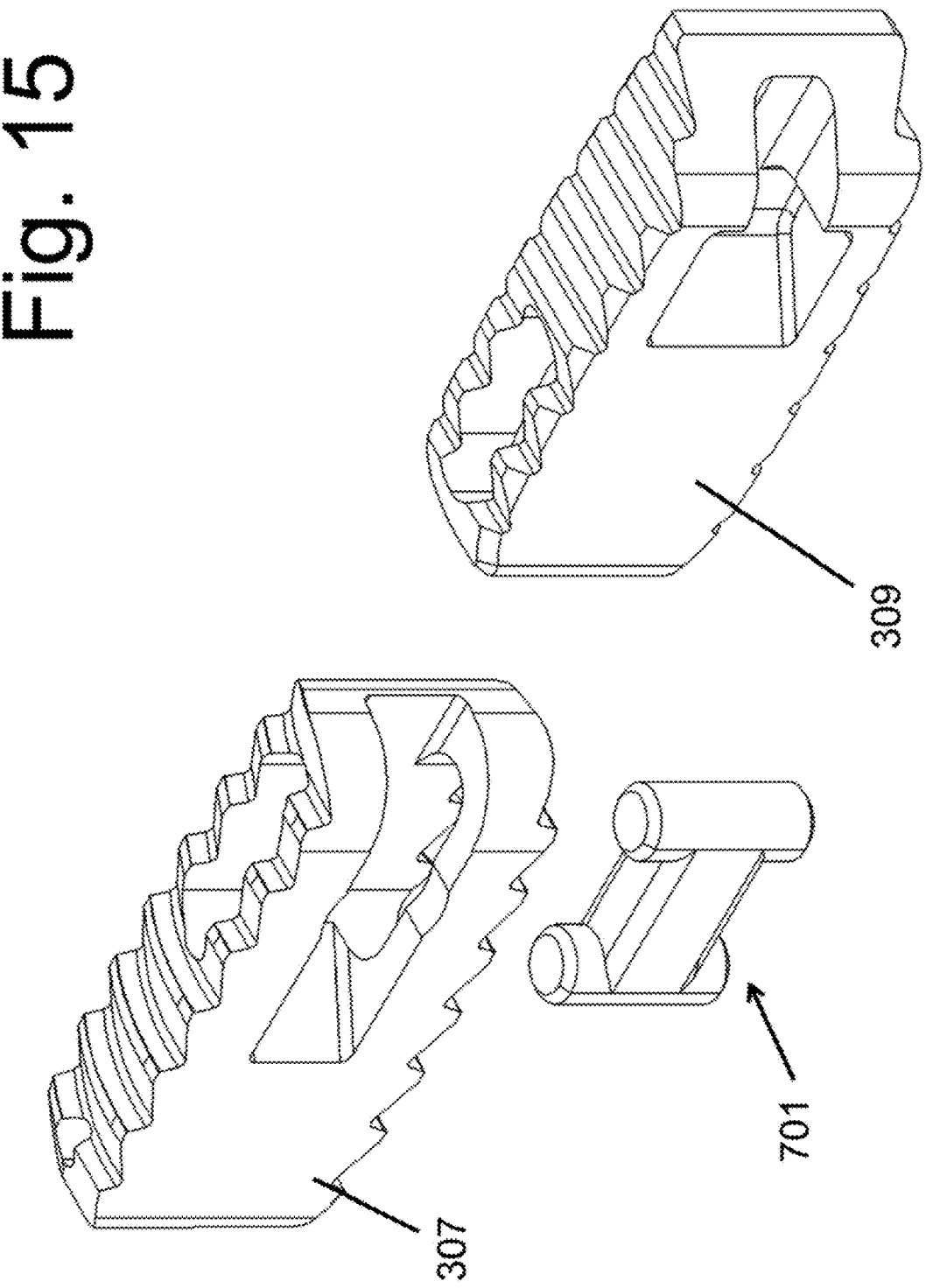
FIG. 15 is an exploded view of the exemplary assembled implant of FIG. 14.

In an embodiment, an implant 301 has diameter "D" which is equal to or less than 8 mm, and has a height "H" that is equal to or greater than 8 mm. Implant 301 is comprised of a first member 307 and a second member 309 that are linearly aligned. Members 307 and 309 may be movably interconnected by member 701, as shown, or may be unattached to one another (that is, member 307 and 309 may be simply arranged to follow one another into the disc space but to be otherwise not interconnected). Members 307 and 309 may be of the same or different heights H (as measured from a lower implant surface abutting the upper surface of the lower vertebral body to an upper implant surface abutting the lower surface of the upper vertebral body). When implants 307 and 309 are different in heights, it is preferred (however, not necessary) that implant 309 be of greater height. FIG. 14 shows views of the assembled implant 301 whereas FIG. 15 shows an exploded view.

In an embodiment, members 307 and 309 may be of the same or different widths D (the width is the measure of the side to side distance, such as, for example, width D of FIG. 14). The members are linearly aligned in one embodiment such that the greatest width across the implant 301 is no greater than width of the implant 307 and/or 309 that is of greater width. As implant is advanced past the nerve elements and into the disc space, members 307 and 309 are aligned in tandem, as shown in FIG. 14, with a front end of member 309 abutting a back end of member 307. In order to minimize the implant width as it passes through the spinal canal (and the nerves contained therein), the side surfaces of member 307 and 309 do not overlap in the expanded configuration shown in FIG. 14. Once into the disc space, members 307 and 309 are repositioned to rest next to one another, as shown in FIG. 20. That is, in the expanded configuration, the length L of implant 301 is substantially equal to the sum of length L1 of member 307 and length L2 of member 309 (FIG. 14).

In an embodiment, at least one of member 307 and/or 309 will contain a cavity that is at least partially contained within its internal aspect and configured to house a bone forming material that can fuse with at least one adjacent vertebral bone. In another embodiment, neither implant contains bone graft material within it. In another embodiment, at least one of members 307 and/or 309 has greater height than the implanted disc space, so that at implantation, the member is recessed within a bony defect that is cut within the superior and/or inferior vertebral bone. In another embodiment, neither member 307 nor 309 is recessed within a cavity cut into the adjacent vertebral bone, but each of the members rests on the intact endplate of the vertebral bones.

Figure 16:
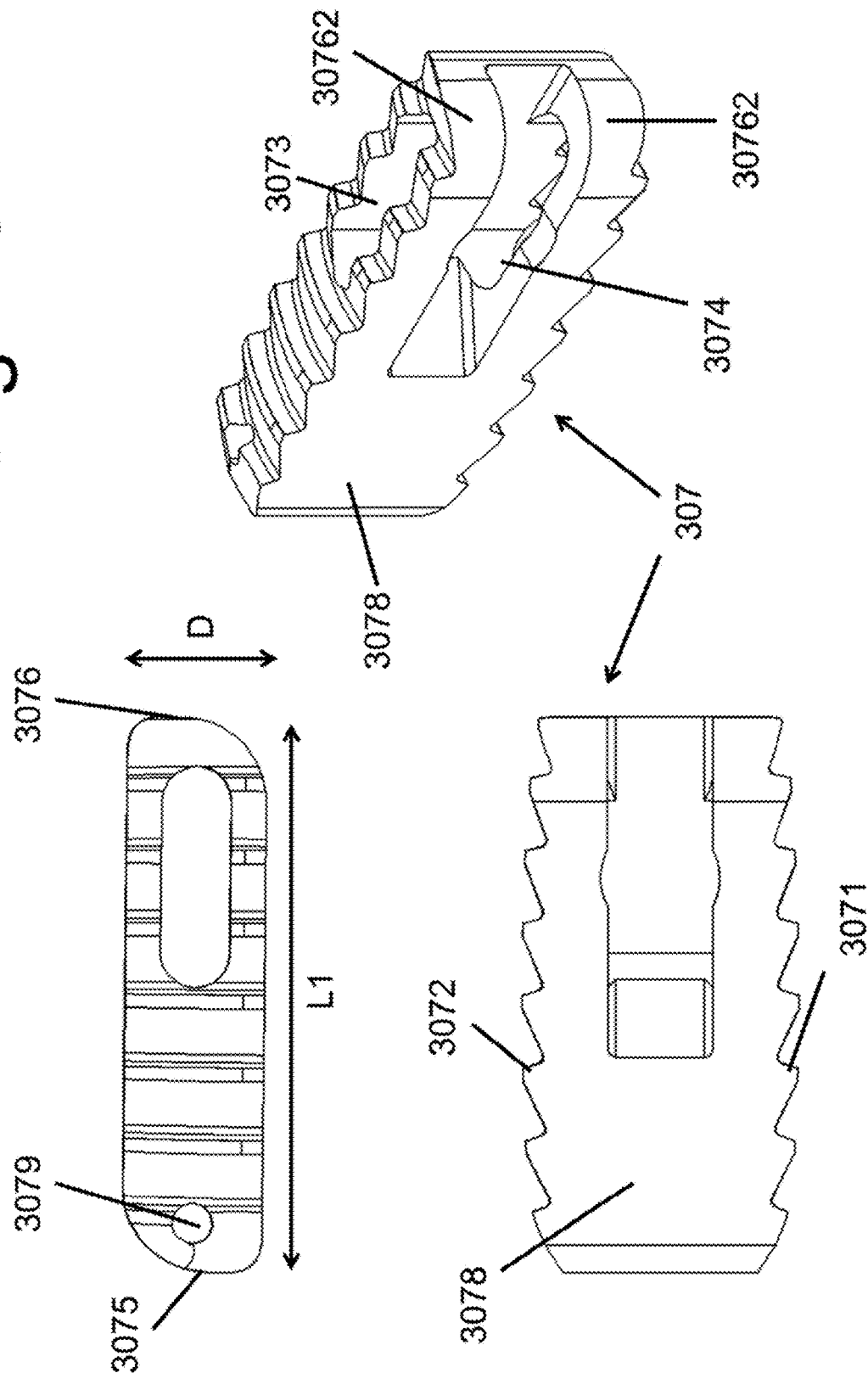
FIG. 16 is multiple views of a first member of the exemplary assembled implant according to the present disclosure.

FIG. 16 shows multiple views of member 307. There is a superior surface 3072 and inferior surface 3071, which contain protrusions or are otherwise textured to increase fixation into the adjacent bone in one embodiment. Member 307 contains a front end 3075, a back end 3076 and side walls 3078. Channel 3073 extends from superior surface 3072 to inferior surface 3071. Side channel 3074 extends from a first side wall 3078 to channel 3073, but does not extend to opposing wall 3078. Channels 3073 and 3074 are configured to accept member 701. Back end 3076 contains curved segments 30762 that allow member 309 to rotate from a posterior to a side position relative to member 307—as will be discussed below. Bore 3079 accepts a radio-opaque marker so that the implant's position may be identified by X-ray imaging after implantation into a subject. The terms superior, inferior, cephalad, caudad, top, bottom, front, back, side and the like are used to facilitate description of this and other the members/devices in this application. The usage is not intended to be limiting in any way.

Figure 17:
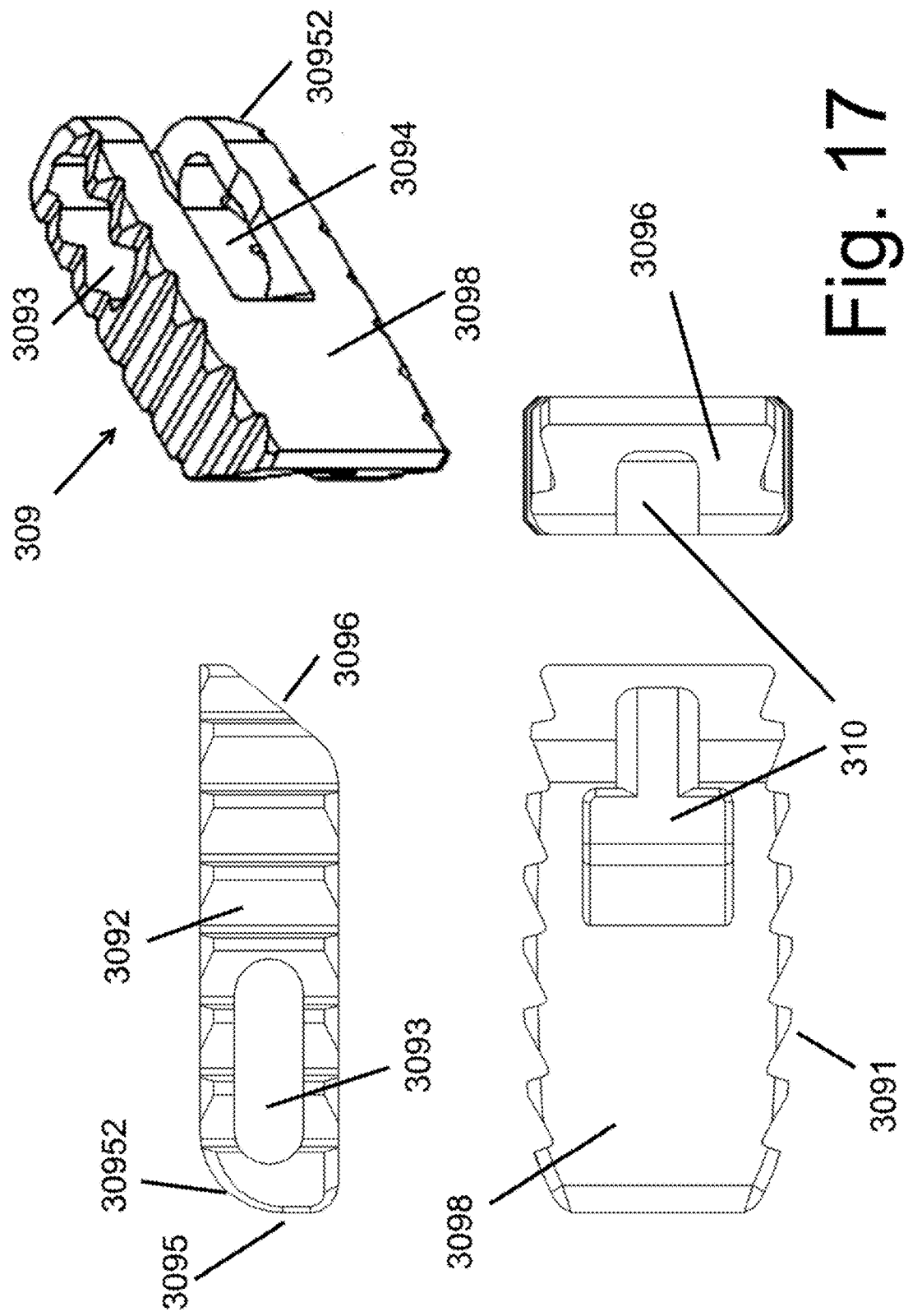
FIG. 17 is multiple views of a second member of the exemplary assembled implant according to the present disclosure.

FIG. 17 shows multiple views of member 309. There is a superior surface 3092 and inferior surface 3091, which may contain protrusions or be otherwise textured to increase fixation into the adjacent bone. Member 309 contains a front end 3095, a back end 3096 and side walls 3098. Channel 3093 extends from superior surface 3092 to inferior surface 3091. Side channel 3094 extends from a first side wall 3098 to channel 3093, but does not extend to opposing wall 3098. Channels 3093 and 3094 are configured to accept member 701. Front end 3095 contains curved segments 30952 that allow member 309 to rotate from a posterior to a side position relative to member 307—as will be discussed below. An additional channel 310 is positioned on a side wall 3098 and configured to receive a complimentary protrusion from the implant placement instrument. Channel 310 extends posteriorly and opens onto back end 3096.

Figure 18:
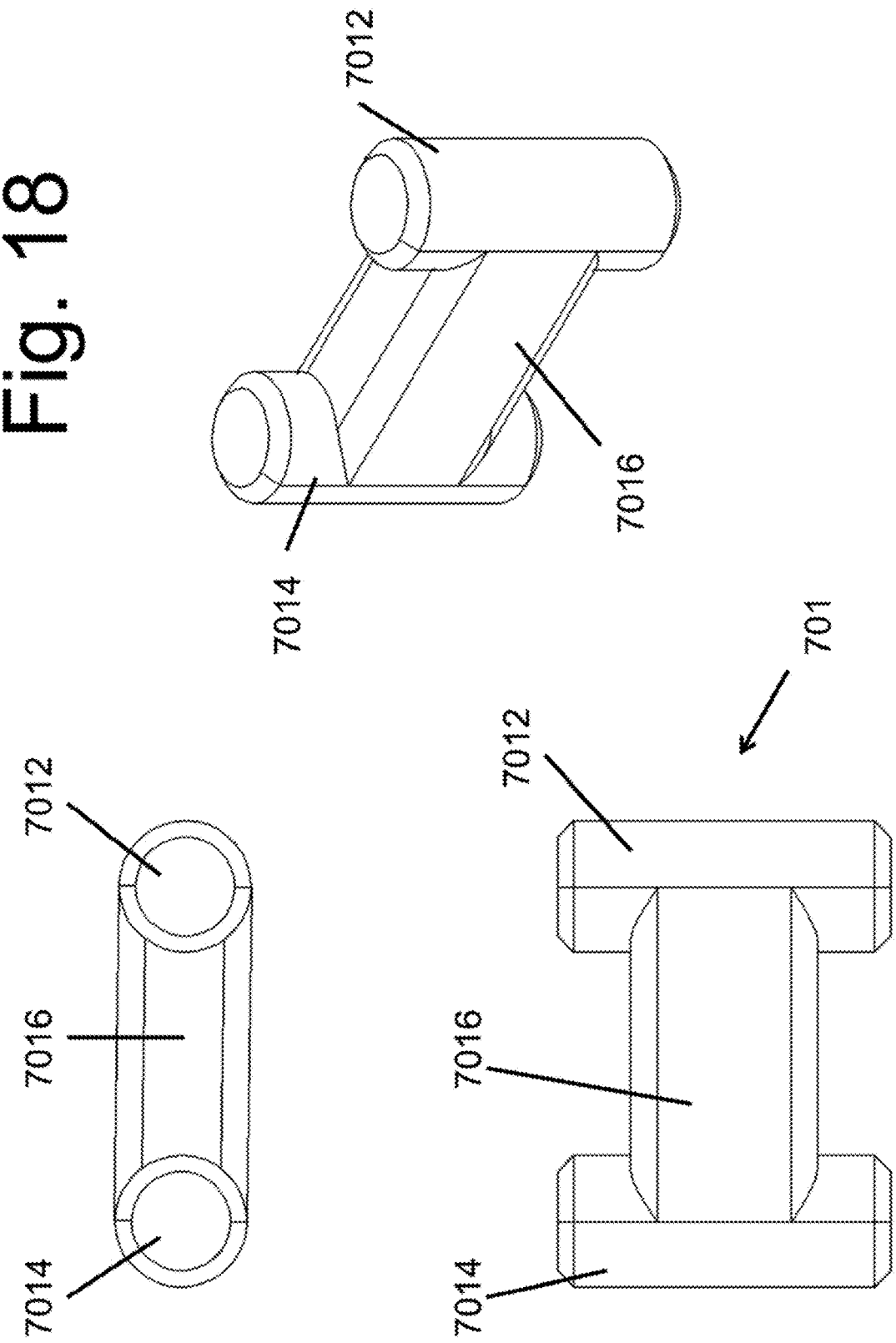
FIG. 18 is multiple views of a linkage member of the exemplary assembled implant according to the present disclosure.

FIG. 18 illustrates member 701. Member 701 is a linkage that movably couples member 307 and member 309. Each of the two end segments 7012 and 7014 are substantially cylindrical. The ends segments are connected by segment 7016. One of segments 7012 and 7014 is positioned within channel 3073 of member 307, whereas the other of segments 7012 and 7014 is positioned within channel 3093 of member 309. Segment 7016 is contained within channel 3074 of member 307 and within channel 3094 of member 309. While member 701 is illustrated as a single/unitary device, it may be alternatively made of separate components that are attached to one another.

FIG. 19 illustrates the transition of implant 301 from a first configuration (open) to a second configuration (closed). Application of a Force along direction A (FIG. 19) while holding stationary the front end 3075 of member 307 will transition the implant from the first to the second configuration. In the first configuration, member 307 and member 309 are linearly positioned with member 307 ahead of member 309, so that front end 3095 abuts back end 3076 and side surface 3078 does not abut side surface 3098. This minimizes the overall width on implant 301. In the second configuration, members 307 and 309 are positioned side by side, wherein a side surface 3078 abuts a side surface 3098. FIG. 20A shows implant 301 in the second configuration, whereas FIG. 20B shows a sectional view of the implant 301 in the second configuration. While not shown, it is further contemplated that a locking feature may be added to retain implant 301 in the second configuration. That is, a locking feature may be added to immobilize members 307 and 309 relative to one another, once the second configuration has been reached.

After member 309 is advanced from a posterior position that is outside the disc space to anterior position within the disc space and laterally displaces member 307, both members are then further displaced laterally so that the medial wall of member 309 is positioned substantially at or lateral to the medial border of the ipsilateral pedicle (plane A of FIG. 8B). At least a portion of the total implant 301 is positioned onto the lateral aspect of the apophyseal. In an embodiment, at least a portion of the lateral wall of member 307 is positioned substantially at the lateral surface of the inferior and or superior vertebral bone. Preferably, but not necessarily, a second implant 301 is placed on the contralateral side—as shown in FIG. 21. (In FIG. 21, the vertebral bone immediately inferior to the implanted disc space is show whereas the superior vertebral has been removed for diagrammatic simplicity. FIG. 21 is similar to FIG. 12B and illustrates the use of implants 301 in the method of FIGS. 10 to 12.) Bone graft 310 may be confined to the region medial to each of the implants 301 on each side of the midline or positioned at any region of space 415. Preferably, but not necessarily, the bony end plates of the upper/lower vertebral bones are not decorticated in the regions over which the implant(s) 301 are positioned.

Figure 23:
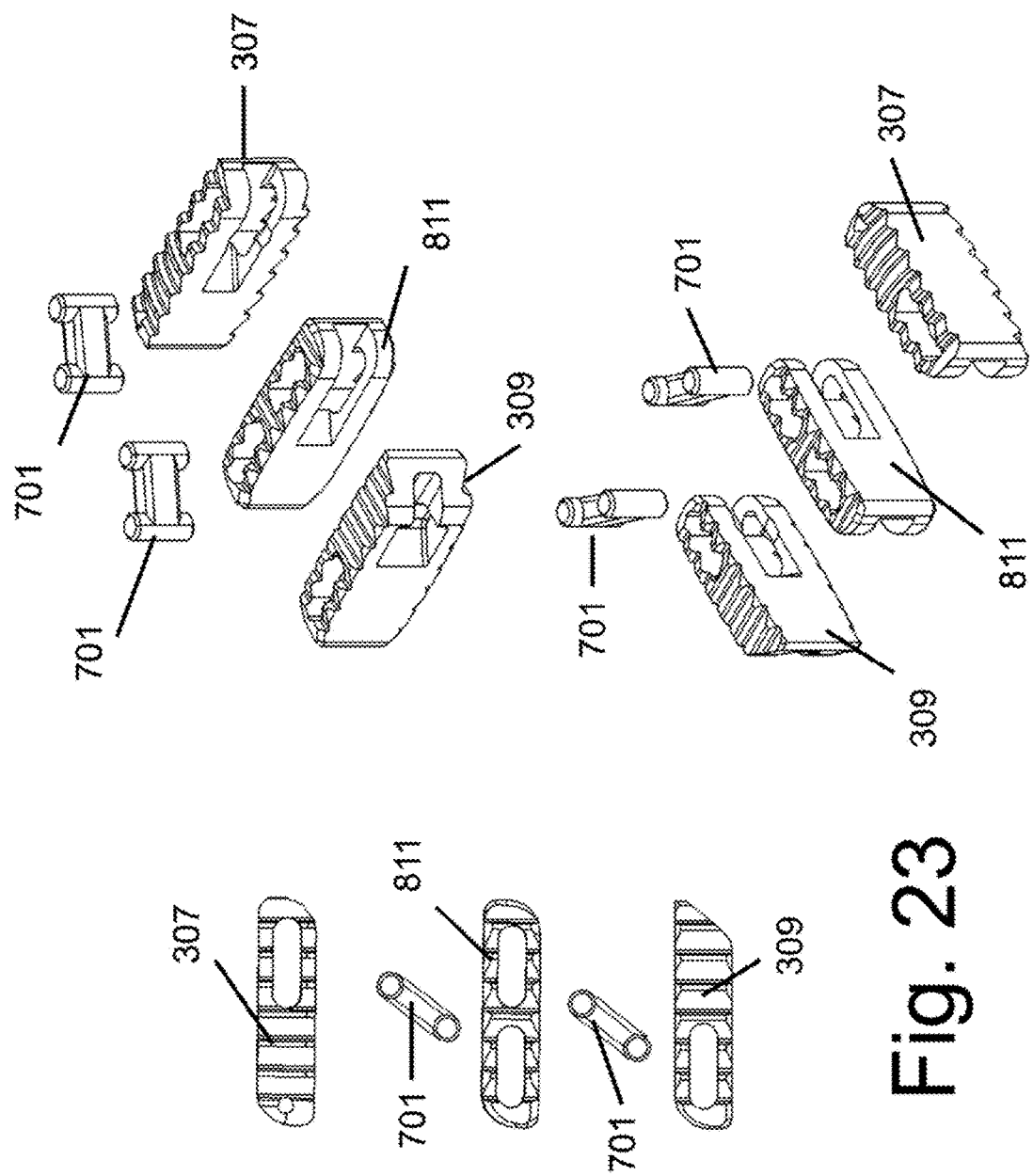
FIG. 23 is multiple exploded perspective views of the exemplary embodiment of the implant of FIG. 22.

While implant 301 is illustrated with two members (307&309), additional members may be employed to produce an implant of greater width. FIGS. 22 to 24 illustrate an implant 801 having at least three members. Implant 801 is comprised of member 307, member 309 and an intermediate member 811. (It is understood that implants of greater width may be produced by the having more than one intermediate member 811.)

FIG. 24A shows multiple views of member 811. There is a superior surface 8112 and inferior surface 8111, which may be adapted to contain protrusions or be otherwise textured to increase fixation into the adjacent bone. Member 811 contains a front end 8115, a back end 8116 and side walls 81182 and 81184. Channels 8113 extend from superior surface 8112 to inferior surface 8111. Side channel 81142 extends from a first side wall 81182 to channel 8113, but does not extend to opposing wall 81184. Side channel 81144 extends from a first side wall 81184 to channel 8113, but does not extend to opposing wall 81182.

Implants having one or more intermediate members 811 are particularly useful for placement medial (instead of lateral) to the implantation instrument 208 within the disc space. FIG. 24B is similar to FIG. 8B and illustrates a placement instrument 208 coupled to an implant 801 that has been passed into the target disc space. (Implant 801 is represented schematically in FIG. 24B). Unlike the lateral displacement of implant 105 that is illustrated in FIG. 9A, implant 801 is displaced medially (i.e., towards the vertebral midline) as shown in FIG. 24C. After removal of the placement instrument 208, bone forming material (which may include e.g., autograft and/or allograft bone) 310 is placed lateral to the medially displaced implant 801. As disclosed above, the placement instrument may be manually held by the operating surgeon, and/or configured to be anchored onto a segment of the adjacent vertebral bone(s) (such as, for example, to the pedicle portion), and/or anchored to the operating room table onto which the patient is positioned. FIGS. 24D and 24E illustrate the implant 801 and graft material 310 positioned within the target disc space. (Note that the superior vertebral bone has been removed to uncover the disc space for ease of illustration.)

An additional embodiment is disclosed in FIGS. 25 to 33. In this embodiment at least one intermediate member is positioned between the front-most member and the back-most member. While similar to member 811 of the prior embodiment, the intermediate members differs in that the axis of each of the center channels (i.e., channels 8113 in member 811) are substantially aligned at a right angle to one another when viewed in along direction of the longitudinal axis of the intermediate member. This allows the implant to expand in both height and width as it transitions from the open to the closed configurations—as will be shown further bellow.

Figure 25:
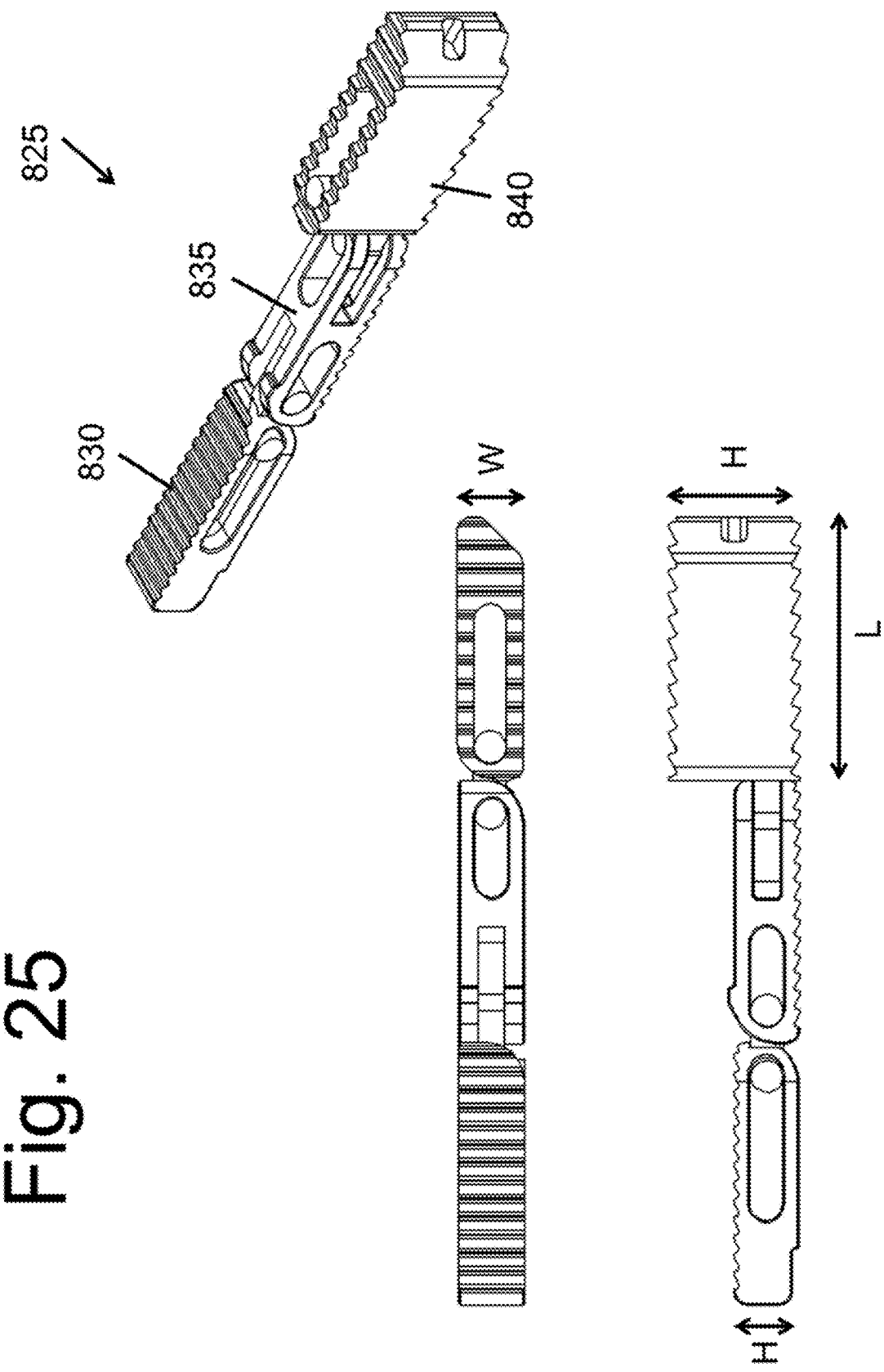
FIG. 25 is multiple views of another exemplary embodiment of an implant according to the present disclosure shown in an open configuration.
Figure 26:
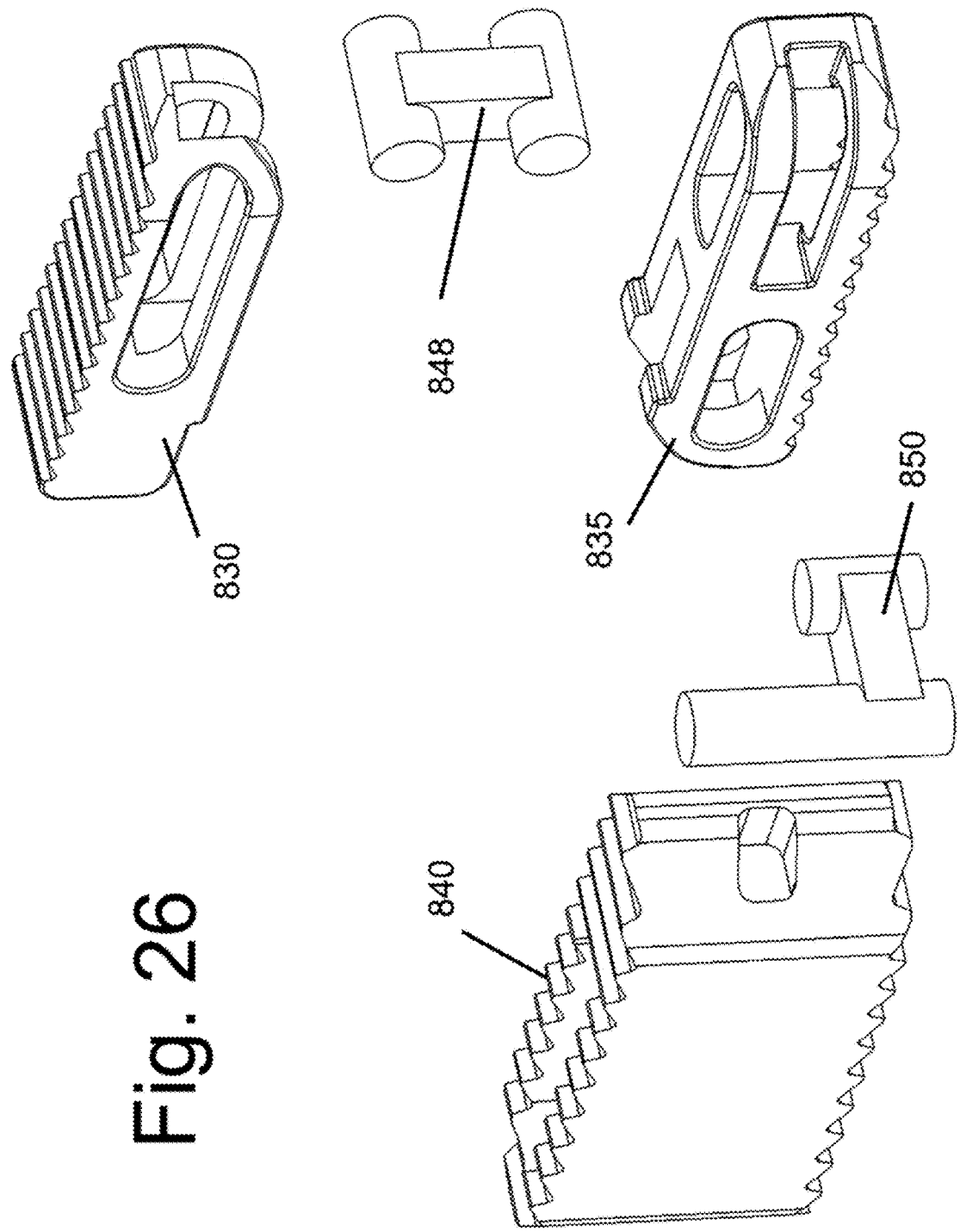
FIG. 26 is an exploded a view of the exemplary implant of FIG. 25.

FIG. 25 illustrates implant 825 in the open configuration. Implant 825 has a front most member 830, an intermediate member 835 and back-most implant 840. Each of the members has a height H, a length L and width W. While these dimensions may vary between the members, in an embodiment, the length and width of all three members are substantially equal. The height of member 840 is substantially equal to the height of member 830 when added to the height of member 835. FIG. 25 shows implant 825 in the open configuration with member 830, 835 and 840 arranged in a linear configuration. FIG. 26 shows an exploded view. As in prior embodiments that were disclosed above, the members on implant 825 are coupled using connecting members 848 and 850. Connector members 848 and 850 are similar to member 701 and substantially differ only in the dimensions of the constituent segments.

Figure 27:
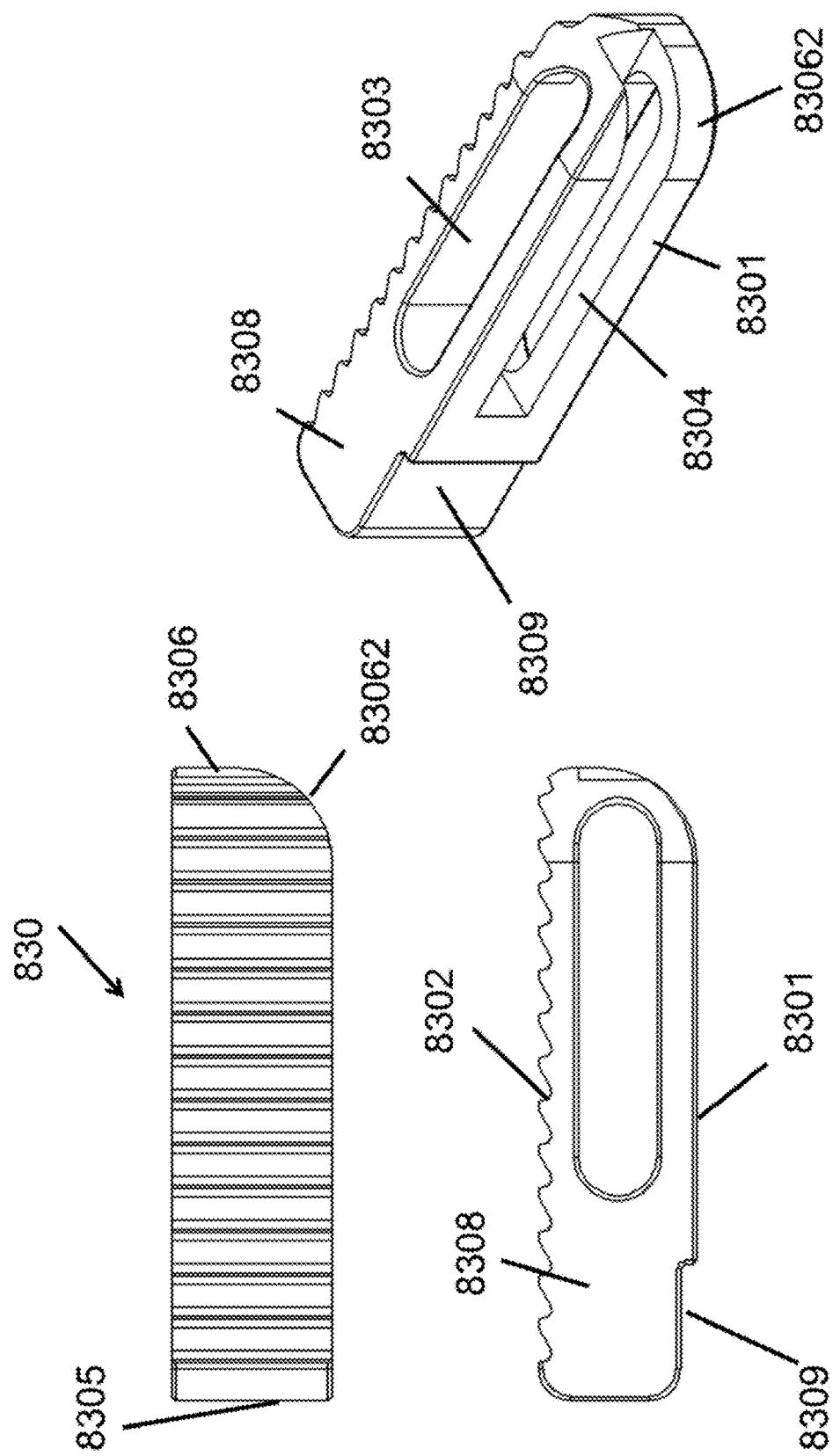
FIG. 27 is multiple views of a first member of the exemplary implant of FIG. 25.

FIG. 27 illustrates member 830. There is a superior surface 8302, which in one embodiment, contains protrusions or is otherwise textured to increase fixation into the adjacent bone. Member 830 contains a front end 8305, a back end 8306 and side walls 8308. Channel 8303 extends from one side wall 8308 to the other side wall. Channel 8304 extends from inferior surface 8301 to channel 8303, but does not extend to the superior surface 8302. Channels 8303 and 8304 are configured to accept member 848. Back end 8306 contains curved segments 83062 that allow member 830 to rotate from a anterior to a superior position relative to member 835—as will be discussed below. An anterior cutout 8309 accommodates complimentary protrusion 8359 of member 835 to form a locking feature.

Figure 28:
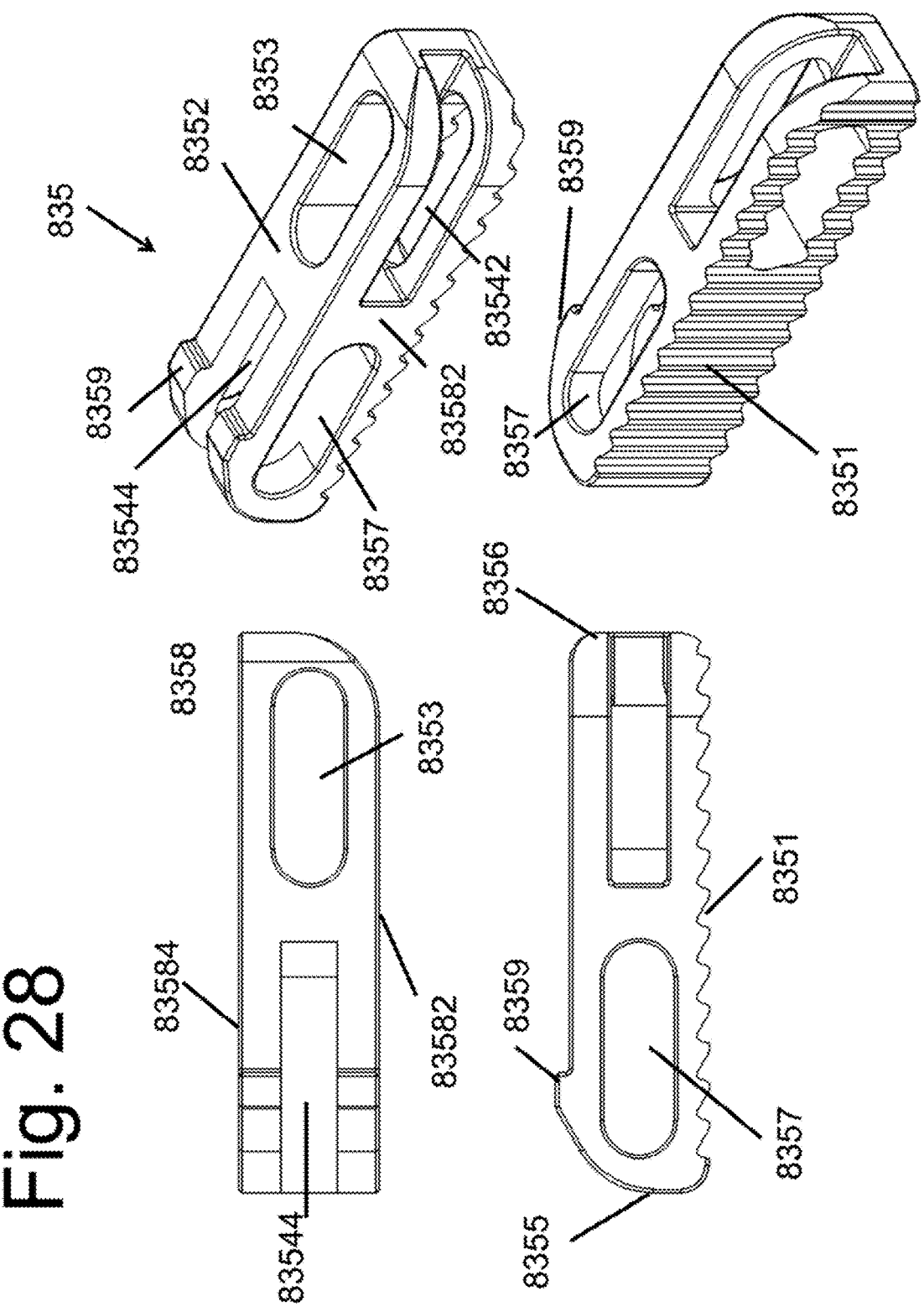
FIG. 28 is multiple views of a second member of the exemplary implant of FIG. 25.

FIG. 28 shows multiple views of member 835. There is a superior surface 8352 and inferior surface 8351. The latter may be adapted to, in one embodiment, contain protrusions or be otherwise textured to increase fixation into the adjacent bone. Member 835 contains a front end 8355, a back end 8356 and side walls 83582 and 83584. Channel 8353 extends from superior surface 8352 to inferior surface 8351. Side channel 83542 extends from a first side wall 83582 to channel 8353, but does not extend to opposing wall 83584. Channel 8357 extends from side wall 83582 to 83584. Side channel 83544 extends from superior surface 8352 to channel 8357 but does not extend to the inferior surface. Protrusion 8359 extends from superior surface 8352.

Figure 29:
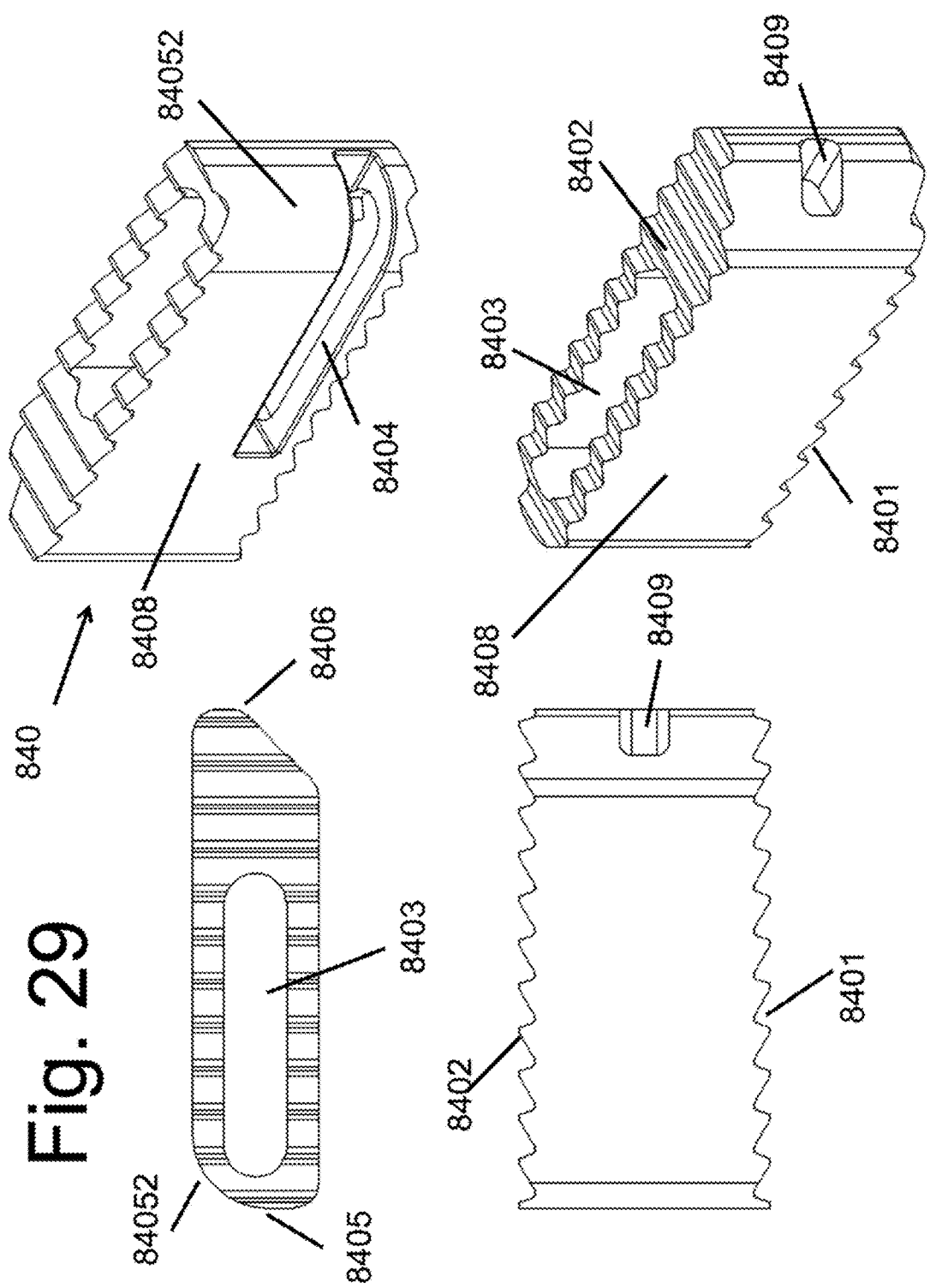
FIG. 29 is multiple views of a third member of the exemplary implant of FIG. 25.

FIG. 29 shows multiple views of member 840. There is a superior surface 8402 and inferior surface 8401, which contain protrusions or are otherwise textured to increase fixation into the adjacent bone in one embodiment. Member 840 contains a front end 8405, a back end 8406 and side walls 8408. Channel 8403 extends from superior surface 8402 to inferior surface 8401. Side channel 8404 extends from a first side wall 8408 to channel 8403, but does not extend to opposing wall 8408. Channels 8403 and 8404 are configured to accept member 850. Front end 8405 contains curved segments 84052 that allow member 840 to rotate from a posterior to a side position relative to member 835—as will be discussed below. An indentation 8409 is positioned on a back end 8406 and configured to receive a complimentary protrusion from an implant placement instrument.

Figure 30:
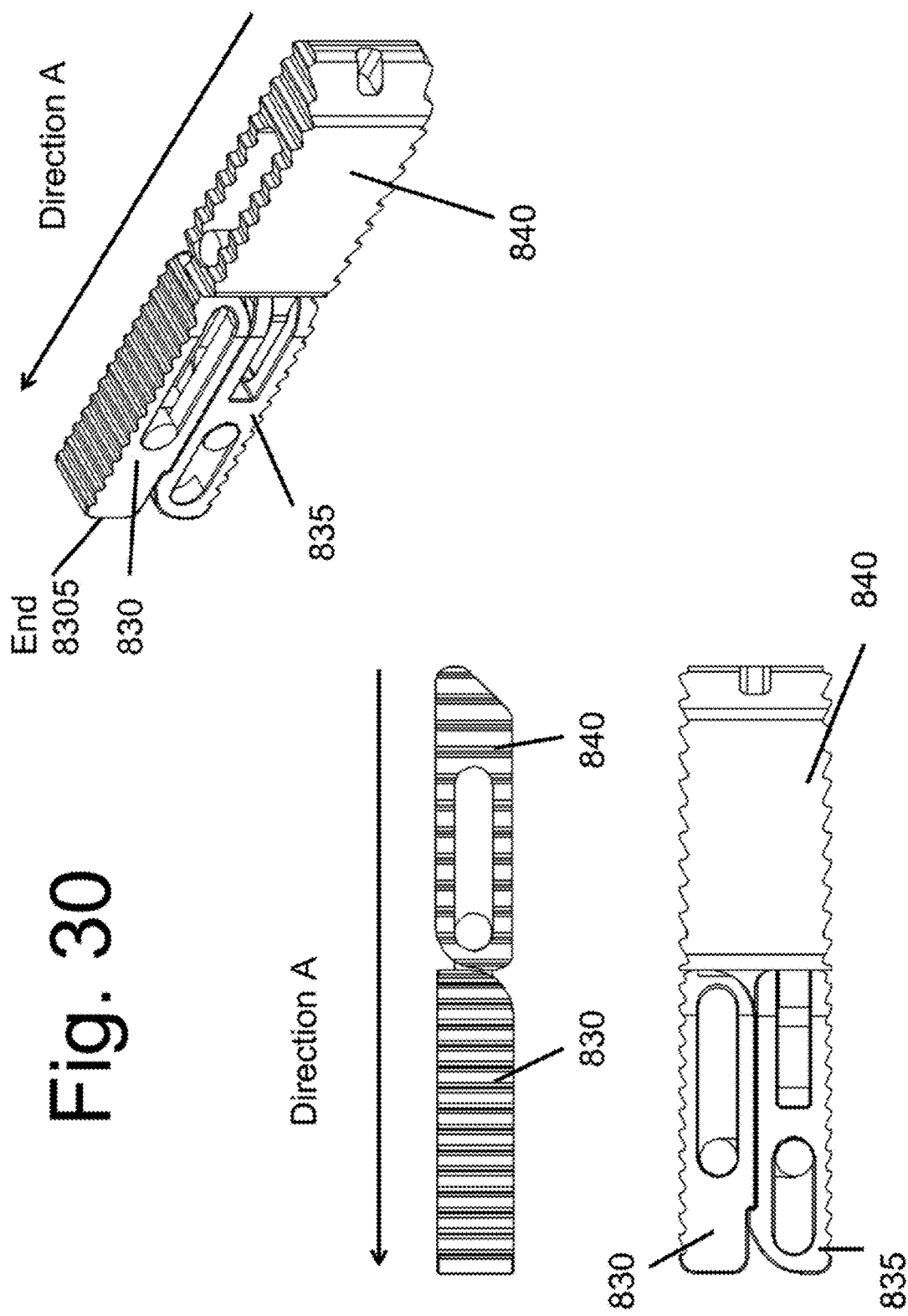
FIG. 30 is multiple views of transitioning of the exemplary implant from an open configuration to a closed configuration.
Figure 31:
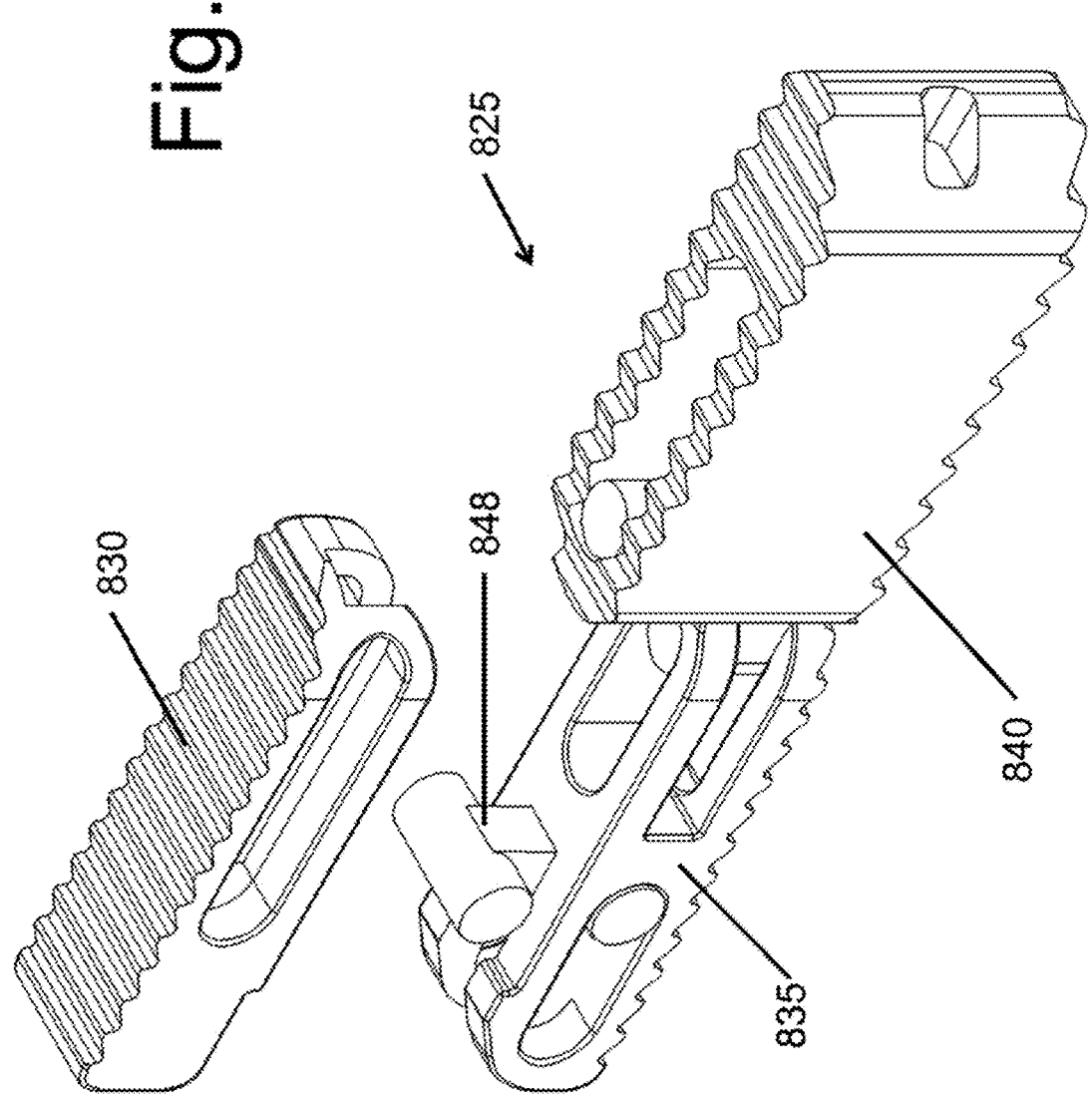
FIG. 31 is a partially exploded view illustrating the positioning of a first member of the exemplary implant.

Application of a Force along direction A (FIG. 30) while holding stationary the front end 8305 of member 830 will produce transition of implant 825 from the first (open) to the second (partially closed) configuration. In the latter, member 830 will forcibly rotate from a position in front of member 835 to a position on top of member 835—as shown in FIG. 30. FIG. 31 is a partially exploded view intended to illustrate the position of member 848. Protrusion 8359 extends from superior surface 8352 and will become positioned within cutout 8309 of member 830. This provides a locking feature that resists the forward migration of member 830 relative to member 835. (Note that, at this point of the transition of the implant 825, the placement instrument prevents member 840 from rotating to the side of member 835.)

Figure 33:
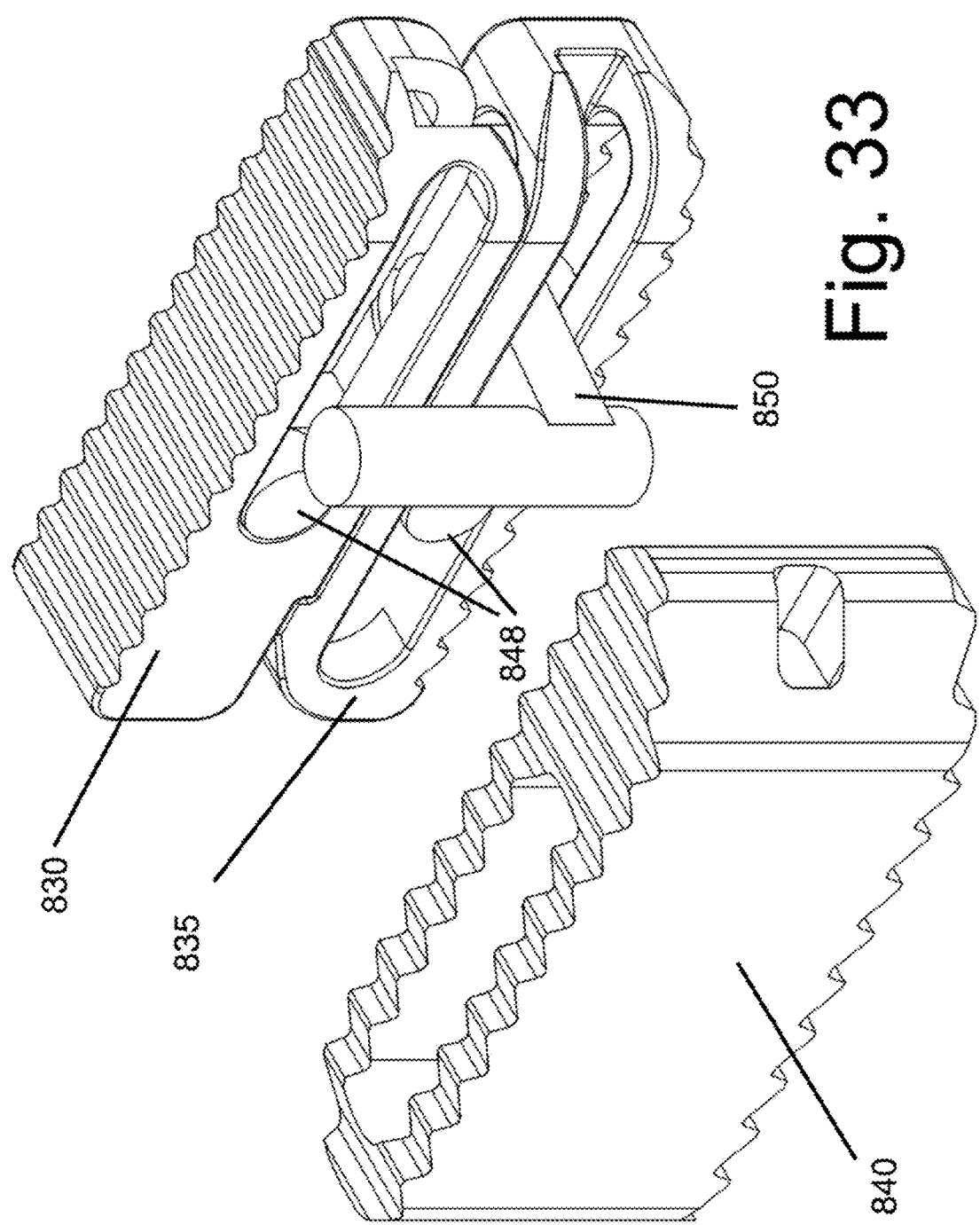
FIG. 33 is a partially exploded view illustrating the positioning of a second member of the exemplary implant.

At this point, the placement instrument will allow member 840 to rotate from a position posterior to member 835 to a position besides member 835—as is shown in FIG. 32. (FIG. 33 is a partially exploded view intended to illustrate the position of member 850.) Note that this step allows the implant to transition from the second configuration (partially closed) to a third configuration (fully closed) and is similar in action to the transition of implant 301 from the first configuration (open) to the second configuration (closed) that was described previously. While not shown, it is further contemplated that a locking feature may be added to retain implant 825 in the third configuration. That is, a locking feature may be added to immobilize members 840 and 835 relative to one another, once the third configuration has been reached.

In use of implant 825, member 830 is advanced into disc space wherein the space needed for implant advancement is that of the width and height of member 830. With transition into the second configuration (partially closed) of implant 825, the implant height expands to that of the sum of the height of members 830 and 835. With transition into the third configuration (fully closed), the implant width expands to that of the sum of the width of members 840 and the width of the member 835 or 830 with the greater width. In this way, implant 825 expands in both height and width after implantation into the disc space.

An additional embodiment 505 is illustrated in a side and an oblique view (FIG. 34A), wherein implant 505 is in an expanded configuration. Implant 505 is comprised of a variable number of foldable regions 5052 and interconnecting regions 5054. An end segment 5056 is poisoned at a first end and an end segment 5058 is positioned at an opposing end. When end segments 5056 and 5058 are forcibly moved towards one another (as in direction K of FIG. 34B), the foldable regions 5052 increase in diameter (dimension M) and decrease in length (dimension N) to produce the folded configuration shown in FIG. 34B. Note that foldable regions are placed on one side of the interconnection segments 5054 in one embodiment. That is, when considered in the direction of dimension M (FIG. 34A), implant 505 has foldable regions on one side and interconnecting regions on the other side of the implant. With transition to the folded configuration, all foldable regions 5052 remain on the same side of the interconnecting segments 5054.

In use, the implant 505 is positioned in the disc space through the space lateral to the thecal sac and substantially medial to the pedicle of the inferior vertebral bone. The implant is placed into the disc space while in the expanded configuration shown in FIG. 34A. A force is applied to implant 505 so as to transition the implant into the folded configuration of FIG. 34B. The instrumentation that guides the implant into the disc space and applies the force needed to transition the implant into the folded configuration (instrumentation not shown) may also be adapted to permit the folding of the most distal foldable regions 5052 first (closer to distal end 5056) so as to have only the portion of the implant already within the disc space fold while that portion exterior to the disc space remain in the extended (non-folded) state. Once a foldable segment 5052 is in the disc pace, then it is permitted to fold by the placement instrumentation. When positioned into the disc space and deployed into the folded configuration, it is the lateral (side) surfaces (such as 50542 and 50522) of the implant that abut the adjacent vertebral bone and bear the load that is transmitted through the disc space.

Expandable interbody spacers are known in the art and include disclosures of U.S. Pat. No. 6,86,673; U.S. Patent Application Publication Nos. 2011/0213465, and 2011/0251693, and others; each of which is incorporated herein by reference in its entirety. In at least some of these devices, the spacer is expanded by the addition of at least one or more stackable segments within the implant. FIG. 35A shows side and end-on views of generic expandable implant 705 that is adapted to expand along direction "E" after implantation into the target disc space. With expansion, the disc space is distracted and its height is increased. The expanded implant is shown in FIG. 35B. Note that the implant is positioned within the disc space with the axis of expansion "E" being substantially in the direction of the long axis (i.e., caudad-cephalad) of the spinal column. In this way, surface 7052 would abut the inferior surface of the vertebral bone immediately superior to the implanted disc space. Likewise, surface 7054 would abut the superior surface of the vertebral bone immediately inferior to the implanted disc space.

In the current disclosure, an implant 705 is positioned into the disc space on at least one side of the vertebral mid-sagittal plane. (In one particular embodiment, the implants are placed bilaterally.) The implant is positioned with the axis of expansion "E" being substantially in the direction of the horizontal axis of the implanted disc space. In this way, a first side surface 7056 abuts the inferior surface of the superior vertebral bone and the opposing side surface 7056 abuts the superior surface of the inferior vertebral bone. FIG. 36A shows the implant 705 being introduced into the target disc space through a posterior trajectory "A", wherein the lateral surface of the implant is positioned substantially at the medial aspect of the pedicle of the inferior vertebral bone (plane "A" of FIG. 8B). Implant 705 is expanded laterally within the disc space along axis of expansion "E". The implant may also be displaced laterally within the disc space so that the lateral aspect of the implant is at least positioned to overlay the lateral aspect of the apophyseal ring, and, to rest substantially at the very lateral extent of the disc space in one variant—as shown in FIG. 36B. (Note that the sequence of implant expansion and translation may be interchangeable.) FIG. 37 shows the implants positioned bilaterally, as would be the configuration in one particular embodiment.

In an alternative embodiment, each of one implant 755 is advanced through a posterior corridor via trajectory "A" into the disc space (FIG. 38A). The implant is rotated laterally on each side (FIG. 38B) and a second implant 775 is positioned via trajectory "A" into the disc space (FIG. 39A). Each implant 775 is translated laterally so that its medial border is substantially aligned with plane "A" of FIG. 8B (FIG. 39B). Implant 755 and 775 may be attached to one another after intra-discal implantation, before intra-discal implantation, or not at all.

Figures 40A, 40B:
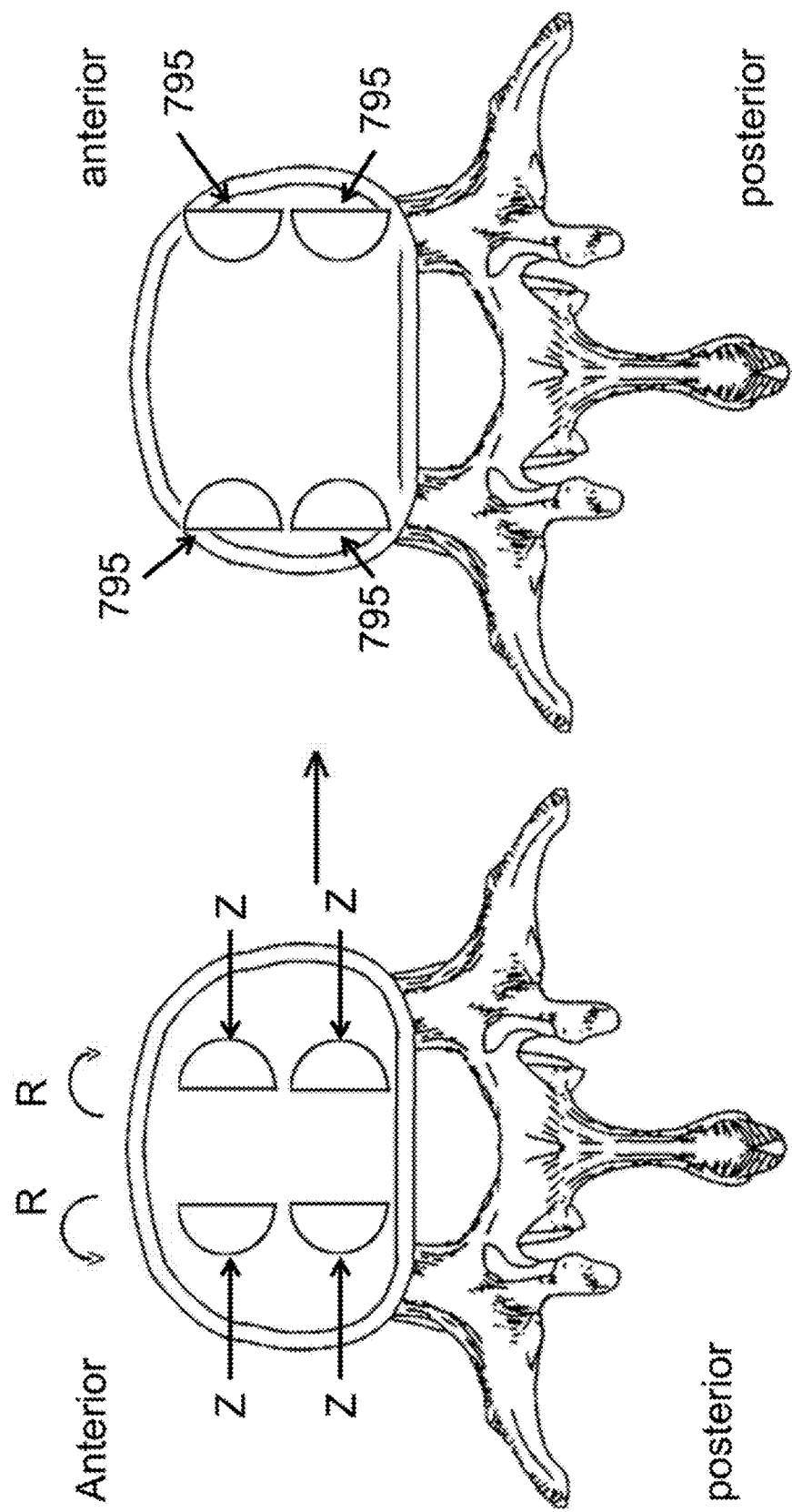
FIG. 40A is a superior view of the two first and the two second exemplary implants prior to a rotation thereof.
FIG. 40B is a superior view of the two first and the two second exemplary implants of FIG. 40A after rotation thereof.

In another embodiment, one or more implants 795 are positioned into the disc space through a posterior corridor via trajectory "A" (of FIG. 40A) into the disc space. Each implant is rotated about a center of rotation "Z" that is centered substantially at the lateral surface of the implant. In one variant, the procedure is performed bilaterally. FIG. 40A shows the implants 795 prior to rotation, wherein the lateral implant surface is substantially aligned with plane "A" of FIG. 8B. FIG. 40B illustrates the implants after rotation, wherein the medial border of one or more implants is substantially aligned with plane "A" of FIG. 8B. As disclosed previously, bone forming material can then be placed within the space between the medial aspect of the implants on one side of the vertebral midline (i.e., mid-sagittal plane) and the medial aspect of the implants on opposing side of the vertebral midline. It should be understood that bone forming material may be placed medial to the laterally positioned implants in any of the disclosed embodiments of this application.

Preferably, but not necessarily, supplemental fixation of the implanted FSU is placed in order to rigidly immobilize the superior and inferior vertebral bones. Pedicle screw immobilization can be employed by the placement of a bone screw into the posterior aspect of the ipsilateral pedicle of each of the superior and inferior vertebral bones (a screw enters each of the bones at or about 811 of FIG. 1B). The two screws are then rigidly interconnected by a third member, such as a rod or plate. The procedure may be repeated on the contra-lateral side. Pedicle screw fixation of adjacent vertebral bones is well known in the art and is disclosed in U.S. Pat. No. RE 37665, U.S. Patent Application Publication No. 2006/0084981, and many others. (The enumerated art is incorporated by reference in its entirety).

As an alternative (or in addition) to pedicle screw fixation, a spinous process fixation implant may be used for supplemental fixation. A generic spinous process fixation implant is illustrated in FIG. 41. Implant 605 is comprised of first member 610 and opposing member 612 that are configured to be attached onto opposing (contra-lateral) sides of two adjacent vertebral bones. The spinous processes are forcibly captured between member 610 and 612. An interconnecting member 615 is then locked relative to members 610 and 612 and prevents them from moving away from one another. Projections 617 penetrate the spinous processes and increase bone fixation of member 610 and 612.

Figure 43:
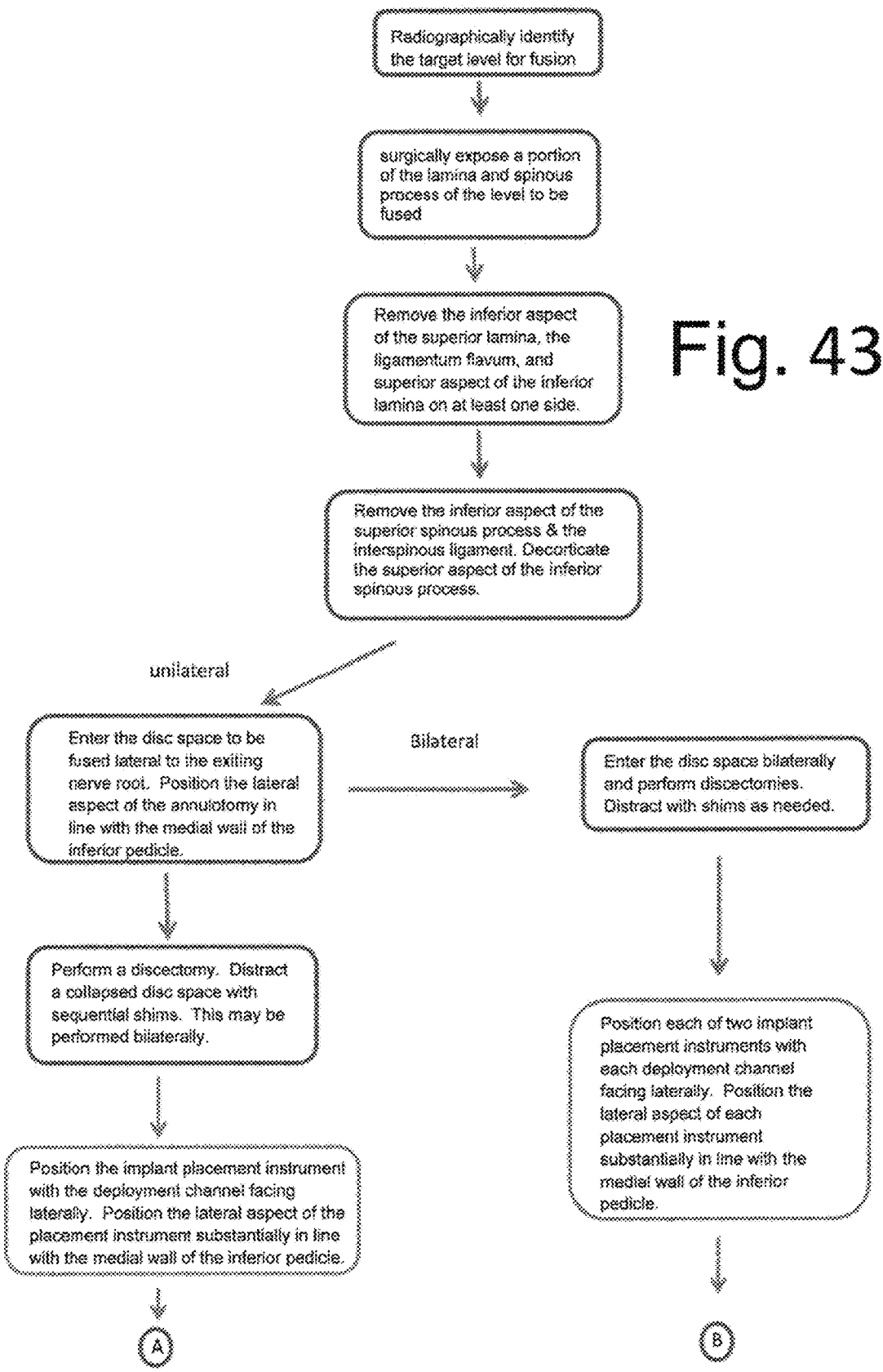
FIG. 43 is a logical flow diagram of a method for implantation of an implant according to the present invention.
Figure 43:
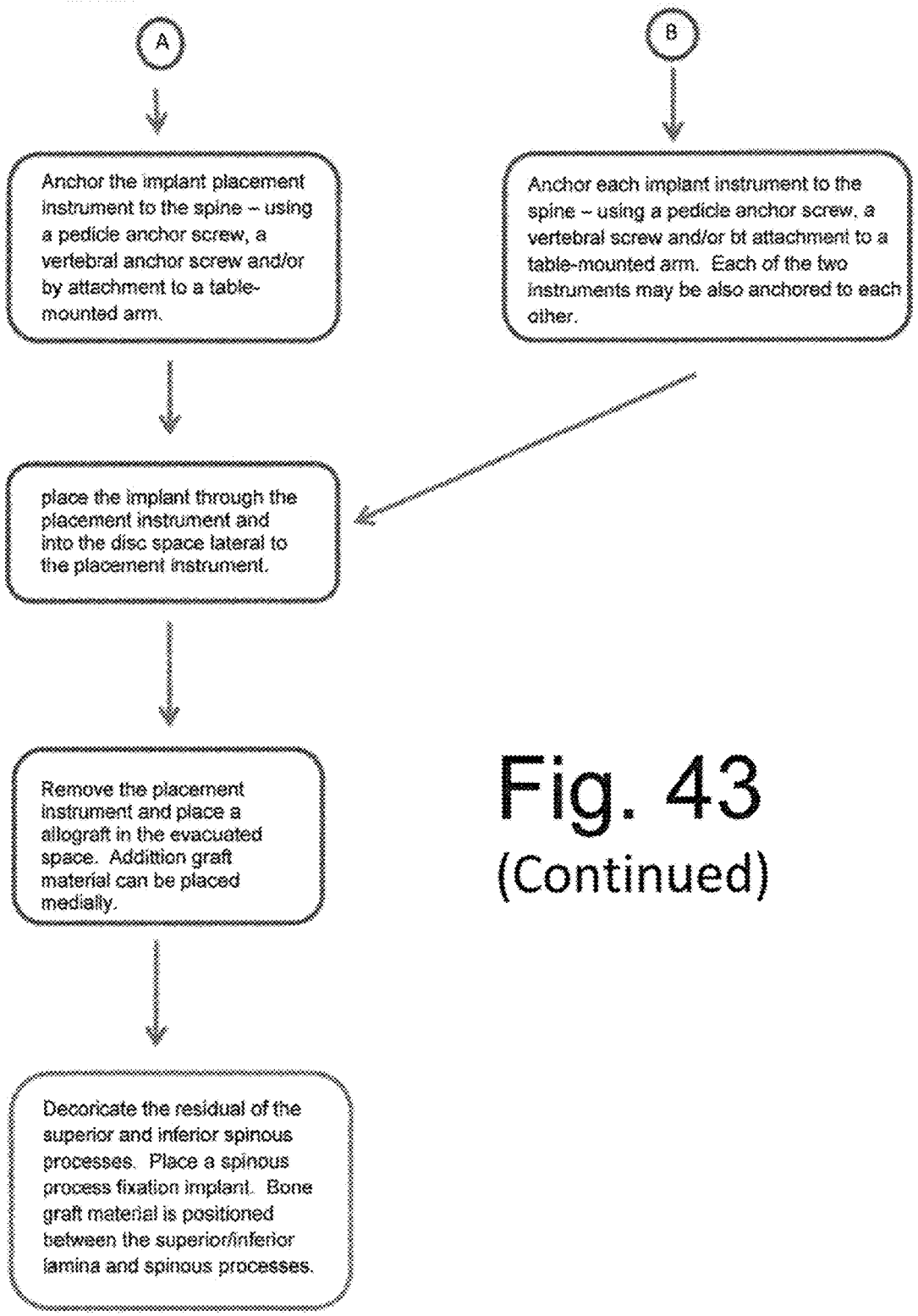

FIGS. 42A and 42B show a lateral and axial view of the implanted FSU. Note that the interbody device is, in one variant, placed bilaterally. In the axial plane (FIG. 42B), the interbody devices provide two anterior column supports while plate 605 provides a posterior midline support. In the lateral view (FIG. 42A), the interbody implant forms an anterior abutment surface and plate 605 forms posterior abutment surface. In this way, the implant assembly forms a balanced three-point support of the vertebral bones. Additional bone graft material may be placed between the spinous process and/or lamina of the superior and inferior vertebral bones after appropriate decortication of the bone at the intended graft recipient site. FIG. 43 provides a stepwise overview of the procedure for implantation of at least implant 301—as well as others.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

It will be recognized that while certain embodiments of the disclosure are described in terms of a specific sequence of steps of a method, these descriptions are only illustrative of the broader methods, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure and claimed herein.

While the above detailed description has shown, described, and pointed out novel features as applied to various embodiments, it will be understood that various omissions, substitutions, and changes in the form and details of the device or process illustrated may be made by those skilled in the art without departing from the contents of the disclosure. The foregoing description is of the best mode presently contemplated. This description is in no way meant to be limiting, but rather should be taken as illustrative of the general principles embodied herein. The scope of the present disclosure should be determined with reference to the claims.

What is claimed is:

1. A device sized to be at least partially implanted within an intervertebral disc space, the device comprising:
   a first member that comprises:
   (i) a first top surface and an opposing first bottom surface that are connected by at least a first side surface;
   (ii) a first internal channel extended along an axis extended from said first top surface to the opposing first bottom surface;
   (iii) a first front surface and a first back surface, the first member extended from said first front surface to the first back surface along a first longitudinal axis; and
   (iv) a second internal channel extended from said first back surface to intersect said first internal channel;
   a second member that comprises:
   (i) a second top surface and an opposing second bottom surface that are connected by at least a second side surface; and
   (ii) a second front surface and a second back surface, the second member extended along a second longitudinal axis from the second front surface to the second back surface; and
   a linkage that comprises:
   (i) a first portion that is configured to be at least partially received within said first internal channel of the first member, and is sized to translate therein; and
   (ii) a second portion extended away from the first portion along a third longitudinal axis of the linkage, said second portion being at least partially received within said second internal channel of the first member;
   wherein the device is configured to transition from a first configuration to a second configuration, the first configuration comprising:
   (i) said first back surface of the first member positioned to face said second front surface of the second member; and
   (ii) the third longitudinal axis of the second portion of the linkage positioned to be at least one of parallel or colinear to said first longitudinal axis of the first member; and
   the second configuration comprising:
   (i) the third longitudinal axis of the second portion of the linkage positioned non-parallel and non-colinear to said first longitudinal axis of the first member; and
   wherein said transition between the first configuration and the second configuration produces movement of said linkage relative to said first member, said movement comprising:
   (i) a rotation of said first portion of the linkage around the axis that extends from said first top surface to said opposing first bottom surface of the first member; and
   (ii) a translation of the first portion of the linkage within said first internal channel of the first member.

2. The device of claim 1, wherein, in the first configuration, the first member and the second member are aligned such that the first longitudinal axis of the first member and the second longitudinal axis of the second member are collinear.

3. The device of claim 1, wherein, in the second configuration, the first side surface of the first member is positioned to face the second side surface of the second member.

4. The device of claim 1, wherein the second member further comprises a first internal cavity extended from a first opening of the second top surface to a second opening of the opposing second bottom surface.

5. The device of claim 1, wherein the first back surface of the first member comprises a curvilinear segment extended onto the first side surface.

6. The device of claim 5, wherein said first configuration further comprises said second front surface of the second member abutted to said first back surface of the first member.

7. The device of claim 6, wherein said transition of the device from the first configuration to the second configuration comprises advancement of the second front surface of the second member along the curvilinear segment of the first back surface of the first member.

8. The device of claim 1, wherein the first member further comprises a third channel extended outwardly from said first internal channel and opens onto said first side surface.

9. The device of claim 8, wherein the third channel is sized to receive the second portion of the linkage therein.

10. The device of claim 9, wherein the third channel intersects the second internal channel.

11. The device of claim 10, wherein the second portion of the linkage is configured to translate from the second internal channel to the third channel.

12. A device configured for implantation at least partially within an intervertebral disc space, the device comprising:
   a first member that comprises a first top surface and an opposing first bottom surface that are connected by a first side surface, the first member extended from a first front surface to a first back surface along a first longitudinal axis;
   a second member that a second top surface and an opposing second bottom surface that are connected by a second side surface, the second member extended from a second front surface to a second back surface along a second longitudinal axis; and
   a linkage apparatus configured to enable transition of the device from a first configuration to a second configuration;
   wherein the first member further comprises a first elongated channel disposed therein, the first elongated channel configured to enable translation of at least a first portion of the linkage apparatus therein; and
   wherein:
      (i) in the first configuration, the first member and the second member are positioned in a linear configuration such that:
         (a) said first back surface of the first member faces said second front surface of the second member; and
         (b) said first longitudinal axis of the first member and said second longitudinal axis of the second member are colinear; and
      (ii) in the second configuration, said first longitudinal axis of the first member and said second longitudinal axis of the second member are non-colinear.

13. The device of claim 12, wherein the linkage apparatus comprises the first portion configured to couple to said first member, a second portion configured to couple to said second member, and an interconnecting portion that couples the first portion and the second portion.

14. The device of claim 13, wherein the first elongated channel is configured for communication with a first opening formed within the first top surface and a second opening formed within the opposing first bottom surface of the first member.

15. The device of claim 14, wherein the first portion of the linkage apparatus comprises a first elongated member configured to be at least partially seated within said first elongated channel.

16. The device of claim 15, wherein the first member further comprises a first aperture of disposed in the first side surface and a second aperture disposed in the first back surface, each of said first aperture and said second aperture being (i) sized to receive the interconnecting portion of the linkage apparatus, and (ii) configured to intersect at least a portion of the first elongated channel of the first member.

17. The device of claim 16, wherein the second aperture intersects the first aperture such that the first member is configured to enable the interconnecting portion of the linkage apparatus to translate between the second aperture and the first aperture.

18. The device of claim 15, wherein the second member comprises a second elongated channel extended from a third opening formed within the second top surface to a fourth opening formed within the second bottom surface of the second member; and
   the second portion of the linkage apparatus comprises a second elongated member, the second elongated channel configured to at least partially seat the second elongated member of the second portion of the linkage apparatus therein.

19. The device of claim 18, wherein the second member further comprises an aperture disposed in the second side surface, the aperture sized to at least partially receive said interconnecting portion of the linkage apparatus, said aperture intersecting at least a portion of the second elongated channel and intersecting at least a portion of the second front surface of the second member.

20. The device of claim 13, wherein the transition of the device from the first configuration to the second configuration produces a movement of the first portion of said linkage apparatus relative to the first member, the movement comprising:
   (i) a rotation of the first portion of the linkage apparatus about an axis that extends from said first top surface to said first bottom surface of the first member; and
   (ii) a translation of the first portion of the linkage apparatus from a first point to a second point through the first elongated channel of the first member in a direction of the first longitudinal axis of the first member.

21. A device configured to be at least partially implanted within an intervertebral disc space, the device comprising:
   a first member that comprises a first top surface and an opposing first bottom surface that are connected by a first side surface, the first member extended from a first front surface to a first back surface along a first longitudinal axis, the first member further comprising a slot;
   a second member comprising a second top surface and an opposing second bottom surface that are connected by a second side surface, the second member extended from a second back surface to a second front surface along a second longitudinal axis; and
   a linkage comprising:
      (i) first portion that is at least partially received within the slot of the first member and is configured to translate therein;
      (ii) a second portion configured to couple to the second member; and
      (iii) an interconnecting portion that connects said first portion and said second portion;
   wherein, the device is configured to transition between a first configuration and a second configuration, in said first configuration:
      (i) the first member and the second member are positioned such that the first longitudinal axis is colinear with the second longitudinal axis; and
      (ii) a force aligned with the second longitudinal axis and applied to the second back surface of the second member produces an initial rotation and a subsequent translation of the second front surface of the second member relative to a stationary position of the first back surface of the first member.

22. The device of claim 21, wherein the slot of the first member comprises a first internal cavity extended from said first top surface to said opposing first bottom surface of the first member, the first internal cavity configured to seat a first elongated member of the first portion of the linkage.

23. The device of claim 22, wherein the first member further comprises a first aperture of within the first side surface and a second aperture within the first back surface, each of the first aperture and the second aperture being sized to receive the interconnecting portion of the linkage, and configured to intersect at least a portion of the first internal cavity of the first member.

24. The device of claim 23, wherein the second aperture intersects the first aperture such that the first member is configured to enable the interconnecting portion of the linkage to translate between said second aperture and said first aperture.

25. The device of claim 24, wherein the second member comprises a second internal cavity extended from a first opening of the second top surface to a second opening of the second bottom surface of the second member, the second internal cavity of the second member configured to seat a second elongated member of the second portion of the linkage.

26. The device of claim 25, wherein said second member further comprises a third aperture within the second side surface and a fourth aperture within the second front surface, each of the third aperture and the fourth aperture sized to receive the interconnecting portion of the linkage, and configured to intersect at least a portion of the second internal cavity of the second member.

27. The device of claim 26, wherein the fourth aperture intersects the third aperture such that the second member is configured to enable the interconnecting portion of the linkage to translate between the fourth aperture and the third aperture.

28. The device of claim 27, wherein, in the first configuration, the interconnecting portion of the linkage is at least partially positioned within each of the second aperture of the first member and the fourth aperture of the second member.

29. The device of claim 27, wherein, in the second configuration, the interconnecting portion of the linkage is at least partially positioned within each of the first aperture of the first member and the third aperture of the second member.

30. A device configured to be at least partially implanted within an intervertebral disc space, the device comprising:
a first member extended from a first front surface to a first back surface along a first longitudinal axis, the first member comprising a first top surface, an opposing first bottom surface, and a first side surface, the first member further comprising:
(i) a slot extended from a first opening within said first top surface to a second opening within said opposing first bottom surface; and
(ii) a first aperture of said first back surface that intersects the slot;
a second member extended from a second front surface to a second back surface along a second longitudinal axis, the second member comprising a second top surface, an opposing second bottom surface, and a second side surface; and
a linkage comprising:
(i) first portion that is at least partially received within the slot of the first member and is configured to translate therein; and (ii) a second portion extended away from the first portion along a third longitudinal axis, the second portion configured to be at least partially received within the aperture of the first member;
wherein, in a first device configuration, the third longitudinal axis of the second portion of the linkage is positioned to be colinear with the first longitudinal axis of the first member; and
wherein, in a second device configuration, the third longitudinal axis of the second portion of the linkage is positioned to be non-colinear with the first longitudinal axis of the first member.

31. The device of claim 30, wherein the slot of the first member is sized to receive at least a segment of the first portion of the linkage.

32. The device of claim 31, wherein the second member further comprises an internal cavity extended from a third opening within said second top surface to a fourth opening within said second bottom surface.

33. The device of claim 32, wherein said internal cavity of the second member is sized to receive at least a segment of the second portion of the linkage.

34. The device of claim 33, wherein the second member further comprises a second aperture of the second side surface and a third aperture of the second front surface, each of the second aperture and the third aperture sized to receive the interconnecting portion of the linkage, and configured to intersect at least a portion of the internal cavity of the second member.

35. The device of claim 34, wherein the second aperture and the third aperture of the second member intersect such that the second member is configured to enable the interconnecting portion of the linkage to translate between the second aperture and the third aperture.

36. The device of claim 35, wherein, in said first device configuration, the interconnecting portion of the linkage is at least partially positioned in the third aperture of the second member.

37. The device of claim 36, wherein, in said second device configuration, the interconnecting portion of the linkage is at least partially positioned in the second aperture of the second member, and the first side surface of the first member is positioned to face the second side surface of the second member.

38. The device of claim 1, wherein the first portion of the linkage being sized to translate within the first internal channel of the first member comprises the first portion of the linkage being sized for linear movement through the channel in an a first direction from a first point to a second point, the linear movement enabling concurrent movement of an entirety of the linkage in the first direction.

39. The device of claim 12, wherein the first elongate channel of the first member comprises a slot having a cross section, the cross section comprising a first dimension and a second dimension, the first dimension greater than the second dimension, the cross section taken in a plane along the first longitudinal axis between the first top surface and the opposing first bottom surface.

40. The device of claim 20, wherein the translation of the first portion of the linkage apparatus from the first point to the second point through the first elongated channel of the first member enables concurrent movement of an entirety of the linkage apparatus in the direction of the first longitudinal axis of the first member.

41. The device of claim 21, wherein the slot of the first member comprises a cross section having a first dimension and a second dimension, the first dimension greater than the second dimension, the cross section taken in a plane along the first longitudinal axis between the first top surface and the opposing first bottom surface.

42. The device of claim 21, wherein the first portion of the linkage being configured for translation within the slot of the first member comprises the first portion of the linkage being configured for linear movement through the slot in an a first direction from a first point to a second point, the linear movement enabling concurrent movement of an entirety of the linkage in the first direction.

43. The device of claim 30, wherein the slot of the first member comprises a cross section having a first dimension and a second dimension, the first dimension greater than the second dimension, the cross section taken in a plane along the first longitudinal axis between the first top surface and the opposing first bottom surface.

44. The device of claim 30, wherein the first portion of the linkage being configured to translate within the slot of the first member comprises the first portion of the linkage being configured for linear movement through the slot in an a first direction from a first point to a second point, the linear movement enabling concurrent movement of an entirety of the linkage in the first direction.

\* \* \* \* \*